United States Patent
Ohyama et al.

(10) Patent No.: US 8,889,727 B2
(45) Date of Patent: Nov. 18, 2014

(54) TOPICAL ANTIFUNGAL AGENT

(75) Inventors: Makoto Ohyama, Yokohama (JP); Yuji Tabata, Yokohama (JP); Maiko Iida, Yokohama (JP); Kaori Kaneda, Yokohama (JP); Sho Takahata, Yokohama (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/982,734

(22) PCT Filed: Jan. 30, 2012

(86) PCT No.: PCT/JP2012/051991
§ 371 (c)(1),
(2), (4) Date: Jul. 30, 2013

(87) PCT Pub. No.: WO2012/102404
PCT Pub. Date: Aug. 2, 2012

(65) Prior Publication Data
US 2013/0317074 A1    Nov. 28, 2013

(30) Foreign Application Priority Data

Jan. 30, 2011    (JP) .................. 2011-017347

(51) Int. Cl.
| | | |
|---|---|---|
| *A61K 31/415* | (2006.01) | |
| *C07D 231/10* | (2006.01) | |
| *C07D 207/32* | (2006.01) | |
| *C07D 231/12* | (2006.01) | |
| *C07D 231/14* | (2006.01) | |
| *C07D 231/22* | (2006.01) | |
| *C07D 207/34* | (2006.01) | |
| *C07D 207/36* | (2006.01) | |

(52) U.S. Cl.
CPC ............ *C07D 207/32* (2013.01); *C07D 231/12* (2013.01); *C07D 231/14* (2013.01); *C07D 231/22* (2013.01); *C07D 207/34* (2013.01); *C07D 207/36* (2013.01); *A61K 31/415* (2013.01)
USPC ..... 514/406; 514/407; 548/370.4; 548/371.4; 548/376.1

(58) Field of Classification Search
USPC .......... 514/406, 407; 548/370.4, 371.4, 376.1
See application file for complete search history.

(56) References Cited

U.S. PATENT DOCUMENTS

| | | |
|---|---|---|
| 4,826,867 A | 5/1989 | Jensen-Korte et al. |
| 6,916,814 B2 | 7/2005 | Moss et al. |
| 7,265,224 B2 | 9/2007 | Park et al. |
| 2004/0152725 A1 | 8/2004 | Moss et al. |

FOREIGN PATENT DOCUMENTS

| | | |
|---|---|---|
| ES | 2 015 648 A6 | 9/1990 |
| JP | 63-68569 A | 3/1988 |
| JP | 4284169 B2 | 6/2009 |
| WO | WO 03/005999 A2 | 1/2003 |
| WO | WO 2004/033432 A1 | 4/2004 |
| WO | WO 2008/024978 | 2/2008 |

OTHER PUBLICATIONS

Ito, Nobuyuki. Cancer Science 94(1), (2003) 3-8.*
Database Registry Chemical Abstracts Service, Columbus, Ohio, Accession No. RN 83430-98-2, Entered STN: Nov. 16, 1984.*
English-language translation (pp. 1-29) of Kenzo Sirakawa et al., Annual Report by Takeda Research Laboratories, 1963, vol. 22, pp. 27-46.
English-language translation (pp. 1-16) of "Pathogenic Fungus and Mycosis 5", Nanzando, Revised Version 2, pp. 42-45, 184-185, Jul. 9, 2013.

(Continued)

*Primary Examiner* — Samantha Shterengarts
(74) *Attorney, Agent, or Firm* — Holtz, Holtz, Goodman & Chick PC

(57) ABSTRACT

An anti-fungal agent for tinea comprising as active ingredient a compound having the skeleton of 2-(1H-pyrazol-1-yl)phenol represented by the following formula (I) or (II) or a salt thereof is provided

[Chemical formula 8]

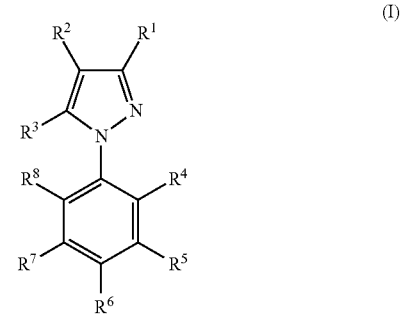

(I)

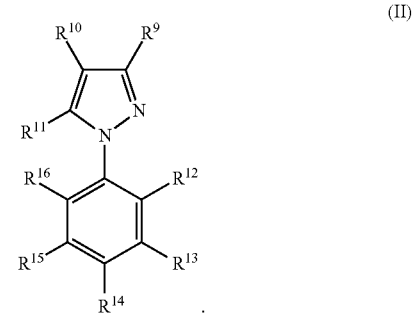

(II)

23 Claims, No Drawings

(56) References Cited

OTHER PUBLICATIONS

Gouki Fukata et al., "Cyclodienones. 9. Reaction of 4-Halo-2,4,6-Tri-Tert-Butyl-2,5-Cyclohexadien-1-Ones With Pyrazoles and Preparation of 1-(2-Hydroxyphenyl) and 1-(4-Hydroxyphenyl)Pyrazoles", *Heterocycles*, 1982, vol. 19, No. 8, pp. 1478-1495.
Pathogenic Fungus and Mycosis 5:, Nanzando, Revised Version 2, pp. 42-45, 2013.
"Pathogenic Fungus and Mycosis", Nanzando, Revised Version 2, pp. 184-187, 2013.
A.K. Gupta et al., "Prevalence and epidemiology of toenail onychomycosis in diabetic subjects: a multicenter survey", British Journal of Dermatology, 1998, vol. 139(4), pp. 665-671 (in English).
Kenzo Sirakawa et al., Annual Report by the Takeda Research Laboratories, 1963, vol. 22, pp. 27-46.
International Search Report (ISR) dated Mar. 19, 2012 (and English translation thereof) issued in International Application No. PCT/JP2012/051991.
Japanese Office Action dated Jul. 9, 2013 (and English translation thereof) issued in counterpart Japanese Application No. 2012-554877.
U.S. Appl. No. 13/954,804, filed Jul. 30, 2013.
Supplementary European Search Report dated Jun. 17, 2014 issued in European Application No. 2011-80027683.4.
Anandarajagopal et al., "Antiepiletic and Antimicrobial Activities of Novel 1-(Unsubstituted/Substituted)-3,5-Dimethyl-1H-Pyrazole Derivatives", *International Journal of ChemTech Research*, vol. 2, No. 1, pp. 45-49 (2010).

\* cited by examiner

TOPICAL ANTIFUNGAL AGENT

CROSS-REFERENCE TO RELATED APPLICATIONS

This application is a United States national phase application of International Application PCT/JP2012/051991, filed Jan. 1, 2012, which claims priority from Japanese Application No. 2011-017347, filed Jan. 30, 2011.

TECHNICAL FIELD

The present invention relates to a novel 2-(1H-pyrazol-1-yl)phenol derivative or a pharmaceutically acceptable salt thereof suitable as an anti-fungal agent for tinea, and an anti-fungal agent for tinea comprising the compound as an active ingredient.

BACKGROUND ART

Mycosis is a disease caused by fungal infection in human and animals. Candidiasis by *Candida* spp., cryptococcosis by *Cryptococcus* spp., aspergillosis by *Aspergillus* spp., zygomycosis by Zygomycetes, dermatophytosis by *Trichophyton* spp., etc. are known as typical mycoses in human (Pathogenic Fungus and Mycosis (Nanzando, Revised version 2), pp. 42-45; Non-patent Document 1).

*Trichophyton* sp. is a dermatophyte which can be a causative agent of tinea, and has a property of keratin degradation. Because of this property, it causes tinea by penetrating into skin, nail and hair (Pathogenic Fungus and Mycosis (Nanzando, Revised Version 2), pp. 184-187; Non-patent Document 2).

Tinea unguium is a nail disease caused by dermatophytes, associated with symptoms such as turbidity, thickening, tearing and deformation of nail plates. In Japan, one out of ten, i.e., approximately 12 million people are said to be the patients of the disease. This disease is frequently found in elderly people, and thus there is a concern about a further increase in the number of patients in years to come. There is a report that patients with diabetes are susceptible to this disease, and possibility of causing severe complications is also indicated.

For the treatment of tinea unguium, only oral antifungal agents (itraconazole and terbinafine) are currently approved in Japan. Topical antifungal agents used for common dermatophytosis cannot penetrate into nail keratin or nail bed, and thus they are not expected to be fully effective. Drug interactions, hepatic disorders and side effects by prolonged administration are big concern for oral antifungal agents. Elderly people having a high risk of tinea unguium and patients with diabetes are likely to take a number of medicines. Therefore, it is difficult to administer oral antifungal agents to them for the treatment of tinea unguium (Br. J. of Dermatol., vol. 139(4), p 665, 1998; Non-patent Document 3).

Topical nail lacquer agent such as amorolfine and ciclopirox have been approved and used overseas. Their penetration property into nails, however, is very low, and their further permeation into nail matrix cells cannot be expected. Therefore, their efficacies are weaker than those of the oral medicines. Recently, studies of antifungal agents and formulations intended for improved nail permeability are underway, but no antifungal agents with sufficient nail permeability have been found.

As a compound having the skeleton of 2-(1H-pyrazol-1-yl)phenol, dimethyl-1H-pyrazol-1-yl)phenol having methyl groups at 3-position and at 5-position of the pyrazol ring is known (Annual Report by the Takeda Research Laboratories (1963) 22, p 27; Non-patent Document 4). These are intended to prevent proliferation of *Mycobacterium tuberculosis*. Non-patent Document 4 has no disclosure of 2-(1H-pyrazol-1-yl)phenol compounds other than 2-(3,5-dimethyl-1H-pyrazol-1-yl)phenol.

As the other compounds having the skeleton of 2-(1H-pyrazol-1-yl) phenol than 2-(3,5-dimethyl-1H-pyrazol-1-yl)phenol, 2-(1H-pyrazol-1-yl)phenol, 2-(3,5-dimethyl-1H-pyrazol-1-yl)-1,4-benzene diol, 2-(4-chloro-3,5-dimethyl-1H-pyrazol-1-yl)-1,4-benzene diol and the like are known. These are used for various chemical reactions and as a material for an electroluminescence element compound (Japanese Patent No. 4284169: Patent Document 1) and a light stabilizer (Spanish Laid-open Patent Publication No. 2015648: Patent Document 2) or the like.

Further, WO 2003/005999 (Patent Document 3) discloses 2-(5-amino-3-tert-butyl-1H-pyrazol-1-yl)-5-methylphenol.

These prior art documents neither suggest nor disclose the anti-*Trichophyton* activity of compounds having the skeleton of 2-(1H-pyrazol-1-yl)phenol.

PRIOR ART LITERATURES

Patent Document

[Patent Document 1] U.S. Pat. No. 4,284,169

[Patent Document 2] Spanish Laid-open Patent Publication No. 2015648

[Patent Document 3] WO 2003/005999

[Non-patent Document 1] Pathogenic Fungus and Mycosis (Nanzando, Revised Version 2), pp. 42-45

[Non-patent Document 2] Pathogenic Fungus and Mycosis (Nanzando, Revised Version 2), pp. 184-187

[Non-patent Document 3] Br. J. of Dermatol., vol. 139(4), p 665, 1998

[Non-patent Document 4] Annual Report by the Takeda Research Laboratories (1963) 22, p 27

SUMMARY OF THE INVENTION

Problems to be Solved by the Invention

As stated above, development of compounds, as a topical therapeutic agent for tinea unguium, having not only an anti-Trichophyton activity but also a high permeability to nails have been desired. Thus, the object of the present invention is to provide a compound having an anti-Trichophyton activity and also nail permeability.

Means to Solve the Problems

The present inventors have found that a compound having the skeleton of 2-(1H-pyrazol-1-yl)phenol represented by the following formula (I) or (II) or a salt thereof unexpectedly has a strong anti-Trichophyton activity, and further has a high nail permeability. The present invention has been completed according to these findings.

[Chemical formula 1]

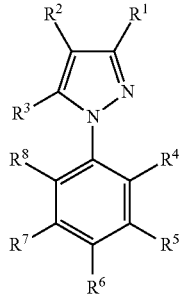

(I)

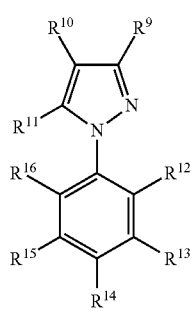

(II)

That is, the present invention is as follows.

(1) A compound represented by the following formula (I), wherein:

$R^1$ represents a hydrogen atom, $C_{1-6}$alkyl or trifluoromethyl;

$R^2$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl);

$R^3$ represents a hydrogen atom, $C_{1-6}$alkyl, amino, trifluoromethyl or —OR (R represents a hydrogen atom or $C_{1-6}$alkyl);

$R^4$ represents a hydroxyl group;

$R^5$ represents a hydrogen atom, $C_{1-6}$alkyl, a hydroxyl group or halogen;

$R^6$ represents a $C_{1-6}$alkyl, trifluoromethyl, halogen, amino, —$NR^aR^b$, nitro, hydroxy $C_{1-6}$alkyl, —$CONR^aR^b$, —COO($C_{1-6}$alkyl), —COOH, —$(CH_2)_{1-3}$COOR, or —$OR^a$ (R represents a hydrogen atom or $C_{1-6}$alkyl, and $R^a$ and $R^b$ may be the same or different from each other and represent a hydrogen atom, $C_{1-6}$alkyl or $C_{1-6}$acyl);

$R^7$ represents a hydrogen atom, $C_{1-6}$alkyl, —OR (R represents a hydrogen atom or $C_{1-6}$alkyl), or halogen; and $R^8$ represents a hydrogen atom, $C_{1-6}$alkyl, a hydroxyl group, amino or nitro, with the proviso that when $R^1$ is a hydrogen atom, $R^3$ is not a hydrogen atom, and the compound wherein $R^1$ is tert-butyl, $R^3$ is amino, $R^4$ is a hydroxyl group and $R^6$ is methyl is excluded, or a salt thereof.

[Chemical formula 2]

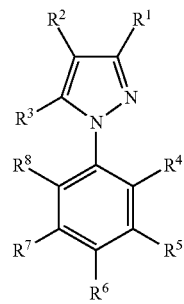

(I)

(2) The compound according to (1),
wherein:
$R^1$ represents a $C_{1-6}$alkyl or trifluoromethyl; and
$R^3$ represents a $C_{1-6}$alkyl, trifluoromethyl, or —OR (R represents a hydrogen atom or $C_{1-6}$alkyl), or a salt thereof (3) The compound according to (1),
wherein:
$R^1$ represents a $C_{1-6}$alkyl; and
$R^3$ represents a $C_{1-6}$alkyl, or a salt thereof (4) The compound according to (1),
wherein:
$R^1$ represents a $C_{1-4}$alkyl;
$R^2$ represents a hydrogen atom, $C_{1-4}$alkyl, or halogen;
$R^3$ represents a $C_{1-4}$alkyl;
$R^4$ represents a hydroxyl group;
$R^5$ represents a hydrogen atom;
$R^6$ represents a $C_{1-4}$alkyl, trifluoromethyl, halogen, amino, —$NR^aR^b$, nitro, hydroxy $C_{1-4}$alkyl, —$CONR^aR^b$, —COO($C_{1-4}$alkyl), —COOH, —$(CH_2)_{1-3}$COOR, or —$OR^a$ (R represents a hydrogen atom or $C_{1-4}$alkyl, and $R^a$ and $R^b$ may be the same or different from each other and represent a hydrogen atom, $C_{1-4}$alkyl or $C_{1-4}$acyl);
$R^7$ represents a hydrogen atom; and
$R^8$ represents a hydrogen atom, $C_{1-4}$alkyl, a hydroxyl group, amino, or nitro,
or a salt thereof (5) The compound according to (1),
wherein:
$R^1$ represents a methyl;
$R^2$ represents a hydrogen atom, methyl or halogen;
$R^3$ represents a methyl;
$R^4$ represents a hydroxyl group;
$R^5$ represents a hydrogen atom;
$R^6$ represents a $C_{1-3}$alkyl, trifluoromethyl, halogen, amino, —$NR^aR^b$, nitro, hydroxy $C_{1-3}$alkyl, —$CONR^aR^b$, —COO($C_{1-3}$alkyl), —COOH, —$(CH_2)_{1-3}$COOR, or —$OR^a$ (R represents a hydrogen atom or $C_{1-3}$alkyl, $R^a$ and $R^b$ may be the same or different from each other and represent a hydrogen atom, $C_{1-3}$alkyl or $C_{1-3}$acyl);
$R^7$ represents a hydrogen atom; and
$R^8$ represents a hydrogen atom,
or a salt thereof (6) Further, there is provided the compound which is:
2-(3,5-dimethyl-1H-pyrazol-1-yl)-4-fluorophenol
2-(5-hydroxy-3-methyl-1H-pyrazol-1-yl)phenol
2-(5-methyl-3-(trifluoromethyl)-1H-pyrazol-1-yl)phenol
2-(3,5-bistrifluoromethyl)-1H-pyrazol-1-yl)phenol
2-(3-methyl-1H-pyrazol-1-yl)phenol
2-(5-methyl-1H-pyrazol-1-yl)phenol
2-(3,4,5-trimethyl-1H-pyrazol-1-yl)phenol
2-(5-amino-3-tert-butyl-1H-pyrazol-1-yl)phenol 4-chloro-2-(3,5-dimethyl-1H-pyrazol-1-yl)phenol
2-chloro-6-(3,5-dimethyl-1H-pyrazol-1-yl)phenol
2-(4-chloro-3,5-dimethyl-1H-pyrazol-1-yl)phenol
2-(3,5-diethyl-1H-pyrazol-1-yl)phenol
3-(3,5-dimethyl-1H-pyrazol-1-yl)benzene-1,2-diol
2-(4-ethyl-3,5-dimethyl-1H-pyrazol-1-yl)phenol
5-fluoro-2-(3,4,5-trimethyl-1H-pyrazol-1-yl)phenol
4-fluoro-2-(3,4,5-trimethyl-1H-pyrazol-1-yl)phenol
2-(4-chloro-3,5-dimethyl-1H-pyrazol-1-yl)-5-fluorophenol
ethyl 1-(2-hydroxyphenyl)-3,5-dimethyl-1H-pyrazol-4-carboxylate
methyl 3-(1-(2-hydroxyphenyl)-3,5-dimethyl-1H-pyrazol-4-yl)propanoate
2-(4-butyl-3,5-dimethyl-1H-pyrazol-1-yl)phenol
2-(3,5-dimethyl-1H-pyrazol-1-yl)-5-fluorophenol
5-chloro-2-(3,5-dimethyl-1H-pyrazol-1-yl)phenol
2-(3,5-dimethyl-1H-pyrazol-1-yl)-3-nitrophenol
2-(3,5-dimethyl-1H-pyrazol-1-yl)-5-nitrophenol
3-(1-(2-hydroxyphenyl)-3,5-dimethyl-1H-pyrazol-4-yl)propionic acid
5-chloro-2-(3,4,5-trimethyl-1H-pyrazol-1-yl)phenol
5-amino-2-(3,5-dimethyl-1H-pyrazol-1-yl)phenol
5-nitro-2-(3,4,5-trimethyl-1H-pyrazol-1-yl)phenol
4-(3,5-dimethyl-1H-pyrazol-1-yl)benzene-1,3-diol
5-amino-2-(3,4,5-trimethyl-1H-pyrazol-1-yl)phenol
methyl 4-(3,5-dimethyl-1H-pyrazol-1-yl)-3-hydroxybenzene carboxylate
3-amino-2-(3,5-dimethyl-1H-pyrazol-1-yl)phenol
4-(3,5-dimethyl-1H-pyrazol-1-yl)-3-hydroxybenzene carboxylic acid
4-(3,5-dimethyl-1H-pyrazol-1-yl)-3-hydroxy-N,N-dimethyl benzamide
4-(3,5-dimethyl-1H-pyrazol-1-yl)-3-hydroxy benzamide
3-hydroxy-4-(3,4,5-trimethyl-1H-pyrazol-1-yl)benzene carboxylic acid
3-hydroxy-4-(3,4,5-trimethyl-1H-pyrazol-1-yl)benzamide
4-(4-chloro-3,5-dimethyl-1H-pyrazol-1-yl)-3-hydroxy benzamide
2-(3,5-dimethyl-1H-pyrazol-1-yl)benzene-1,3-diol
2-(3,5-dimethyl-1H-pyrazol-1-yl)-5-methylphenol
2-(3,5-dimethyl-1H-pyrazol-1-yl)-5-methoxyphenol
2-(3,5-dimethyl-1H-pyrazol-1-yl)-3-methylphenol
2-(3,5-dimethyl-1H-pyrazol-1-yl)-5-hydroxymethylphenol
2-(3,5-dimethyl-1H-pyrazol-1-yl)-5-methylaminophenol
2-(3,5-dimethyl-1H-pyrazol-1-yl)-4-methylphenol
2-(3,5-dimethyl-1H-pyrazol-1-yl)-5-trifluoromethylphenol
2-(3,5-dimethyl-1H-pyrazol-1-yl)-6-methylphenol
2-(3,5-dimethyl-1H-pyrazol-1-yl)-5-ethylphenol
2-(4-fluoro-3,5-dimethyl-1H-pyrazol-1-yl)phenol
5-bromo-2-(3,5-dimethyl-1H-pyrazol-1-yl)phenol
5-bromo-2-(4-chloro-3,5-dimethyl-1H-pyrazol-1-yl)phenol
5-bromo-2-(3,4,5-trimethyl-1H-pyrazol-1-yl)phenol
4-(3,5-dimethyl-1H-pyrazol-1-yl)-3-hydroxyphenyl acetate
4-(4-chloro-3,5-dimethyl-1H-pyrazol-1-yl)-3-hydroxyphenyl acetate
3-hydroxy-4-(3,4,5-trimethyl-1H-pyrazol-1-yl)phenyl acetate
2-(3,5-dimethyl-1H-pyrazol-1-yl)-4-methoxy-5-methylphenol
4-chloro-2-(3,5-dimethyl-1H-pyrazol-1-yl)-5-methylphenol
2-(3,5-dimethyl-1H-pyrazol-1-yl)-4,5-dimethylphenol or
4-(4-chloro-3,5-dimethyl-1H-pyrazol-1-yl)-benzene-1,3-diol
or a salt thereof.

In another embodiment, the present invention provides:
(7) An anti-fungal agent for tinea comprising a compound represented by the following formula (II), wherein:

$R^9$ represents a hydrogen atom, $C_{1-6}$alkyl or trifluoromethyl;
$R^{10}$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl),
$R^{11}$ represents a hydrogen atom, $C_{1-6}$alkyl, amino, trifluoromethyl or —OR(R represents a hydrogen atom or $C_{1-6}$alkyl);
$R^{12}$ represents a hydroxyl group;
$R^{13}$ represents a hydrogen atom, $C_{1-6}$alkyl, a hydroxyl group or halogen;
$R^{14}$ represents a hydrogen atom, $C_{1-6}$alkyl, trifluoromethyl, halogen, amino, —$NR^aR^b$, nitro, hydroxy $C_{1-6}$alkyl, —$CONR^aR^b$, —COO($C_{1-6}$alkyl), —COOH, —$(CH_2)_{1-3}$COOR, or —$OR^a$ (R represents a hydrogen atom or $C_{1-6}$alkyl, and $R^a$ and $R^b$ may be the same or different from each other and represent a hydrogen atom, $C_{1-6}$alkyl or $C_{1-6}$acyl);
$R^{15}$ represents a hydrogen atom, $C_{1-6}$alkyl, —OR (R represents a hydrogen atom or $C_{1-6}$alkyl) or halogen; and
$R^{16}$ represents a hydrogen atom, $C_{1-6}$alkyl, a hydroxyl group, amino or nitro,
or a salt thereof.

[Chemical formula 3]

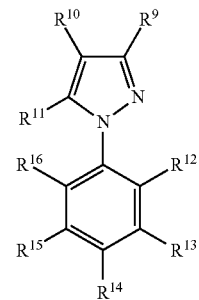

(II)

(8) An anti-Trichophyton unguium agent comprising a compound of (1) or (7) or a salt thereof;
(9) The anti-fungal agent for tinea according to (7), which is a topical agent;
(10) The anti-Trichophyton unguium agent according to (9), which is a topical agent.

The term "$C_{1-6}$alkyl" or "$C_{1-6}$alkyl" as a moiety of a group as used herein refers to an alkyl group having a carbon number of 1 to 6. This alkyl group may be linear, branched or ring. Examples include $C_{1-6}$alkyl group such as methyl, ethyl, propyl, isopropyl, butyl, isobutyl, sec-butyl, tert-butyl, pentyl and hexyl; and $C_{3-6}$cycloalkyl group such as cyclopropyl, cyclobutyl, cyclopentyl and cyclohexyl.

The term "$C_{1-6}$acyl" or "$C_{1-6}$acyl" as a moiety of a group as used herein refers to an acyl group having a carbon number of 1 to 6. This acyl group may be linear, branched or ring. Examples include formyl, acetyl, propionyl, butyryl and isobutyryl. Preferred examples include formyl, acetyl, propionyl and butyryl.

"Halogen" as used herein includes fluorine, chlorine, bromine and iodine.

The term "—OR (R represents a hydrogen atom or $C_{1-6}$alkyl)" which is a group or a moiety of a group as used herein represents a hydroxyl group or $C_{1-6}$alkyloxy. "$C_{1-6}$alkyl" is as defined for the above "$C_{1-6}$alkyl".

In "—$OR^a$" which is a group or a moiety of a group as used herein, $R_a$ represents a hydrogen atom, $C_{1-6}$alkyl or $C_{1-6}$acyl, and "—OR$^a$" represents a hydroxyl group, $C_{1-6}$alkyloxy or $C_{1-6}$acyloxy. "$C_{1-6}$alkyl" is as defined for the above "$C_{1-6}$alkyl".

In the above formula (I), $R^1$ represents a hydrogen atom, $C_{1-6}$alkyl or trifluoromethyl; preferably, $C_{1-6}$alkyl or trifluoromethyl; more preferably $C_{1-6}$alkyl; and furthermore preferably $C_{1-3}$alkyl.

Specific examples include a hydrogen atom, methyl, ethyl, propyl, isopropyl, butyl, tert-butyl and trifluoromethyl. More preferred examples include a hydrogen atom, methyl, ethyl, butyl, tert-butyl, and trifluoromethyl. The most preferred examples include methyl.

$R^2$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl). $R^2$ preferably represents a hydrogen atom, $C_{1-6}$alkyl, or halogen; and more preferably represents a hydrogen atom, $C_{1-3}$alkyl, or halogen.

Specific examples include a hydrogen atom, methyl, ethyl, propyl, isopropyl, butyl, tert-butyl, chlorine, bromine, fluorine, methyloxycarbonyl, ethyloxycarbonyl, methyloxylcarbonylethyl, ethyloxycarbonylethyl, methyloxycarbonylmethyl, ethyloxycarbonylmethyl, hydroxycarbonylmethyl, and hydroxycarbonylethyl. More preferred examples include a hydrogen atom, methyl, ethyl, butyl, tert-butyl, chlorine, ethyloxycarbonyl, methyloxycarbonylmethyl, and hydroxycarbonylethyl. The most preferred examples include a hydrogen atom, methyl, and halogen.

$R^3$ represents a hydrogen atom, $C_{1-6}$alkyl, amino, trifluoromethyl or —OR(R represents a hydrogen atom or $C_{1-6}$alkyl). Preferred examples include a hydrogen atom, $C_{1-6}$alkyl, trifluoromethyl and —OR (R represents a hydrogen atom or $C_{1-6}$alkyl). More preferred examples include $C_{1-6}$alkyl, and furthermore preferred examples include $C_{1-3}$alkyl.

Specific examples include a hydrogen atom, methyl, ethyl, propyl, isopropyl, butyl, tert-butyl, amino, trifluoromethyl, a hydroxyl group, methoxy, and ethoxy. Preferred examples include a hydrogen atom, methyl, ethyl, amino, trifluoromethyl, and a hydroxyl group. The most preferred examples include methyl.

$R^4$ represents a hydroxyl group.

$R^5$ represents a hydrogen atom, $C_{1-6}$alkyl, a hydroxyl group or halogen; and preferably represents a hydrogen atom, or $C_{1-4}$ alkyl.

Specific examples include a hydrogen atom, methyl, ethyl, propyl, isopropyl, butyl, tert-butyl, a hydroxyl group, chlorine, bromine, and fluorine. Preferred examples include a hydrogen atom, methyl, chlorine, and a hydroxyl group. More preferred examples include a hydroxyl group, chlorine, and methyl, and the most preferred example includes a hydrogen atom.

$R^6$ represents a $C_{1-6}$alkyl, trifluoromethyl, halogen, amino, —NR$^a$R$^b$, nitro, hydroxy $C_{1-6}$alkyl, —CONR$^a$R$^b$, —COO($C_{1-6}$alkyl), —COOH, —$(CH_2)_{1-3}$COOR, or —OR$^a$ (R represents a hydrogen atom or $C_{1-6}$alkyl, and R$^a$ and R$^b$ may be the same or different from each other and represent a hydrogen atom, $C_{1-6}$alkyl or $C_{1-6}$acyl). Preferred examples include $C_{1-4}$alkyl, trifluoromethyl, amino, —NR$^a$R$^b$, nitro, hydroxy $C_{1-4}$alkyl, —CONR$^a$R$^b$, —COO($C_{1-4}$alkyl), —COOH, —$(CH_2)_{1-3}$COOR, or —OR$^a$ (R represents a hydrogen atom or $C_{1-4}$alkyl, and R$^a$ and R$^b$ may be the same or different from each other and represent a hydrogen atom, $C_{1-4}$alkyl or $C_{1-4}$acyl).

More preferred examples include $C_{1-3}$alkyl, trifluoromethyl, amino, —NR$^a$R$^b$, nitro, hydroxy $C_{1-3}$alkyl, —CONR$^a$R$^b$, —COO($C_{1-3}$alkyl), —COOH, —$(CH_2)_{1-3}$COOR, or —OR$^a$ (R represents a hydrogen atom or $C_{1-3}$alkyl, and R$^a$ and R$^b$ may be the same or different from each other and represent a hydrogen atom, $C_{1-3}$alkyl or $C_{1-3}$acyl).

Specific examples include methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy, and a hydroxyl group. More preferred examples include methyl, ethyl, trifluoromethyl, chlorine, fluorine, amino, methylamino, nitro, hydroxymethyl, carbamoyl, N,N-dimethylcarbamoyl, methyloxycarbonyl, —COOH, methoxy, acetyloxy, and a hydroxyl group.

$R^7$ represents a hydrogen atom, $C_{1-6}$alkyl, —OR (R represents a hydrogen atom or $C_{1-6}$alkyl), or halogen, and preferably represents a hydrogen atom, $C_{1-4}$alkyl or —OR (R represents a hydrogen atom or $C_{1-4}$alkyl).

Specific examples include a hydrogen atom, methyl, ethyl, propyl, isopropyl, butyl, tert-butyl, methoxy, ethoxy, propyloxy, a hydroxyl group, chlorine, bromine, and fluorine. Preferred examples include a hydrogen atom, methyl, methoxy, propyloxy, tert-butyloxy, chlorine, fluorine, and a hydroxyl group. More preferred examples include a hydrogen atom, methyl, methoxy, and chlorine, and the most preferred examples include a hydrogen atom.

$R^8$ represents a hydrogen atom, $C_{1-6}$alkyl, a hydroxyl group, amino or nitro; preferably represents a hydrogen atom, $C_{1-4}$alkyl, a hydroxyl group, amino, or nitro; and more preferably represents a hydrogen atom, $C_{1-3}$alkyl, a hydroxyl group, amino, or nitro.

Specific examples include a hydrogen atom, methyl, ethyl, propyl, isopropyl, butyl, tert-butyl, a hydroxyl group, amino, and nitro. Preferred examples include a hydrogen atom, methyl, a hydroxyl group, amino, and nitro. The most preferred examples include a hydrogen atom.

With the proviso that when $R^1$ is a hydrogen atom, $R^3$ is not a hydrogen atom, and the compound wherein $R^1$ is tert-butyl, $R^3$ is amino, $R^4$ is a hydroxyl group and $R^6$ is methyl is excluded In the above formula (II), $R^9$ represents a hydrogen atom, $C_{1-6}$alkyl or trifluoromethyl. Preferred examples include hydrogen atom, $C_{1-4}$alkyl and trifluoromethyl. Specific examples include a hydrogen atom, methyl, ethyl, propyl, isopropyl, butyl, tert-butyl and trifluoromethyl. More preferred examples include a hydrogen atom, methyl, ethyl, butyl, tert-butyl and trifluoromethyl.

$R^{10}$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl). Preferred examples include a hydrogen atom, $C_{1-4}$alkyl, halogen, —COO($C_{1-4}$alkyl) and —$(CH_2)_{1-3}$COOR(R represents a hydrogen atom or $C_{1-4}$alkyl).

Specific examples include a hydrogen atom, methyl, ethyl, propyl, isopropyl, butyl, tert-butyl, chlorine, bromine, fluorine, methyloxycarbonyl, ethyloxycarbonyl, methyloxycarbonylethyl, ethyloxycarbonylethyl, methyloxycarbonylmethyl, ethyloxycarbonylmethyl, hydroxycarbonylmethyl and hydroxycarbonylethyl. More preferred examples include a hydrogen atom, methyl, ethyl, butyl, tert-butyl, chlorine, ethyloxycarbonyl, methyloxycarbonylmethyl and hydroxycarbonylethyl.

$R^{11}$ represents a hydrogen atom, $C_{1-6}$alkyl, amino, trifluoromethyl or —OR(R represents a hydrogen atom or $C_{1-6}$alkyl). Preferred examples include a hydrogen atom, $C_{1-4}$alkyl, amino, trifluoromethyl and —OR (R represents a hydrogen atom or $C_{1-4}$alkyl). Specific examples include a hydrogen atom, methyl, ethyl, propyl, isopropyl, butyl, tert-butyl, amino, trifluoromethyl, a hydroxyl group, methoxy and ethoxy. More preferred examples include a hydrogen atom, methyl, ethyl, amino, trifluoromethyl and a hydroxyl group.

$R^{12}$ represents a hydroxyl group.

$R^{13}$ represents a hydrogen atom, $C_{1-6}$alkyl, a hydroxyl group or halogen. Preferred examples include a hydrogen atom, $C_{1-4}$alkyl, a hydroxyl group and halogen. Specific examples include a hydrogen atom, methyl, ethyl, propyl, isopropyl, butyl, tert-butyl, a hydroxyl group, chlorine, bromine and fluorine. More preferred examples include a hydrogen atom, methyl, chlorine and a hydroxyl group.

$R^{14}$ represents a hydrogen atom, $C_{1-6}$alkyl, trifluoromethyl, halogen, amino, —$NR^aR^b$, nitro, hydroxy$C_{1-6}$alkyl, —$CONR^aR^b$, —COO($C_{1-6}$alkyl), —COOH, —$(CH_2)_{1-3}$COOR, or —$OR^a$ (R represents a hydrogen atom or $C_{1-6}$alkyl, and $R^a$ and $R^b$ may be the same or different from each other and represent a hydrogen atom, $C_{1-6}$alkyl or $C_{1-6}$acyl).

Preferred examples include a hydrogen atom, $C_{1-4}$alkyl, trifluoromethyl, halogen, amino, —$NR^aR^b$, nitro, hydroxy$C_{1-4}$alkyl, —$CONR^aR^b$, —COO($C_{1-4}$alkyl), —COOH, —$(CH_2)_{1-3}$COOR, or —$OR^a$ (R represents a hydrogen atom or $C_{1-4}$alkyl, and $R^a$ and $R^b$ may be the same or different from each other and represent a hydrogen atom, $C_{1-4}$alkyl or $C_{1-4}$acyl).

Specific examples include a hydrogen atom, methyl, ethyl, propyl, isopropyl, butyl, tert-butyl, trifluoromethyl, chlorine, bromine, fluorine, amino, methylamino, ethylamino, dimethylamino, diethyl amino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy and a hydroxyl group. More preferred examples include a hydrogen atom, methyl, ethyl, trifluoromethyl, chlorine, fluorine, amino, methylamino, nitro, hydroxymethyl, carbamoyl, N,N-dimethylcarbamoyl, methyloxycarbonyl, —COOH, methoxy, acetyloxy and a hydroxyl group.

$R^{15}$ represents a hydrogen atom, $C_{1-6}$alkyl, —OR (R represents a hydrogen atom or $C_{1-6}$alkyl) or halogen. Preferred examples include a hydrogen atom, $C_{1-4}$alkyl, —OR (R represents a hydrogen atom or $C_{1-4}$alkyl), and halogen. Specific examples include a hydrogen atom, methyl, ethyl, propyl, isopropyl, butyl, tert-butyl, methoxy, ethoxy, propyloxy, tert-butyloxy, a hydroxyl group, chlorine, bromine and fluorine. More preferred examples include a hydrogen atom, methyl, chlorine, fluorine and a hydroxyl group.

$R^{16}$ represents a hydrogen atom, $C_{1-6}$alkyl, a hydroxyl group, amino or nitro. Preferred examples include a hydrogen atom, $C_{1-4}$alkyl, a hydroxyl group, amino and nitro. Specific examples include a hydrogen atom, methyl, ethyl, propyl, isopropyl, butyl, tert-butyl, a hydroxyl group, amino and nitro. More preferred examples include a hydrogen atom, methyl, a hydroxyl group, amino and nitro.

The present invention is a compound represented by the formula (I) or a salt thereof. The present invention is also an anti-fungal agent for tinea comprising a compound represented by the formula (II) or a salt thereof as another embodiment. Preferred examples include an anti-Trichophyton unguium agent, and more preferred examples include a topical anti-fungal agent for tinea and a topical anti-Trichophyton unguium agent.

The present invention is a compound represented by the above formula (I), wherein:

$R^1$ represents a hydrogen atom, $C_{1-6}$alkyl or trifluoromethyl;
$R^2$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl);
$R^3$ represents a hydrogen atom, $C_{1-6}$alkyl, amino, trifluoromethyl or —OR (R represents a hydrogen atom or $C_{1-6}$alkyl);
$R^4$ represents a hydroxyl group;
$R^5$ represents a hydrogen atom, $C_{1-6}$alkyl, a hydroxyl group or halogen;
$R^6$ represents a $C_{1-6}$alkyl, trifluoromethyl, halogen, amino, —$NR^aR^b$, nitro, hydroxy$C_{1-6}$alkyl, —$CONR^aR^b$, —COO($C_{1-6}$alkyl), —COOH, —$(CH_2)_{1-3}$COOR, or —$OR^a$ (R represents a hydrogen atom or $C_{1-6}$alkyl, and $R^a$ and $R^b$ may be the same or different from each other and represent a hydrogen atom, $C_{1-6}$alkyl or $C_{1-6}$acyl);
$R^7$ represents a hydrogen atom, $C_{1-6}$alkyl, —OR (R represents a hydrogen atom or $C_{1-6}$alkyl), or halogen; and
$R^8$ represents a hydrogen atom, $C_{1-6}$alkyl, a hydroxyl group, amino or nitro, with the proviso that when $R^1$ is a hydrogen atom, $R^3$ is not a hydrogen atom, and the compound wherein $R^1$ is tert-butyl, $R^3$ is amino, $R^4$ is a hydroxyl group and $R^6$ is methyl is excluded,
or a salt thereof.

Preferably, in the above formula (I), $R^1$ represents a hydrogen atom, $C_{1-4}$alkyl or trifluoromethyl; $R^2$ represents a hydrogen atom, $C_{1-4}$alkyl, halogen, —COO($C_{1-4}$alkyl) or —$(CH_2)_{1-3}$COOR (R represents a hydrogen atom or $C_{1-4}$alkyl); $R^3$ represents a hydrogen atom, $C_{1-4}$alkyl, amino, trifluoromethyl or —OR (R represents a hydrogen atom or $C_{1-4}$alkyl); $R^4$ represents a hydroxyl group; $R^5$ represents a hydrogen atom, $C_{1-4}$alkyl, a hydroxyl group or halogen; $R^6$ represents $C_{1-4}$alkyl, trifluoromethyl, halogen, amino, —$NR^aR^b$, nitro, hydroxy$C_{1-4}$alkyl, —$CONR^aR^b$, —COO($C_{1-4}$alkyl), —COOH, —$(CH_2)_{1-3}$COOR, or —$OR^a$ (R represents a hydrogen atom or $C_{1-4}$alkyl, and $R^a$ and $R^b$ may be the same or different from each other and represent a hydrogen atom, $C_{1-4}$alkyl or $C_{1-4}$acyl); $R^7$ represents a hydrogen atom, $C_{1-4}$alkyl, —OR (R represents a hydrogen atom or $C_{1-6}$alkyl), or halogen; and $R^8$ represents a hydrogen atom, $C_{1-4}$alkyl, a hydroxyl group, amino or nitro, with the proviso that when $R^1$ is a hydrogen atom, $R^3$ is not a hydrogen atom, and the compound wherein $R^1$ is tert-butyl, $R^3$ is amino, $R^4$ is a hydroxyl group and $R^6$ is methyl is excluded.

In the preferred specific substituent of the formula (I), $R^1$ represents a hydrogen atom, methyl, ethyl, propyl, isopropyl, butyl, tert-butyl, or trifluoromethyl; $R^2$ represents a hydrogen atom, methyl, ethyl, propyl, isopropyl, butyl, tert-butyl, chlorine, bromine, fluorine, methyloxycarbonyl, ethyloxycarbonyl, methyloxycarbonylethyl, ethyoxycarbonylethyl, methyloxycarbonylmethyl, ethyloxycarbonylmethyl, hydroxycarbonylmethyl, or hydroxycarbonylethyl; $R^3$ represents a hydrogen atom, methyl, ethyl, propyl, isopropyl, butyl, tert-butyl, amino, trifluoromethyl, a hydroxyl group, methoxy, or ethoxy; $R^4$ represents a hydroxyl group; $R^5$ represents a hydrogen atom, methyl, ethyl, propyl, isopropyl, butyl, tert-butyl, a hydroxyl group, chlorine, bromine or a fluorine; $R^6$ represents methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy, or a hydroxyl group; $R^7$ represents a hydrogen atom, methyl, ethyl, propyl, isopropyl, butyl, tert-butyl, methoxy, ethoxy, propyloxy, tert-butyloxy, a hydroxyl group, chlorine, bromine, or fluorine; and $R^8$ represents a hydrogen atom, methyl, ethyl, propyl, isopropyl, butyl, tert-butyl, a hydroxyl group, amino or nitro, with the proviso that when $R^1$ is a hydrogen atom, $R^3$ is not a hydrogen atom, and the compound wherein R' is tert-butyl, $R^3$ is amino, $R^4$ is a hydroxyl group and $R^6$ is methyl is excluded.

More preferably, $R^1$ represents methyl, ethyl, propyl, isopropyl, butyl, tert-butyl or trifluoromethyl; $R^2$ represents a hydrogen atom, methyl, ethyl, propyl, isopropyl, butyl, tert-butyl, chlorine, bromine, fluorine, methyloxycarbonyl, ethyloxycarbonyl, methyloxycarbonylethyl, ethyloxycarbonylethyl, methyloxycarbonylmethyl, ethyloxycarbonylmethyl, hydroxycarbonylmethyl or hydroxycarbonylethyl; $R^3$ represents methyl, ethyl, propyl, isopropyl, butyl, tert-butyl, trifluoromethyl, a hydroxyl group, methoxy or ethoxy; $R^4$ represents a hydroxyl group; $R^5$ represents a hydrogen atom, methyl, ethyl, propyl, isopropyl, butyl, tert-butyl, a hydroxyl group, chlorine, bromine or fluorine; $R^6$ represents methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy, or a hydroxyl group; $R^7$ represents a hydrogen atom, methyl, ethyl, propyl, isopropyl, butyl, tert-butyl, methoxy, ethoxy, propyloxy, tert-butyloxy, a hydroxyl group, chlorine, bromine, or fluorine; and $R^8$ represents a hydrogen atom, methyl, ethyl, propyl, isopropyl, butyl, tert-butyl, a hydroxyl group, amino, nitro, with the proviso that the compound wherein $R^1$ is tert-butyl, $R^3$ is amino, $R^4$ is a hydroxyl group and $R^6$ is methyl is excluded.

Furthermore preferably, $R^1$ represents methyl, ethyl, propyl, isopropyl, butyl or tert-butyl; $R^2$ represents a hydrogen atom, methyl, ethyl, propyl, isopropyl, butyl, tert-butyl, chlorine, bromine, fluorine, methyloxycarbonyl, ethyloxycarbonyl, methyloxycarbonylethyl, ethyloxycarbonylethyl, methyloxycarbonylmethyl, ethyloxycarbonylmethyl, hydroxycarbonylmethyl or hydroxycarbonylethyl; $R^3$ represents methyl, ethyl, propyl, isopropyl, butyl or tert-butyl; $R^4$ represents a hydroxyl group; $R^5$ represents a hydrogen atom, methyl, ethyl, propyl, isopropyl, butyl, tert-butyl, a hydroxyl group, chlorine, bromine or fluorine; $R^6$ represents methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy or a hydroxyl group; $R^7$ represents a hydrogen atom, methyl, ethyl, propyl, isopropyl, butyl, tert-butyl, methoxy, ethoxy, propyloxy, tert-butyloxy, a hydroxyl group, chlorine, bromine, or fluorine; and $R^8$ represents a hydrogen atom, methyl, ethyl, propyl, isopropyl, butyl, tert-butyl, a hydroxyl group, amino or nitro.

In the more preferred formula (I), $R^1$ represents methyl, ethyl, propyl, isopropyl, butyl or tert-butyl; $R^2$ represents a hydrogen atom, methyl, ethyl, propyl, isopropyl, butyl, tert-butyl, chlorine, bromine or fluorine; $R^3$ represents methyl, ethyl, propyl, isopropyl, butyl or tert-butyl; $R^4$ represents a hydroxyl group; $R^5$ represents a hydrogen atom; $R^6$ represents methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy or a hydroxyl group; $R^7$ represents a hydrogen atom; and $R^8$ represents a hydrogen atom, methyl, ethyl, propyl, isopropyl, butyl, tert-butyl, a hydroxyl group, amino or nitro.

Most preferably, $R^1$ represents methyl; $R^2$ represents a hydrogen atom, methyl or chlorine; $R^3$ represents methyl; $R^4$ represents a hydroxyl group; $R^5$ represents a hydrogen atom; $R^6$ represents methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy or a hydroxyl group; $R^7$ represents a hydrogen atom; and $R^8$ represents a hydrogen atom.

The present invention is an anti-fungal agent for tinea comprising a compound represented by the above formula (II) or a salt thereof (wherein $R^9$ represents a hydrogen atom, $C_{1-6}$alkyl or trifluoromethyl; $R^{10}$ represents a hydrogen atom, $C_{1-6}$alkyl, halogen, —COO($C_{1-6}$alkyl) or —$(CH_2)_{1-3}$COOR (R represents a hydrogen atom or $C_{1-6}$alkyl); $R^{11}$ represents a hydrogen atom, $C_{1-6}$alkyl, amino, trifluoromethyl or —OR (R represents a hydrogen atom or $C_{1-6}$alkyl); $R^{12}$ represents a hydroxyl group; $R^{13}$ represents a hydrogen atom, $C_{1-6}$alkyl, a hydroxyl group or halogen; $R^{14}$ represents a hydrogen atom, $C_{1-6}$alkyl, trifluoromethyl, halogen, amino, —$NR^aR^b$, nitro, hydroxy $C_{1-6}$alkyl, —$CONR^aR^b$, —COO($C_{1-6}$alkyl), —COOH, —$(CH_2)_{1-3}$COOR, or —$OR^a$ (R represents a hydrogen atom or $C_{1-6}$alkyl, and $R^a$ and $R^b$ may be the same or different from each other and represent a hydrogen atom, $C_{1-6}$alkyl or $C_{1-6}$acyl); $R^{15}$ represents a hydrogen atom, $C_{1-6}$alkyl, —OR (R represents a hydrogen atom or $C_{1-6}$alkyl) or halogen; and $R^{16}$ represents a hydrogen atom, $C_{1-4}$alkyl, a hydroxyl group, amino or nitro.

Preferably, $R^9$ represents a hydrogen atom, $C_{1-4}$alkyl or trifluoromethyl; $R^{10}$ represents a hydrogen atom, $C_{1-4}$alkyl, halogen, —COO($C_{1-4}$alkyl) or —$(CH_2)_{1-3}$COOR (R represents a hydrogen atom or $C_{1-4}$alkyl); $R^{11}$ represents a hydrogen atom, $C_{1-4}$alkyl, amino, trifluoromethyl or —OR (R represents a hydrogen atom or $C_{1-4}$alkyl); $R^{12}$ represents a hydroxyl group; $R^{13}$ represents a hydrogen atom, $C_{1-4}$alkyl, a hydroxyl group or halogen; $R^{14}$ represents a hydrogen atom, $C_{1-4}$alkyl, trifluoromethyl, halogen, amino, —$NR^aR^b$, nitro, hydroxy $C_{1-4}$alkyl, —$CONR^aR^b$, —COO($C_{1-4}$alkyl), —COOH, —$(CH_2)_{1-3}$COOR, or —$OR^a$ (R represents a hydrogen atom or $C_{1-4}$alkyl, and $R^a$ and $R^b$ may be the same or different from each other and represent a hydrogen atom, $C_{1-4}$alkyl or $C_{1-4}$acyl); $R^{15}$ represents a hydrogen atom, $C_{1-4}$alkyl, —OR (R represents a hydrogen atom or $C_{1-4}$alkyl), or halogen; and $R^{16}$ represents a hydrogen atom, $C_{1-4}$alkyl, a hydroxyl group, amino or nitro.

In the more preferable formula (II), $R^9$ represents a hydrogen atom, methyl, ethyl, propyl, isopropyl, butyl, tert-butyl or trifluoromethyl; $R^{10}$ represents a hydrogen atom, methyl, ethyl, propyl, isopropyl, butyl, tert-butyl, chlorine, bromine, fluorine, methyloxycarbonyl, ethyloxycarbonyl, methyloxycarbonylethyl, ethyloxycarbonylethyl, methyloxycarbonylmethyl, ethyloxycarbonylmethyl, hydroxycarbonylmethyl or hydroxycarbonylethyl; $R^{11}$ represents a hydrogen atom, methyl, ethyl, propyl, isopropyl, butyl, tert-butyl, amino, trifluoromethyl, a hydroxyl group, methoxy or ethoxy; $R^{12}$ represents a hydroxyl group; $R^{13}$ represents a hydrogen atom, methyl, ethyl, propyl, isopropyl, butyl, tert-butyl, a hydroxyl group, chlorine, bromine or fluorine; $R^{14}$ represents a hydrogen atom, methyl, ethyl, propyl, isopropyl, butyl, tert-butyl, trifluoromethyl, chlorine, bromine, fluorine, amino, methylamino, ethylamino, dimethylamino, diethylamino, nitro, hydroxymethyl, hydroxyethyl, hydroxypropyl, carbamoyl, N-methylcarbamoyl, N,N-dimethylcarbamoyl, N-ethylcarbamoyl, N,N-diethylcarbamoyl, methyloxycarbonyl, ethyloxycarbonyl, —COOH, methyloxycarbonylethyl, ethyloxycarbonylethyl, methyloxycarbonylmethyl, ethyloxycarbonylmethyl, hydroxycarbonylmethyl, hydroxycarbonylethyl, methoxy, ethoxy, acetyloxy, propionyloxy or a hydroxyl group; $R^{15}$ represents a hydrogen atom, methyl, ethyl, propyl, isopropyl, butyl, tert-butyl, methoxy, ethoxy, propyloxy, tert-butyloxy, a hydroxyl group, chlorine, bromine or fluorine; and $R^{16}$ represents a hydrogen atom, methyl, ethyl, propyl, isopropyl, butyl, tert-butyl, a hydroxyl group, amino or nitro.

More preferably, $R^9$ represents a hydrogen atom, methyl, ethyl, butyl, tert-butyl or trifluoromethyl; $R^{10}$ represents a hydrogen atom, methyl, ethyl, butyl, tert-butyl, fluorine, chlorine, ethyloxycarbonyl, methyloxycarbonylmethyl or hydroxycarbonylethyl; $R^{11}$ represents a hydrogen atom, methyl, ethyl, amino, trifluoromethyl or a hydroxyl group; $R^{12}$ represents a hydroxyl group; $R^{13}$ represents a hydrogen atom, methyl, chlorine or a hydroxyl group; $R^{14}$ represents a hydrogen atom, methyl, ethyl, trifluoromethyl, chlorine, fluorine, amino, methylamino, nitro, hydroxymethyl, carbamoyl, N,N-dimethylcarbamoyl, methyloxycarbonyl, —COOH, methoxy, acetyloxy or a hydroxyl group; $R^{15}$ represents a hydrogen atom, methyl, methoxy, chlorine, fluorine or a hydroxyl group; and $R^{16}$ represents a hydrogen atom, methyl, a hydroxyl group, amino or nitro.

The specific compound of the formula (I) or (II) is:
2-(3,5-dimethyl-1H-pyrazol-1-yl)-4-fluorophenol
2-(5-hydroxy-3-methyl-1H-pyrazol-1-yl)phenol
2-(5-methyl-3-(trifluoromethyl)-1H-pyrazol-1-yl)phenol
2-(3,5-bistrifluoromethyl)-1H-pyrazol-1-yl)phenol
2-(3-methyl-1H-pyrazol-1-yl)phenol
2-(5-methyl-1H-pyrazol-1-yl)phenol
2-(3,4,5-trimethyl-1H-pyrazol-1-yl)phenol
2-(5-amino-3-tert-butyl-1H-pyrazol-1-yl)phenol
4-chloro-2-(3,5-dimethyl-1H-pyrazol-1-yl)phenol
2-chloro-6-(3,5-dimethyl-1H-pyrazol-1-yl)phenol
2-(4-chloro-3,5-dimethyl-1H-pyrazol-1-yl)phenol
2-(3,5-diethyl-1H-pyrazol-1-yl)phenol
3-(3,5-dimethyl-1H-pyrazol-1-yl)benzene-1,2-diol
2-(4-ethyl-3,5-dimethyl-1H-pyrazol-1-yl)phenol
5-fluoro-2-(3,4,5-trimethyl-1H-pyrazol-1-yl)phenol
4-fluoro-2-(3,4,5-trimethyl-1H-pyrazol-1-yl)phenol
2-(4-chloro-3,5-dimethyl-1H-pyrazol-1-yl)-5-fluorophenol
ethyl 1-(2-hydroxyphenyl)-3,5-dimethyl-1H-pyrazol-4-carboxylate
methyl 3-(1-(2-hydroxyphenyl)-3,5-dimethyl-1H-pyrazol-4-yl)propanoate
2-(4-butyl-3,5-dimethyl-1H-pyrazol-1-yl)phenol
2-(3,5-dimethyl-1H-pyrazol-1-yl)-5-fluorophenol
5-chloro-2-(3,5-dimethyl-1H-pyrazol-1-yl)phenol
2-(3,5-dimethyl-1H-pyrazol-1-yl)-3-nitrophenol
2-(3,5-dimethyl-1H-pyrazol-1-yl)-5-nitrophenol
3-(1-(2-hydroxyphenyl)-3,5-dimethyl-1H-pyrazol-4-yl)propionic acid
5-chloro-2-(3,4,5-trimethyl-1H-pyrazol-1-yl)phenol
5-amino-2-(3,5-dimethyl-1H-pyrazol-1-yl)phenol
5-nitro-2-(3,4,5-trimethyl-1H-pyrazol-1-yl)phenol
4-(3,5-dimethyl-1H-pyrazol-1-yl)benzene-1,3-diol
5-amino-2-(3,4,5-trimethyl-1H-pyrazol-1-yl)phenol
methyl 4-(3,5-dimethyl-1H-pyrazol-1-yl)-3-hydroxybenzene carboxylate
3-amino-2-(3,5-dimethyl-1H-pyrazol-1-yl)phenol
4-(3,5-dimethyl-1H-pyrazol-1-yl)-3-hydroxybenzene carboxylic acid
4-(3,5-dimethyl-1H-pyrazol-1-yl)-3-hydroxy-N,N-dimethyl benzamide
4-(3,5-dimethyl-1H-pyrazol-1-yl)-3-hydroxy benzamide
3-hydroxy-4-(3,4,5-trimethyl-1H-pyrazol-1-yl)benzene carboxylic acid
3-hydroxy-4-(3,4,5-trimethyl-1H-pyrazol-1-yl)benzamide
4-(4-chloro-3,5-dimethyl-1H-pyrazol-1-yl)-3-hydroxy benzamide
2-(3,5-dimethyl-1H-pyrazol-1-yl)benzene-1,3-diol
2-(3,5-dimethyl-1H-pyrazol-1-yl)-5-methylphenol
2-(3,5-dimethyl-1H-pyrazol-1-yl)-5-methoxyphenol
2-(3,5-dimethyl-1H-pyrazol-1-yl)-3-methylphenol
2-(3,5-dimethyl-1H-pyrazol-1-yl)-5-hydroxymethylphenol
2-(3,5-dimethyl-1H-pyrazol-1-yl)-5-methylaminophenol
2-(3,5-dimethyl-1H-pyrazol-1-yl)-4-methylphenol
2-(3,5-dimethyl-1H-pyrazol-1-yl)-5-trifluoromethylphenol
2-(3,5-dimethyl-1H-pyrazol-1-yl)-6-methylphenol
2-(3,5-dimethyl-1H-pyrazol-1-yl)-5-ethylphenol
2-(4-fluoro-3,5-dimethyl-1H-pyrazol-1-yl)phenol
5-bromo-2-(3,5-dimethyl-1H-pyrazol-1-yl)phenol
5-bromo-2-(4-chloro-3,5-dimethyl-1H-pyrazol-1-yl)phenol
5-bromo-2-(3,4,5-trimethyl-1H-pyrazol-1-yl)phenol
4-(3,5-dimethyl-1H-pyrazol-1-yl)-3-hydroxyphenyl acetate
4-(4-chloro-3,5-dimethyl-1H-pyrazol-1-yl)-3-hydroxyphenyl acetate
3-hydroxy-4-(3,4,5-trimethyl-1H-pyrazol-1-yl)phenyl acetate
2-(3,5-dimethyl-1H-pyrazol-1-yl)-4-methoxy-5-methylphenol
4-chloro-2-(3,5-dimethyl-1H-pyrazol-1-yl)-5-methylphenol
2-(3,5-dimethyl-1H-pyrazol-1-yl)-4,5-dimethylphenol or
4-(4-chloro-3,5-dimethyl-1H-pyrazol-1-yl)-benzene-1,3-diol
or a salt thereof.

Further, the specific compounds of the formula (II) in which $R^{14}$ is a hydrogen atom are:
2-(3,5-dimethyl-1H-pyrazol-1-yl)phenol
2-(3,5-dimethyl-1H-pyrazol-1-yl)-4-fluorophenol
2-(1H-pyrazol-1-yl)phenol
2-(5-hydroxy-3-methyl-1H-pyrazol-1-yl)phenol
2-(5-methyl-3-(trifluoromethyl)-1H-pyrazol-1-yl)phenol
2-(3,5-bistrifluoromethyl)-1H-pyrazol-1-yl)phenol
2-(3-methyl-1H-pyrazol-1-yl)phenol
2-(5-methyl-1H-pyrazol-1-yl)phenol
2-(3,4,5-Trimethyl-1H-pyrazol-1-yl)phenol
2-(5-amino-3-tert-butyl-1H-pyrazol-1-yl)phenol 4-chloro-2-(3,5-dimethyl-1H-pyrazol-1-yl)phenol
2-chloro-6-(3,5-dimethyl-1H-pyrazol-1-yl)phenol
2-(4-chloro-3,5-dimethyl-1H-pyrazol-1-yl)phenol
2-(3,5-diethyl-1H-pyrazol-1-yl)phenol
3-(3,5-dimethyl-1H-pyrazol-1-yl)benzene-1,2-diol
2-(3,5-dimethyl-1H-pyrazol-1-yl)benzene-1,4-diol
2-(4-ethyl-3,5-dimethyl-1H-pyrazol-1-yl)phenol
2-(4-chloro-3,5-dimethyl-1H-pyrazol-1-yl)benzene-1,4-diol
4-fluoro-2-(3,4,5-trimethyl-1H-pyrazol-1-yl)phenol
ethyl 1-(2-hydroxyphenyl)-3,5-dimethyl-1H-pyrazol-4-carboxylate
methyl 3-(1-(2-hydroxyphenyl)-3,5-dimethyl-1H-pyrazol-4-yl)propanoate
2-(4-butyl-3,5-dimethyl-1H-pyrazol-1-yl)phenol
2-(3,5-dimethyl-1H-pyrazol-1-yl)-3-nitrophenol
3-(1-(2-hydroxyphenyl)-3,5-dimethyl-1H-pyrazol-4-yl)propionic acid
3-amino-2-(3,5-dimethyl-1H-pyrazol-1-yl)phenol
2-(3,5-dimethyl-1H-pyrazol-1-yl)benzene-1,3-diol
2-(3,5-dimethyl-1H-pyrazol-1-yl)-3-methylphenol
2-(3,5-dimethyl-1H-pyrazol-1-yl)-4-methylphenol
2-(3,5-dimethyl-1H-pyrazol-1-yl)-6-methylphenol or
2-(4-fluoro-3,5-dimethyl-1H-pyrazol-1-yl)phenol,
or a salt thereof.

As an another embodiment, the present invention is an anti-fungal agent for tinea comprising a compound of anyone of the above (1) to (6) or a salt thereof. More preferably, the present invention is an anti-Trichophyton unguium agent comprising a compound of anyone of the above (1) to (6) or a salt thereof.

The compound of the present invention can take a form of a salt. Specifically, it can be used in the form of a pharmaceutically acceptable salt derived from an inorganic acid, an organic acid or a base. "Pharmaceutically acceptable salt" is publicly known in the art. For example, S. M. Berge et al. described a pharmaceutically acceptable salt in Journal of Pharmaceutical Sciences, 66 p. 1 and onward (1977) in detail. Representative acid addition salts include inorganic acid salts such as hydrochloride, sulfate, nitrate, hydrobromide, hydroiodide and phosphate; organic carboxylate such as acetate, trifluoroacetate, lactate, citrate, oxalate, succinate, glutarate, malate, tartrate, fumarate, mandelate, maleate, benzoate, nicotinate and phthalate; organic sulfonic acid salts such as methanesulfonate, ethanesulfonate, 2-hydroxyethanesulfonate, benzensulfonate, p-toluenesulfonate, 2-naphthalenesulfonate and camphor sulfonate; and acidic amino acid salts such as aspartate and glutamate, but not limited to these. Preferred examples of the acid addition salts include a salt with an inorganic acid such as hydrochloric acid, hydrobromic acid, sulfuric acid and phosphoric acid; or a salt with an organic acid such as oxalic acid, maleic acid, methanesulfonic acid, p-toluenesulfonic acid and citric acid. More preferred examples include a salt with hydrochloric acid, hydrobromic acid, sulfuric acid and methanesulfonic acid.

A base addition salt can be prepared in situ during the final isolation/purification process of the compound of the present invention by reacting a carboxylic acid or a phenolic hydroxyl group-containing moiety with a suitable base. Pharmaceutically acceptable salts include alkaline metal salts such as lithium salt, sodium salt and potassium salt; alkaline earth metal salts such as calcium salt and magnesium salt; aluminum salt and ammonium salt; also organic base salts such as methylamine salt, dimethylamine salt, ethylamine salt, diethylamine salt, trimethylamine salt, triethylamine salt, tetramethylammonium salt, tetraethylammonium salt, pyridine salt, picoline salt, ethanolamine salt, diethanolamine salt, triethanolamine salt, trishydroxymethylaminomethane salt, piperidine salt, piperazine salt, dicyclohexylamine salt and N,N-dibenzylethylenediamine salt; and basic amino acid salts such as arginine salt, lysine salt and ornithine salt, but not limited to these. Preferred examples of the base addition salts include addition salts with sodium, potassium, calcium, ethanolamine and trishydroxymethylamino methane. More preferred examples include addition salts with sodium, potassium and trishydroxymethylamino methane.

Furthermore, the present invention compound can be used in the form of solvate. As used herein, the term "solvate" refers to various stoichiometric complexes formed by a solute (a compound of formula (I) or formula (II) of the present invention or a salt thereof) and a solvent. The solvent for the object of the present invention preferably is a solvent which does not inhibit the biological activity of the solute and is pharmaceutically acceptable. Examples of suitable solvents include water, methanol, ethanol, ethylene glycol, propylene glycol, ethyl acetate and butyl acetate, but not limited to these. Preferred examples of the solvent for the solvate include water, ethanol and ethyl acetate.

The compound (I) or (II) of the present invention can be safely administered orally or parenterally according to a publicly known method as a pharmaceutical composition mixed with a pharmacologically acceptable carrier, for example, as a tablet (including sugar-coated tablet and film-coated tablet), powder, granule, capsule, (including soft capsule), liquid, injection, suppository, controlled release tablet, lotion, liniment, poultice, ointment, patch, spirit, suspension agent, emulsion, transdermally delivered pharmaceutical preparations, liquid, cream, aerosol and nail lacquer agent.

As the pharmacologically acceptable carrier which may be used for the preparation of the pharmaceutical preparation of the present invention, various organic or inorganic carrier substances commonly used as a material for pharmaceutical preparations can be mentioned including, for example, excipients, lubricants, binders, disintegrators for solid pharmaceutical preparations; and solvents, solubilizing agents, suspending agents, isotonizing agents, buffering agents, soothing agent for liquid pharmaceutical preparations. In addition, additives such as ordinary preservatives, antioxidants, colorants, sweeteners, absorbents and wetting agents can be added as necessary.

As the excipient, for example, lactose, white sugar, D-mannitol, starch, cornstarch, crystals cellulose and light anhydrous silicic acid can be mentioned.

As the lubricant, for example, stearic acid magnesium, stearic acid calcium, talc and colloidal silica can be mentioned.

As the binder, for example, crystals cellulose, white sugar, D-mannitol, dextrin, hydroxypropylcellulose, hydroxypropylmethylcellulose, polyvinylpyrrolidone, starch, sucrose, gelatin, methylcellulose and carboxymethylcellulose sodium can be mentioned.

As the disintegrator, for example, starch, carboxymethylcellulose, carboxymethylcellulose calcium, croscarmellose sodium, sodium carboxymethyl starch and L-hydroxypropylcellulose can be mentioned.

As the solvent, for example, injection water, alcohol, propylene glycol, macrogol, sesame oil, corn oil and olive oil can be mentioned.

As the solubilizing agent, for example, polyethylene glycol, propylene glycol, D-mannitol, benzyl benzoate, ethanol, trisamino methane, cholesterol, triethanolamine, sodium carbonate and citric acid sodium can be mentioned.

As the suspending agent, for example, a surfactant such as stearyltriethanolamine, sodium lauryl sulfate, lauryl aminopropionic acid, lecithin, benzalkonium chloride, benzethonium chloride and glyceryl mono stearate; and hydrophilic macromolecules, for example, polyvinyl alcohol, polyvinylpyrrolidone, carboxymethylcellulose sodium, methylcellulose, hydroxymethylcellulose, hydroxyethyl cellulose and hydroxypropylcellulose can be mentioned.

As the isotonizing agent, for example, glucose, D-sorbitol, sodium chloride, glycerol and D-mannitol can be mentioned.

As the buffering agent, for example, buffer solutions of phosphate, acetate, carbonate and citrate can be mentioned.

As the soothing agent, for example, benzyl alcohol can be mentioned.

As the preservative, for example, p-hydroxybenzoate esters, chlorobutanol, benzyl alcohol, phenethyl alcohol, dehydroacetic acid and sorbic acid can be mentioned.

As the antioxidants, for example, sulfite, ascorbic acid and α-tocopheryl can be mentioned.

The present invention is preferably an agent for topical use, and any dosage form used for topical pharmaceutical compositions can be employed without any particular limitations, including lotion, liniment, poultice, ointment, patch, spirit, suspension agent, emulsion, transdermally delivered pharmaceutical preparation, liquid, cream, aerosol and nail lacquer agent. Particularly preferred are nail lacquer agent, lotion, liquid, cream, patch and the like.

The topical anti-fungal agent for tinea of the present invention can contain any components commonly used for pharmaceutical compositions within the scope not impairing the effect of the present invention. Such components include, for example, hydrocarbons such as vaseline and microcrystalline wax; esters such as jojoba oil, spermaceti wax, triacetin, triethyl citrate and butyl acetate; triglycerides such as beef tallow and olive oil; higher alcohols such as cetanol and oleyl alcohol; fatty acids such as stearic acid and oleic acid; alcohols such as ethanol and isopropanol; polyalcohols such as glycerol and 1,3-butane diol; water, nonionic surfactants, anionic surfactants, cationic surfactants, amphoteric surfactants, polyvinylpyrrolidone, thickeners such as Carbopol, preservatives, ultraviolet absorbers, antioxidants, pigments and powders.

The topical pharmaceutical composition of the present invention can be prepared by treating any of these components with the compound of the formula (I) or (II) in accordance with the conventional method.

The content of compound (I) or (II) in the pharmaceutical preparation of the present invention is approximately 0.01 to 100 wt % based on the total pharmaceutical preparation.

While the dosage amount varies depending on the subject of administration, administration route, disease, etc., when administered, for example, to adults as a topical anti-fungal agent for tinea, the active ingredient compound (I) or (II) can be administered in the amount of 0.5-15% as single or divided daily doses. Or, the active ingredient can be administered once per 2 to 7 days.

It is preferred that the administration be made on a daily basis. In particular, since the present invention has a high permeability for tinea unguium, it is possible to remarkably transfer the active ingredient into nails, compared with conventional topical agents, whereby it is possible to treat tinea unguium only by the topical agent without taking oral anti-fungal agents for a long term. Although recurrence and reinfection are serious concerns about tinea unguium, such recurrence and reinfection can be prevented by administering the topical anti-fungal agent for tinea of the present invention for one to two weeks after the condition subsides. The topical anti-fungal agent for tinea of the present invention achieves preventive effects in this manner.

Effects of the Invention

An anti-fungal agent for tinea having a strong anti-Trichophyton activity is now provided. In addition, since the compound of the present invention has a remarkable effect with regard to nail permeability, a topical tinea unguium agent useful to tinea unguium, which used to be difficult to treat, is now provided.

Thereby, drug interactions, hepatic disorders and side effects by prolonged administration, which remain to be big concerns for conventional oral antifungal agents, can be avoided, and treatment of elderly people and patients with diabetes who suffer from tinea unguium or the like and often take a number of medicines is now possible.

EMBODIMENT TO CARRY OUT THE INVENTION

Formula (I) and formula (II) of the present invention or a salt thereof can be obtained, for example, by the process shown by the following reaction formula or a similar process. The preparation process is shown in the scheme below, in which each description of the compound has the same meaning as stated above. Further, the definitions of formula (II) are the same as those of formula (I) except for a part of the definitions of the substituents, and formula (II) can be prepared in an analogous manner to formula (I), so that an explanation will be given using formula (I) in this section.

2-(1H-pyrazol-1-yl)phenol derivative represented by general formula (I) can be synthesized using the process shown in Scheme 1. In Scheme 1, P and P' represent hydrogen or a suitable protecting group; X represents halogen or a suitable boronic acid group; and Y represents a dissociated ion of the acid used in the reaction. As used herein, "suitable boronic acid" refers to a boronic acid or a boronic acid ester.

[Chemical formula 4]

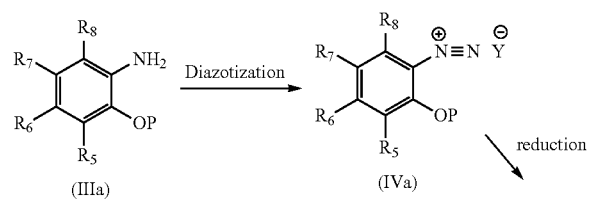

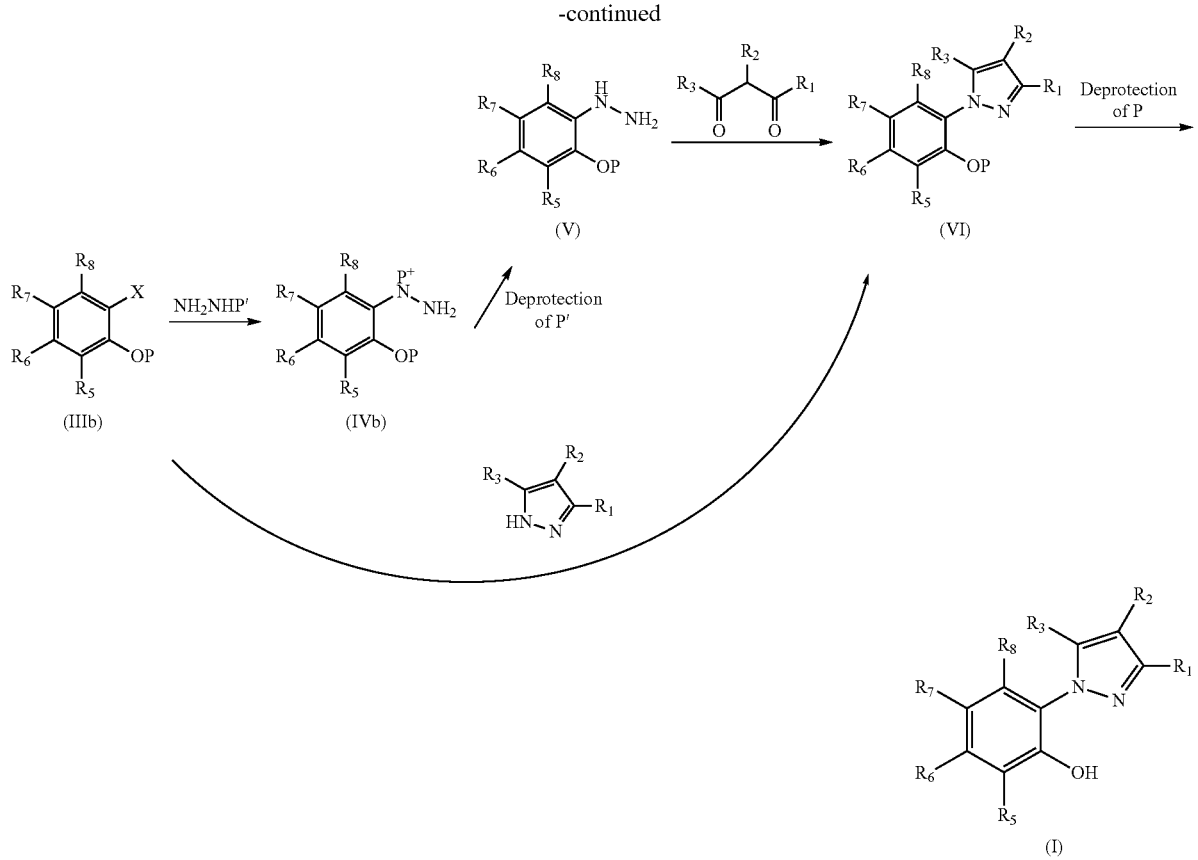

The process for obtaining a hydrazine derivative (V) or a salt thereof from 2-hydroxy aniline derivative (IIIa) or a salt thereof via diazonium compound (IVa) can be carried out in accordance with the process described in Organic Synthesis Collective Volume 1, pp. 442-445, J. Org. Chem., Vol. 21, pp. 394-399, 1956, WO2007/083320 and U.S. Pat. No. 6,852,890.

The diazotization reaction can be carried out using a nitrite such as potassium nitrite, calcium nitrite, silver nitrite, sodium nitrite and barium nitrite, nitrosylsulfuric acid, or a nitrite ester such as ethyl nitrite, isoamyl nitrite, isobutyl nitrite, isopropyl nitrite, tert-butyl nitrite, n-butyl nitrite and n-propyl nitrite. Preferred examples include sodium nitrite and nitrite esters such as isoamyl nitrite and tert-butyl nitrite.

When a protecting group is used, any group can be used as long as it is inert in the steps other than deprotection, and as P and P' for example, an alkyl group such as methyl group, isopropyl group, allyl group, tert-butyl group, methoxymethyl group, methylthiomethyl group, benzyl group and 9-anthrylmethyl group; an acyl group such as pivaloyl group and benzoyl group; or a sulfonyl group such as p-toluene sulfonyl group and methanesulfonyl group can be used, but not limited to these. Preferred protecting groups include methyl group, p-toluene sulfonyl group and methanesulfonyl group.

The amount of the reagent used in the diazotization reaction is preferably 1 to 10 equivalents, and more preferably 1 to 3 equivalents with respect to 2-hydroxy aniline derivative (IIIa).

In the above-mentioned diazotization reaction, when nitrite is used, water and an organic solvent mixed with water in any ratio, for example, methanol, ethanol, 2-propanol, acetic acid, trifluoroacetic acid, tetrahydrofuran, 1,4-dioxane, dimethylformamide and dimethyl sulfoxide, can be used. Further, a plurality of these solvents can be mixed and used. Preferred examples include water, a water-methanol mixture and a water-methanol-acetic acid mixture. Further, in order to assure the solubility of the aniline derivative, which is a substrate, and to generate a nitrous acid in the reaction system, the diazotization reaction is carried out under the acidic condition. As the acid to be used, hydrochloric acid, hydrobromic acid, sulfuric acid, nitric acid, acetic acid, trifluoroacetic acid and phosphoric acid can be mentioned. Preferred examples include hydrochloric acid, acetic acid and trifluoroacetic acid. Further, these acids can also be used as a solvent at the same time.

In the diazotization reaction, when nitrite ester is used, alcohols such as methanol, ethanol, methoxyethanol, ethoxyethanol, 1-propanol, 2-propanol, 1-butanol, 2-butanol and 2-methyl-2-propanol; ether-based solvents such as diethyl ether, diisopropyl ether, tetrahydrofuran, methyl-tert-butyl ether, diphenyl ether and 1,4-dioxane; acetate esters such as methyl acetate, ethyl acetate, propyl acetate and butyl acetate; aprotic solvents such as N,N-dimethylformamide, N,N-dimethylacetamide, N-methylpyrrolidone and dimethylsulfoxide; and halogen-based solvent such as dichloromethane, chloroform and 1,2-dichloroethane can be used. Further, a plurality of these solvents can be mixed and used. Preferably, it is methanol, ethanol and a mixture of ethanol-diethyl ether.

The temperature of the diazotization reaction, when either nitrite or nitrite ester is used, is preferably −50° C. to 50° C., and more preferably −30° C. to 10° C. Even more preferably, it is between −10° C. and 5° C.

The diazotization reaction often completes in 5 minutes to 12 hours, and normally in 3 hours or less, although the time varies depending on the substrate and reaction conditions.

The concentration of the substrate in the diazotization reaction liquid is not particularly limited, but can be in the range of 0.1 mM to 10 M. Preferably, it is in the range of 1 mM to 1 M.

For the reduction from the diazonium compound (IVa) to the hydrazine derivative (V), stannous chloride or a hydrate thereof, sulfite, bisulfite salt, dithionite or triphenyl phosphine can be used (Organic Synthesis Collective, Volume 1, pp. 442-445, J. Org. Chem., vol. 21, pp. 394-399, 1956, WO2007/083320, U.S. Pat. No. 6,852,890, US2007/0105866, J. Am. Chem. Soc., vol. 92, pp. 853-859, 1970). Preferred is a process in which stannous chloride, dithionite or sulfite is used.

The reduction reaction can be carried out following the diazotization reaction. That is, without isolating a generally unstable diazonium compound, it is possible to synthesize a hydrazine derivative (V) or a salt thereof by adding a reduction reagent in the reaction liquid, or by adding the diazotization reaction liquid in a solution of a reduction reagent.

The amount of the reducing agent is preferably 1 to 30 equivalents, and more preferably 1 to 10 equivalents with respect to the corresponding diazonium compound.

The solvent used in the reduction reaction may be the same as the solvent used in the diazotization reaction, and the solvent can be added as necessary, but the solvent is preferably the same as the one used in the diazotization reaction.

While the temperature of the reduction reaction varies depending on the type of the reducing agent, it is preferably −50° C. to 120° C., and more preferably −10° C. to 70° C. Even more preferably, it is between −10° C. and 30° C.

The hydrazine derivative (V) or a salt thereof can be synthesized from the compound (IIIb) not via the diazonium compound (IVa). That is, the hydrazine derivative (V) or a salt thereof can be obtained by reacting the compound (IIIb) with a hydrazine or a hydrazine protected with P' in the presence or absence of a suitable catalyst.

The phenylpyrazol derivative (VI) can also be synthesized in an analogous manner by reacting the compound (IIIb) with a suitable pyrazol in the presence or absence of a suitable catalyst.

When hydrazine bound with a protecting group P' is used, any group can be used as long as it is inert in the steps other than deprotection, and as P', for example, an alkyloxycarbonyl group such as methoxy carbonyl group, ethoxy carbonyl group, tert-butoxy carbonyl group, and benzyloxy carbonyl group, or an acyl group such as pivaloyl group and benzoyl group, or a sulfonyl group such as p-toluene sulfonyl group and methanesulfonyl group can be mentioned, but not limited to these. As a preferable protecting group, t-butoxy carbonyl group can be mentioned.

When X of the compound (IIIb) is halogen, the reaction can be carried out in accordance with the process described in Organic Letters Vol. 3, pp. 3803-3805, 2001 J. Org. Chem., vol. 72, pp. 6190-6199, 2007 and J. Org. Chem., vol. 70, pp. 5164-5173, 2005. When X of the compound (IIIb) is boronic acid, the reaction can be carried out in accordance with the process described in Bioorg. Med. Chem. Lett. vol. 18, pp. 4438-4441, 2008.

The amount of a hydrazine or a hydrazine protected with P' or pyrazol used in the above reaction is preferably 1 to 30 equivalents and more preferably 1 to 5 equivalents with respect to the compound (IIIb).

While the solvent suitable for the reaction varies depending on the substrate and the reaction conditions, aprotic solvents such as N,N-dimethylformamide, N,N-dimethyl acetamide, N-methylpyrrolidone, dimethyl sulfoxide, sulfolane, acetonitrile and propionitrile; ether-based solvents such as 1,4-dioxane, 1,2-dimethoxyethane and 1,2-diethoxyethane; and halogen-based solvents such as chloroform, 1,2-dichloroethane, 1,1,2,2-tetrachloroethane and 1,1,1-trichloroethane can be mentioned, but not limited to these. Further, a plurality of these solvents can be mixed and used. When the substrate is a liquid, it is possible to cause a reaction without using a solvent. It is preferred that a reaction be carried out using N,N-dimethylformamide, N-methylpyrrolidone, propionitrile or dimethyl sulfoxide, or with no solvent.

In the reaction, in addition to a salt of copper and palladium, a catalytic or stoichiometric amount or more of copper or palladium to which a suitable ligand is coordinated can be used. At that time, it is preferred that an organic base such as 1,4-diazabicyclo[2,2,2]octane, 1,8-diazabicyclo[5,4,0]undecene, pyridine and N,N-dimethylaminopyridine; or an inorganic base such as potassium tert-butoxide, sodium tert-butoxide or potassium carbonate, cesium carbonate and potassium phosphate are used. Pyridine, potassium carbonate, cesium carbonate and potassium phosphate are more preferable.

As a suitable ligand, tributylphosphine, triphenylphosphine, N-methylglycine, N,N-dimethylglycine, 1,2-diaminocyclohexane, 1,10-phenanthroline derivative, 8-hydroxy quinolin, picolinic acid and 2,2'-bipyridine can be mentioned, but not limited to these. N,N-dimethyl glycine, 1,2-diaminocyclohexane and 8-hydroxyquinolin are preferable.

Addition of a small amount of water or polyethylene glycol may help produce a favorable reaction result.

When X of the compound (Mb) is boronic acid, infusion of air or oxygen into a reaction system suitably may help produce a favorable reaction result.

While the temperature of the above reaction varies depending on the type of the substrate and catalyst and the presence or absence of catalyst, 10° C. to 200° C. is preferable, and 20° C. to 150° C. is more preferable. At this time, irradiation of microwaves may accelerate the reaction.

The reaction often completes in 15 minutes to 96 hours, and normally in 48 hour or less, although the time varies depending on the type of the substrate and catalyst and the presence or absence of catalyst.

While the concentration of the substrate in the reaction is not particularly limited, the reaction is usually carried out at a concentration of 1 mM to neat (solvent free). It is preferably 10 mM to 10 M.

For the deprotection reaction from the compound (IVb) to (V) or a salt thereof, a suitable process may be employed in accordance with the P' used referring to Green, Protective Groups in Organic Synthesis (5th), 1999, John Wieley & Sons. Specifically, when P' is a tert-butoxycarbonyl group, use of an acid such as hydrochloric acid or trifluoroacetic acid is preferable. At that time, coexistence of anisole or thioanisole may help produce a favorable result.

The resulting hydrazine derivative (V) or a salt thereof can synthesize, by reacting with 1,3-diketone or a chemical equivalent thereof, a phenylpyrazol derivative (VI) forming a pyrazol ring. Here, "chemical equivalent" refers to a compound like the one in which a carbonyl group is protected with an acetal group and which can easily be converted into a ketone group by an acid existing in the reaction system for forming a pyrazol ring.

The amount of 1,3-diketone or a chemical equivalent thereof used in the reaction is preferably 1 to 20 equivalents and more preferably 1 to 5 equivalents with respect to the compound (V).

While the solvent suitable for the reaction varies depending on the substrate and reaction conditions, alcohols such as methanol, ethanol, methoxyethanol, ethoxyethanol, 1-propanol, 2-propanol, 1-butanol, 2-butanol, 2-methyl-2-propanol, glycerol and 1,3-propanediol; ether-based solvents such as diethyl ether, diisopropyl ether, tetrahydrofuran, methyl-tert-butyl ether, diphenyl ether, 1,4-dioxane, diethylene glycol dimethyl ether, 1,2-dimethoxyethane and 1,2-diethoxyethane; acetate esters such as methyl acetate, ethyl acetate, propyl acetate and butyl acetate; aprotic solvents such as N,N-dimethylformamide, N,N-dimethylacetamide, N-methylpyrrolidone, dimethyl sulfoxide, acetonitrile and propionitrile; and halogen-based solvents such as dichloromethane, chloroform, 1,2-dichloroethane, 1,1,2,2-tetrachloroethane and 1,1,1-trichloroethane can be mentioned, but not limited to these. Further, a plurality of these solvents can be mixed and used. It is preferred that methanol, ethanol, 2-propanol, 1,2-dimethoxyethane and N,N-dimethylformamide be used.

When the hydrazine derivative (V) is used in a free form in the reaction, a catalytic amount or one equivalent or more of a suitable acid can be added.

Examples of the suitable acid include hydrochloric acid, hydrobromic acid, sulfuric acid, nitric acid, acetic acid, trifluoroacetic acid and phosphoric acid. Preferred examples include hydrochloric acid and trifluoroacetic acid.

While the temperature of the reaction varies depending on the type of the substrate, it is preferably 10° C. to 200° C., and more preferably 40° C. to 120° C.

The reaction often completes in 15 minutes to 24 hours, and normally in 12 hours or less, although the time varies depending on the type of the substrate.

While the concentration of the substrate in the reaction is not particularly limited, the reaction is usually carried out at the concentration of 0.1 mM to 1 M. It is preferably 10 mM to 1 M.

The resulting phenylpyrazol derivative (VI) can lead to the compound (I) of the present invention by deprotection, if necessary, of the protecting group. For the deprotection reaction, a suitable process in accordance with the P used may be used referring to Green, Protective Groups in Organic Synthesis (5th), 1999, John Wieley & Sons. When P is a methyl group, boron tribromide, aluminium chloride or the like, when P is a benzyl group, a catalytic hydrogenation reduction or the like, and when P is a p-toluene sulfonyl group, sodium hydroxide or potassium hydroxide is preferably used.

It is possible to apply further chemical modification to the compound (I) of the present invention by a commonly-used organic chemical reaction to one or both of the benzene ring side chain or the pyrazol ring side chains. Reactions easily conceived by a person skilled in the art having knowledge of organic chemistry can be applied including esterification, amidation or reduction to an alcohol to a compound having a carboxyl group, and alkylation, acylation or carbamation to a compound having an amino group.

Furthermore, the compound (1) of the present invention can be synthesized, as shown in Scheme 2, using 2-nitroaniline derivative (IIIc) or nitrobenzene derivative (IIId) having halogen or a boronic acid group at 2-position. In Scheme 2, P' represents hydrogen or a suitable protecting group; X represents a halogen or a suitable boronic acid group; and Y represents a dissociated ion of the acid used in the reaction.

Scheme 2

[Chemical formula 5]

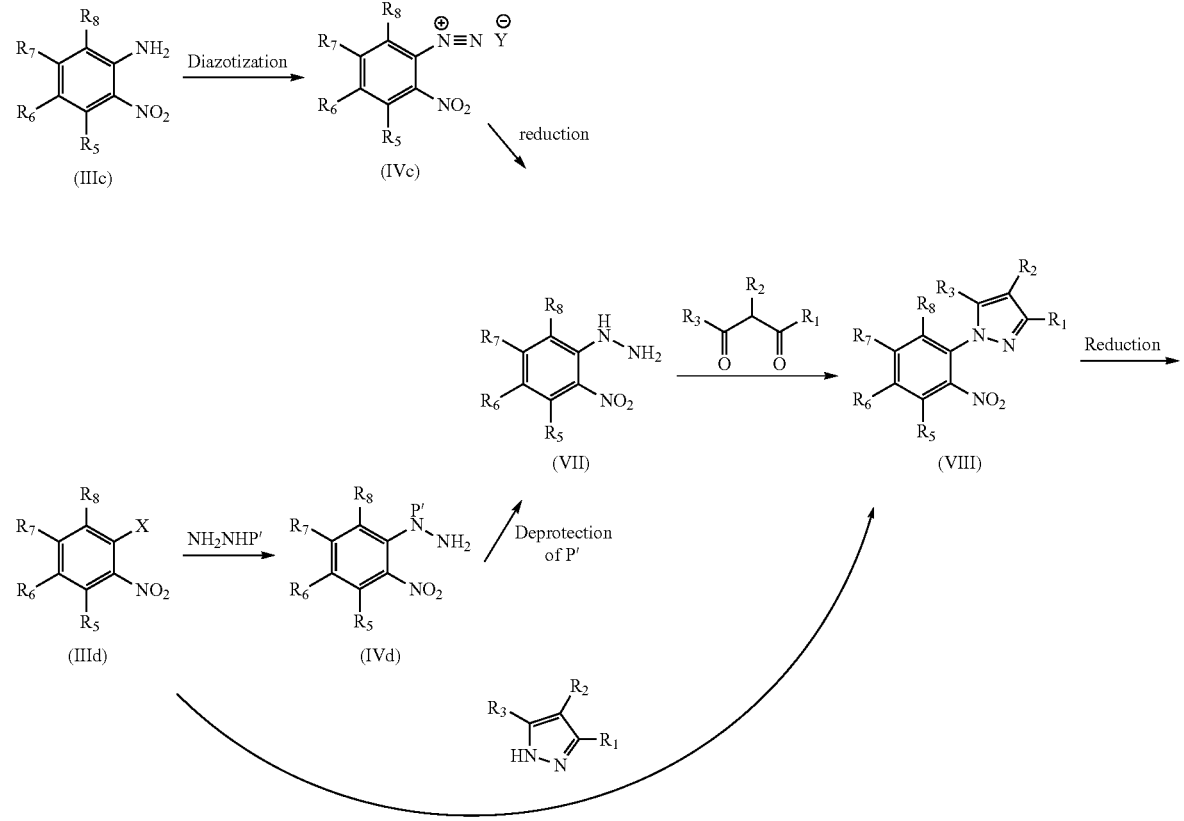

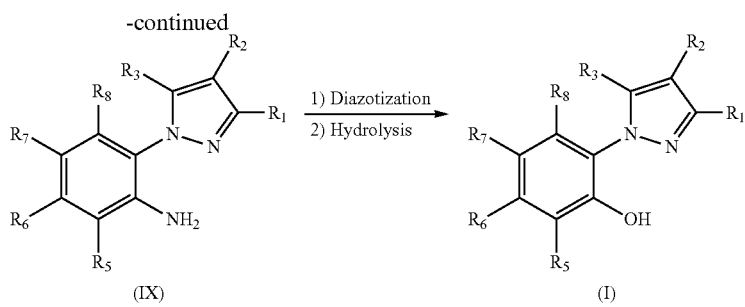

The diazotization of 2-nitroaniline derivative (IIIc), the reduction of the resulting diazonium compound, and the cyclization reaction of the pyrazol ring can be synthesized in accordance with the aforementioned preparation processes from (IIIa) to (V) and from (V) to (VI).

The reaction from the nitrobenzene derivative (IIId) to 2-nitrophenylpyrazol derivative (VIII) can be carried out in accordance with the aforementioned preparation process from (IIIb) to (VI), or can be carried out in accordance with the method described in J. Org. Chem., vol. 76, pp 654-660, 2011.

For the reduction from 2-nitrophenylpyrazol derivative (VIII) to 2-aminophenylpyrazol derivative (IX), a catalytic hydrogenation reduction, reduction by a metal or reduction by metal hydride in the presence of an acid, or the like can be used in reference to Experiment Chemical Lectures Version 4, pp. 159 to 266.

In the case of the catalytic hydrogenation reduction reaction, hydrogenation pressure is from 1 to 80 atmospheric pressures, and preferably 1 to 5 atmospheric pressures.

While the solvent suitable for the above-mentioned reaction varies depending on the substrate and reaction conditions, alcohols such as methanol, ethanol, methoxyethanol, ethoxyethanol, 1-propanol, 2-propanol, 1-butanol, 2-butanol and 2-methyl-2-propanol; ether-based solvents such as diethyl ether, diisopropyl ether, tetrahydrofuran, methyl-t-butyl ether, diphenyl ether, diethylene glycol dimethyl ether and 1,4-dioxane; acetic acid esters such as methyl acetate, ethyl acetate, propyl acetate and butyl acetate; N,N-dimethylformamide, N,N-dimethylacetamido, N-methylpyrrolidone, dimethyl sulfoxide, glycerol, 1,3-propanediol, 1,2-dimethoxyethane, 1,2-diethoxyethane, water and acetic acid can be mentioned, but not limited to these. Further, a plurality of these solvents can be mixed and used. It is preferable to use methanol, ethanol, 2-propanol and 1,2-dimethoxyethane.

As the catalyst used in the catalytic hydrogenation reduction reaction, metals such as palladium, platinum, rhodium and nickel and complexes thereof, the compounds adsorbed to activated carbon thereof or a salt thereof are used. Preferred examples include palladium carbon and Raney Nickel.

While the temperature of the catalytic hydrogenation reduction reaction varies depending on the type of the substrate and catalyst, 0° C. to 100° C. is preferable, and 10° C. to 50° C. is more preferable.

The catalytic hydrogenation reduction reaction often completes in 15 minutes to 24 hours, and normally in 12 hour or less, while the time varies depending on the type of the substrate.

While the concentration of the substrate in the catalytic hydrogenation reduction reaction is not particularly limited, the reaction is usually carried out at a concentration of 0.1 mM to 1 M. It is preferably 1 mM to 100 mM.

When a metal is used as a reducing agent, used metals include iron, tin and zinc, and it is necessary to add an a acid together. As the acid, hydrochloric acid, sulfuric acid, acetic acid, trifluoroacetic acid and phosphoric acid can be used, and hydrochloric acid is preferable. Further, these acids can also be used as a solvent at the same time.

The amount of metal used in the reaction is preferably 1 to 100 equivalents and more preferably 3 to 15 equivalents with respect to compound (VIII).

While the solvent suitable for the reaction varies depending on the substrate and reaction conditions, water, acetic acid, alcohols such as methanol, ethanol, methoxyethanol, ethoxyethanol, 1-propanol, 2-propanol, 1-butanol, 2-butanol and 2-methyl-2-propanol; ether-based solvents such as diethyl ether, diisopropyl ether, tetrahydrofuran, diphenyl ether, diethylene glycol dimethyl ether and 1,4-dioxane; acetate esters such as methyl acetate, ethyl acetate, propyl acetate and butyl acetate, N,N-dimethylformamide, N,N-dimethylacetamido, N-methylpyrrolidone, dimethyl sulfoxide, glycerol, 1,3-propanediol, 1,2-dimethoxyethane and 1,2-diethoxyethane can be mentioned, but not limited to these. Further, a plurality of these solvents can be mixed and used. It is preferred that hydrochloric acid, acetic acid, ethanol, 2-propanol and a mixture of these are used.

While the temperature of the reaction varies depending on the type of the substrate and conditions, it is preferably 0° C. to 100° C., and more preferably 20° C. to 50° C.

The reaction often completes in 1 hour to 24 hours, and normally in 12 hours or less, although the time varies depending on the type of the substrate and conditions.

While the concentration of the substrate in the reaction is not particularly limited, the reaction is usually carried out at a concentration of 0.1 mM to 1 M. It is preferably 1 mM to 100 mM.

In the case of reduction reaction using a metal hydride, as a reagent, lithium borohydride, sodium borohydride, potassium borohydride, zinc borohydride, lithium triethoxy borane and diisobutylaluminium hydride are used, and it is preferably lithium borohydride or sodium borohydride. At that time, coexistence of stannous chloride, nickel chloride(II) or the like may help produce a favorable result.

The amount of the reducing agent used in the reaction is preferably 1 to 50 equivalents, and more preferably 1 to 5 equivalents with respect to compound (VIII).

While the solvent suitable for the reaction varies depending on the type of the substrate and reducing agent, ether-based solvents such as diethyl ether, diisopropyl ether, tetrahydrofuran, diphenyl ether, 1,4-dioxane, diethylene glycol dimethyl ether, 1,2-dimethoxyethane and 1,2-diethoxyethane; and alcohols such as methanol, ethanol, methoxyethanol, ethoxyethanol, 1-propanol, 2-propanol, 1-butanol, 2-butanol and 2-methyl-2-propanol can be mentioned, but not limited to these. Further, a plurality of these solvents can be mixed and used. Preferred examples include methanol and a mixture of methanol and diethylene glycol dimethyl ether.

While the temperature of the reaction varies depending on the type of the substrate and conditions, it is preferably −80° C. to 100° C., and more preferably −20° C. to 80° C.

The reaction often completes in 15 minutes to 24 hours, and normally in 12 hours or less, although the time varies depending on the type of the substrate and conditions.

While the concentration of the substrate in the reaction is not particularly limited, the reaction is usually carried out at a concentration of 0.1 mM to 1 M. It is preferably 1 mM to 100 mM.

The resulting 2-aminophenylpyrazol derivative (IX) can be diazotized in accordance with the preparation process from the aforementioned (Ma) to (IVa) and Japanese Laid-open (Kokai) Patent Publication No. Hei 8-53401.

The reaction from diazonium compound to (I) can be carried out in accordance with the processes disclosed in Japanese Laid-open (Kokai) Patent Publication No. Hei 8-188545 and Japanese Laid-open (Kokai) Patent Publication No. Hei 11-60528.

The hydrolysis of the diazonium salt can be carried out by heating in water or a solvent containing water under the acidic conditions.

While the solvent suitable for the reaction varies depending on the substrate and reaction conditions, water, acetic acid, trifluoroacetic acid, alcohols such as methanol, ethanol, methoxyethanol, ethoxyethanol, glycerol, 1,3-propanediol, 1-propanol, 2-propanol, 1-butanol, 2-butanol and 2-methyl-2-propanol; ether-based solvents such as tetrahydrofuran, diethylene glycol dimethyl ether, 1,2-dimethoxyethane, 1,2-diethoxyethane and 1,4-dioxane; and aprotic solvents such as N,N-dimethylformamide, N,N-dimethylacetamide, N-methylpyrrolidone and dimethyl sulfoxide can be mentioned, but not limited to these. Further, a plurality of these solvents can be mixed and used. It is preferred that water, sulfuric acid, hydrochloric acid, trifluoroacetic acid, acetic acid, methanol, ethanol and any mixture of these is used.

While the temperature of the reaction varies depending on the type of the substrate and conditions, 20° C. to 200° C. is preferable, and 50° C. to 150° C. is more preferable.

The reaction often completes in 10 minutes to 24 hours, and normally in 12 hour or less, although the time varies depending on the type of the substrate and conditions.

While the concentration of the substrate in the reaction is not particularly limited, the reaction is usually carried out at a concentration of 0.1 mM to 1 M. It is preferably 1 mM to 100 mM.

Now the evaluation process will be described.
(1) Measurement of Antifungal Activity Measurement of antifungal activity was conducted by the following method.

The compounds for evaluation were dissolved in dimethyl sulfoxide (DMSO) and used. As the test medium, RPMI1640 medium containing 0.165 M 3-morpholino propane sulfonic acid (MOPS) was used. As the test strain, *T. mentagrophytes* ATCC18748 or *T. rubrum* ATCC10218 was used. 100 μL of the test strain each at a concentration of $1 \times 10^4$ conidia/mL was dispensed, mixed with compounds for evaluation on 96 well half area plate so that the concentration of DMSO becomes 1%, and cultured at 28° C. for 3 days (for *T. mentagrophytes*) or for 4 days (for *T. rubrum*). Then, 5 μL of Cell Counting Kit8 (WST8) was added and the absorbances at 450 nm and 595 nm was measured as background. Subsequently, they were incubated at 28° C. for 5 hours (for *T. mentagrophytes*) or overnight (for *T. rubrum*) to color, and again the absorbances at 450 nm and 595 nm was measured, and then calculated the growth inhibition percentages using the differences from the background, and 80% growth inhibition concentration was regarded as MIC (μg/ml).

(2) Nail Permeability Test

Compounds for evaluation were each dissolved in a solution of ethyl acetate:propylene glycol (1:1) or dimethyl sulfoxide at a concentration of 10 mg/mL. 2 μL each of the solutions was added to a bovine hoof slice placed on a low-melting-point agarose. After incubation at 28° C. for 5 days, the agaroses were collected, distilled water was added thereto, and the mixtures were heated and dissolved. The concentrations of the compound in the solutions were determined using a high performance liquid chromatography/mass spectrometry apparatus to obtain the amounts of the agents permeated through the hoof and to calculate the permeabilities of the respective agents.

Since the permeability of bovine hoof and human nail correlates as described in J. Pharma. Pharmacol., vol. 49, pp. 866-872, 1997, the nail permeability test was conducted using a bovine hoof in the present invention.

Nail permeability can also be confirmed using the method described below.

The compounds for evaluation were dissolved in a solution of ethyl acetate:propylene glycol (1:1) at a concentration of 50 mg/ml, 20 μL of which was added to the donor side (nail plate side) of Franz cell into which human nails were set, and they were left standing at 37° C. for 6 days and more in the incubator. After being left standing for 6 days and 10 days, the receptor solutions were sampled from the receptor chamber (phosphate buffer; pH 7.4), and the amount of eluted compounds were determined using high performance liquid chromatography/mass spectrometry apparatus.

EXAMPLES

The present invention will be explained in detail by way of Examples, but these working examples are mere examples, and not limit the present invention. "Room temperature" in Examples refers usually to about 1° C. to about 40° C.

Example 1

2-(3,5-Dimethyl-1H-pyrazol-1-yl)phenol a) 1-(2-Methoxyphenyl)-3,5-dimethyl-1H-pyrazol 3.50 g of 2-methoxyphenyl hydrazine hydrochloride was dissolved in 60 ml of ethanol, and 2.06 ml of acetyl acetone was added and heated at reflux for 1 hour. To the reaction mixture was added 150 ml of water, neutralized with saturated aqueous solution of sodium carbonate, and extracted with 150 ml of ethyl acetate. The organic layer was dried over anhydrous magnesium sulfate, and then the solvent was distilled off under reduced pressure and purified by silica gel column chromatography (n-hexane:ethyl acetate=2:1) to yield 3.88 g of the title compound.

$^1$H-NMR (CDCl$_3$); δ (ppm) 2.08 (3H, s), 2.29 (3H, s), 3.78 (3H, s), 5.95 (1H, s), 6.98-7.03 (2H, m), 7.29-7.32 (1H, m), 7.34-7.39 (1H, m).

MS (ESI); m/z 203 (M+H)$^+$ b) 2-(3,5-Dimethyl-1H-pyrazol-1-yl)phenol 3.88 g of 1-(2-methoxyphenyl)-3,5-dimethyl-1H-pyrazol was dissolved in 40 ml of methylene chloride, and 32 ml of 1 M solution of borontribromide in methylene chloride was added and stirred at room temperature for 1.5 hours. The reaction mixture was added to 150 ml of water, neutralized with 1N-sodium hydroxide and extracted with 150 ml of ethyl acetate. The organic layer was dried over anhydrous magnesium sulfate, and then the solvent was distilled off under reduced pressure, and purified by silica gel column chromatography (hexane:ethyl acetate=3:1) to yield 2.83 g of the title compound.

$^1$H-NMR (CDCl$_3$); δ (ppm) 2.29 (3H, s), 2.38 (3H, s), 6.02 (1H, s), 6.87-6.91 (1H, m), 7.06-7.09 (1H, m), 7.16-7.20 (1H, m).

MS (ESI); m/z 189 (M+H)$^+$

Example 2

2-(3,5-Dimethyl-1H-pyrazol-1-yl)-4-fluorophenol a) 2-Amino-4-fluorophenol 300 mg of 4-fluoro-2-nitrophenol was dissolved in 3 ml of ethanol, and 120 mg of 10% palladium/carbon was added and stirred under hydrogen atmosphere at room temperature for 1 hour. After the insoluble matter was filtered off, the filtrate was distilled off under reduced pressure to yield 211 mg of the title compound.

$^1$H-NMR (DMSO-d6); δ (ppm) 4.80 (2H, s), 6.09-6.14 (1H, m), 6.34-6.37 (1H, m), 6.53-6.57 (1H, m), 8.93 (1H, s).

MS (FAB); m/z 128 (M+H)$^+$ b) 2-(3,5-Dimethyl-1H-pyrazol-1-yl)-4-fluorophenol

To 100 mg of 2-amino-4-fluorophenol was added 0.8 ml of 5N-hydrochloric acid, and a solution in which 65 mg of sodium nitrite was dissolved in 0.2 ml of water was added dropwise at 0° C., and stirred for 30 minutes. Then, a solution in which 249 mg of stannous chloride was dissolved in 0.46 ml of 5N-hydrochloric acid, was added dropwise at 0° C., and stirred at 0° C. for 30 minutes and then at room temperature for 2 hours. The solvent was distilled off under reduced pressure, and 2.5 ml of ethanol and 81 μl of acetyl acetone were added, followed by heating at reflux for 4 hours. To the reaction mixture was added 50 ml of water, neutralized with a saturated solution of sodium hydrogen carbonate, and extracted with 50 ml of ethyl acetate. After the organic layer was dried over anhydrous magnesium sulfate, the solvent was distilled off under reduced pressure and purified by silica gel column chromatography (n-hexane:ethyl acetate=2:1) to yield 20.6 mg of the title compound.

$^1$H-NMR (CDCl$_3$); δ (ppm) 2.24 (3H, s), 2.33 (3H, s), 5.99 (1H, s), 6.82-6.90 (2H, m), 6.95-6.98 (1H, m).

MS (FAB); m/z 207 (M+H)$^+$

Example 3

2-(1H-Pyrazol-1-yl)phenol a) 1-(2-Methoxyphenyl)-1H-pyrazol 200 mg of 2-methoxyphenyl hydrazine hydrochloride was dissolved in 5 ml of ethanol, and 189 μl of malonaldehyde bisdimethylacetal was added and heated at reflux for 2 hours. To the reaction mixture was added 50 ml of water, neutralized with a saturated aqueous solution of sodium carbonate, and extracted with 60 ml of ethyl acetate. After the organic layer was dried over anhydrous magnesium sulfate, the solvent was distilled off under reduced pressure to yield 179.4 mg of the title compound.

$^1$H-NMR (CDCl$_3$); δ (ppm) 3.87 (3H, s), 6.42 (1H, d, J=2.4 Hz), 7.02-7.07 (2H, m), 7.27-7.32 (1H, m), 7.68-7.72 (2H, m), 8.01 (1H, d, J=2.4 Hz).

MS (FAB); m/z 175 (M+H)$^+$ b) 2-(1H-Pyrazol-1-yl)phenol 121 mg of the title compound was obtained from 178 mg of 1-(2-methoxyphenyl)-1H-pyrazol in an analogous manner to Example 1b).

$^1$H-NMR (CDCl$_3$); δ (ppm) 6.49 (1H, d, J=2.4 Hz), 6.88-6.92 (1H, m), 7.08-7.10 (1H, m), 7.14-7.18 (1H, m), 7.35-7.37 (1H, m), 7.72 (1H, s), 7.99 (1H, d, J=2.4 Hz).

MS (ESI); m/z 161 (M+H)$^+$

Example 4

2-(5-Hydroxy-3-methyl-1H-pyrazol-1-yl)phenol a) 5-Hydroxy-1-(2-methoxyphenyl)-3-methyl-1H-pyrazol 55.1 mg of the title compound was obtained from 150 mg of 2-methoxyphenyl hydrazine hydrochloride and 93 μl of methyl acetoacetate in an analogous manner to Example 1a).

$^1$H-NMR (CDCl$_3$); δ (ppm) 2.11 (3H, s), 3.76 (3H, s), 6.88-6.94 (3H, m), 7.19-7.34 (2H, m).

MS (ESI); m/z 204 (M+H)$^+$ b) 2-(5-Hydroxy-3-methyl-1H-pyrazol-1-yl)phenol 32.4 mg of the title compound was obtained from 52 mg of 5-Hydroxy-1-(2-methoxyphenyl)-3-methyl-1H-pyrazol in an analogous manner to Example 1b).

$^1$H-NMR (CDCl$_3$); δ (ppm) 2.17 (3H, s), 5.30 (1H, s), 6.88-6.95 (2H, m), 7.15 (1H, t, J=7.6 Hz), 7.37 (1H, d, J=7.6 Hz).

MS (FAB); m/z 191 (M+H)$^+$

Example 5

2-(5-Methyl-3-trifluoromethyl-1H-pyrazol-1-yl)phenol a) 1-(2-Methoxyphenyl)-5-methyl-3-trifluoromethyl)-1H-pyrazol 300 mg of 2-methoxyphenyl hydrazine hydrochloride was dissolved in 1.3 ml of 2-methoxyethanol, and 2.5 ml of acetic acid and 208 μl of 1,1,1-trifluoro-2,4-pentanedione were added and heated at reflux for 1 hour and 40 minutes. The solvent was distilled off under reduced pressure, and 50 ml of ethyl acetate was added, and the organic layer was washed with 50 ml of a saturated sodium bicarbonate solution and 50 ml of saturated saline and dried over anhydrous magnesium sulfate, and the solvent was distilled off under reduced pressure to yield 485.6 mg of the title compound.

$^1$H-NMR (CDCl$_3$); δ (ppm) 2.14 (3H, s), 3.78 (3H, s), 6.40 (1H, s), 7.00-7.07 (2H, m), 7.31-7.33 (1H, m), 7.41-7.45 (1H, m).

MS (ESI); m/z 257 (M+H)$^+$ b) 2-(5-Methyl-3-(trifluoromethyl)-1H-pyrazol-1-yl) phenol 320.1 mg of the title compound was obtained from 1-(2-methoxyphenyl)-5-methyl-3-(trifluoromethyl)-1H-pyrazol in an analogous manner to Example 1b).

¹H-NMR (CDCl₃); δ (ppm) 2.41 (3H, s), 6.52 (1H, s), 6.95-6.99 (1H, m), 7.11-7.13 (1H, m), 7.20-7.24 (1H, m), 7.28-7.32 (1H, m).
MS (FAB); m/z 243 (M+H)$^+$ Example 6

2-(3,5-Bistrifluoromethyl-1H-pyrazol-1-yl)phenol a) 1-(2-Methoxyphenyl)-3,5-bistrifluoromethyl)-1H-pyrazol The title compound was obtained from 300 mg of 2-methoxyphenyl hydrazine hydrochloride and 243 μl of hexafluoroacetyl acetone in an analogous manner to Example 5a).
¹H-NMR (CDCl₃); δ (ppm) 3.77 (3H, s), 7.01-7.06 (3H, m), 7.33 (1H, d, J=7.6 Hz), 7.49 (1H, d, J=7.6 Hz).
MS (ESI); m/z 311 (M+H)$^+$ b) 2-(3,5-Bistrifluoromethyl)-1H-pyrazol-1-yl)phenol 455.6 mg of the title compound was obtained from 1-(2-methoxyphenyl)-3,5-bistrifluoromethyl)-1H-pyrazol obtained in a) above in an analogous manner to Example 1b).
¹H-NMR (CDCl₃); δ (ppm) 6.99-7.04 (1H, m), 7.07-7.08 (1H, m), 7.10 (1H, s), 7.32-7.41 (2H, m).
MS (FAB); m/z 297 (M+H)$^+$ Example 7

2-(3-Methyl-1H-pyrazol-1-yl)phenol a) 1-(2-Methoxyphenyl)-3-methyl-1H-pyrazol 115.1 mg of the title compound was obtained from 200 mg of 2-methoxyphenyl hydrazine hydrochloride and 151 ml of 4,4-dimethoxybutan-2-one in an analogous manner to Example 1a).
¹H-NMR (CDCl₃); δ (ppm) 2.31 (3H, s), 3.80 (3H, s), 6.14 (1H, d, J=2.4 Hz), 6.95-6.99 (2H, m), 7.18-7.22 (1H, m), 7.61-7.63 (1H, m), 7.84 (1H, d, J=2.4 Hz).
MS (FAB); m/z 189 (M+H)$^+$ b) 2-(3-Methyl-1H-pyrazol-1-yl)phenol 76 mg of the title compound was obtained from 115 mg of 1-(2-methoxyphenyl)-3-methyl-1H-pyrazol in an analogous manner to Example 1b).
¹H-NMR (CDCl₃); δ (ppm) 2.36 (3H, s), 6.24 (1H, d, J=2.4 Hz), 6.85-6.89 (1H, m), 7.05-7.14 (2H, m), 7.29-7.31 (1H, m), 7.86 (1H, d, J=2.4 Hz).
MS (FAB); m/z 175 (M+H)$^+$ Example 8

2-(5-Methyl-1H-pyrazol-1-yl)phenol a) 1-(2-Methoxyphenyl)-5-methyl-1H-pyrazol 70 mg of the title compound was obtained from 200 mg of 2-methoxyphenyl hydrazine hydrochloride and 151 μl of 4,4-dimethoxybutan-2-one in an analogous manner to Example 1a).
¹H-NMR (CDCl₃); δ (ppm) 2.07 (3H, s), 3.71 (3H, s), 6.09 (1H, s), 6.94-6.99 (2H, m), 7.24-7.26 (1H, m), 7.31-7.35 (1H, m), 7.52 (1H, m).
MS (FAB); m/z 189 (M+H)$^+$ b) 2-(5-Methyl-1H-pyrazol-1-yl)phenol 45.5 mg of the title compound was obtained from 69 mg of 1-(2-methoxyphenyl)-5-methyl-1H-pyrazol in an analogous manner to Example 1b).
¹H-NMR (CDCl₃); δ (ppm) 2.41 (3H, s), 6.27 (1H, d, J=1.6 Hz), 6.90-6.94 (1H, m), 7.10-7.12 (1H, m), 7.19-7.24 (2H, m), 7.66 (1H, d, J=1.6 Hz).
MS (FAB); m/z 175 (M+H)$^+$ Example 9

2-(3,4,5-Trimethyl-1H-pyrazol-1-yl)phenol a) 1-(2-Methoxyphenyl)-3,4,5-trimethyl-1H-pyrazol 200 mg of 2-methoxyphenyl hydrazine hydrochloride was dissolved in 4 ml of ethanol, and 134 μl of 3-methyl-2,4-pentanedione was added and heated at reflux for 3 hours. To the reaction mixture was added 50 ml of water, neutralized with a saturated aqueous solution of sodium carbonate, and extracted with 60 ml of ethyl acetate. After the organic layer was dried over anhydrous magnesium sulfate, the solvent was distilled off under reduced pressure to yield 209.8 mg of the title compound.
¹H-NMR (CDCl₃); δ (ppm) 1.98 (3H, s), 2.02 (3H, s), 2.24 (3H, s), 3.80 (3H, s), 6.99-7.04 (2H, m), 7.29-7.31 (1H, m), 7.34-7.39 (1H, m).
MS (FAB); m/z 217 (M+H)$^+$ b) 2-(3,4,5-Trimethyl-1H-pyrazol-1-yl)phenol 104 mg of the title compound was obtained from 209 mg of 1-(2-methoxyphenyl)-3,4,5-trimethyl-1H-pyrazol in an analogous manner to Example 1b).
¹H-NMR (CDCl₃); δ (ppm) 1.99 (3H, s), 2.25 (3H, s), 2.31 (3H, s), 6.90 (1H, t, J=8.0 Hz), 7.08 (1H, d, J=8.0 Hz), 7.06-7.20 (2H, m), 9.89 (1H, s).
MS (ESI); m/z 203 (M+H)$^+$ Example 10

2-(5-Amino-3-tert-butyl-1H-pyrazol-1-yl)phenol a) 3-tert-Butyl-1-(2-methoxyphenyl)-1H-pyrazol-5-amine 310.3 mg of the title compound was obtained from 300 mg of 2-methoxyphenyl hydrazine hydrochloride, 215 mg of 4,4-dimethyl-3-oxopentanenitrile and 40 μl of acetic acid in an analogous manner to Example 1a).
¹H-NMR (CDCl₃); δ (ppm) 1.32 (9H, s), 3.80 (2H, s), 3.86 (3H, s), 5.51 (1H, s), 7.01-7.08 (2H, m), 7.30-7.35 (1H, m), 7.45-7.47 (1H, m).
MS (FAB); m/z 246 (M+H)$^+$ b) 2-(5-Amino-3-tert-butyl-1H-pyrazol-1-yl)phenol 66.2 mg of the title compound was obtained from 100 mg of 3-tert-butyl-1-(2-methoxyphenyl)-1H-pyrazol-5-amine in an analogous manner to Example 1b).
¹H-NMR (CDCl₃); δ (ppm) 1.30 (9H, s), 3.93 (2H, s), 5.55 (1H, s), 6.90 (1H, dt, J=1.6, 8.0 Hz), 7.08 (1H, dd, J=1.6, 8.0 Hz), 7.17 (1H, dt, J=1.6, 8.0 Hz), 7.47 (1H, dd, J=1.6, 8.0 Hz), 10.39 (1H, brs).
MS (FAB); m/z 232 (M+H)$^+$

Example 11

4-Chloro-2-(3,5-dimethyl-1H-pyrazol-1-yl)phenol a) 1-(5-Chloro-2-methoxyphenyl)-3,5-dimethyl-1H-pyrazol 104.8 mg of the title compound was obtained from 388 mg of 5-chloro-methoxyaniline hydrochloride in an analogous manner to Example 2b).

$^1$H-NMR (CDCl$_3$); δ (ppm) 2.11 (3H, s), 2.29 (3H, s), 3.79 (3H, s), 5.96 (1H, s), 6.93 (1H, dd, J=2.4, 7.2 Hz), 7.33-7.35 (2H, m).

MS (FAB); m/z 237 (M+H)$^+$ b) 4-Chloro-2-(3,5-Dimethyl-1H-pyrazol-1-yl)phenol 67.3 mg of the title compound was obtained from 104.8 mg of 1-(5-chloro-2-methoxyphenyl)-3,5-dimethyl-1H-pyrazol in an analogous manner to Example 1b).

$^1$H-NMR (CDCl$_3$); δ (ppm) 2.30 (3H, s), 2.43 (3H, s), 6.05 (1H, s), 7.02 (1H, d, J=8.8 Hz), 7.14-7.20 (2H, m), 10.08 (1H, s).

MS (FAB); m/z 223 (M+H)$^+$

Example 12

2-Chloro-6-(3,5-dimethyl-1H-pyrazol-1-yl)phenol a) 1-(3-Chloro-2-methoxyphenyl)-3,5-dimethyl-1H-pyrazol 30.6 mg of the title compound was obtained from 158 mg of 3-chloro-o-anisidine in an analogous manner to Example 2b).

$^1$H-NMR (CDCl$_3$); δ (ppm) 2.14 (3H, s), 2.29 (3H, s), 3.49 (3H, s), 5.99 (1H, s), 7.12 (1H, t, J=8.0 Hz), 7.27-7.31 (1H, m), 7.43-7.46 (1H, m).

MS (ESI); m/z 236 (M+H)$^+$ b) 2-Chloro-6-(3,5-dimethyl-1H-pyrazol-1-yl)phenol 27.4 mg of the title compound was obtained from 63.4 mg of 1-(3-chloro-2-methoxyphenyl)-3,5-dimethyl-1H-pyrazol in an analogous manner to Example 1b).

$^1$H-NMR (CDCl$_3$); δ (ppm) 2.30 (3H, s), 2.40 (3H, s), 6.05 (1H, s), 6.86 (1H, t, J=8.0 Hz), 7.13-7.15 (1H, m), 7.26-7.31 (1H, m), 10.66 (1H, s).

MS (FAB); m/z 223 (M+H)$^+$

Example 13

2-(4-Chloro-3,5-dimethyl-1H-pyrazol-1-yl)phenol a) 4-Chloro-1-(2-methoxyphenyl)-3,5-dimethyl-1H-pyrazol 193.9 mg of the title compound was obtained from 174.6 mg of 2-methoxyphenyl hydrazine hydrochloride and 114 μl of 3-chloropentane-2,4-dione in an analogous manner to Example 1a).

$^1$H-NMR (CDCl$_3$); δ (ppm) 2.09 (3H, s), 2.29 (3H, s), 3.81 (3H, s), 7.00-7.06 (2H, m), 7.30 (1H, dd, J=1.6, 7.6 Hz), 7.38-7.43 (1H, m).

MS (FAB); m/z 237 (M+H)$^+$ b) 2-(4-Chloro-3,5-dimethyl-1H-pyrazol-1-yl)phenol 151.9 mg of the title compound was obtained from 193 mg of 4-chloro-1-(2-methoxyphenyl)-3,5-dimethyl-1H-pyrazol in an analogous manner to Example 1b).

$^1$H-NMR (CDCl$_3$); δ (ppm) 2.30 (3H, s), 2.37 (3H, s), 6.91-6.95 (1H, m), 7.09 (1H, dd, J=1.6, 8.0 Hz), 7.17 (1H, dd, J=1.6, 8.0 Hz), 7.21-7.25 (1H, m), 9.23 (1H, s).

MS (FAB); m/z 223 (M+H)$^+$

Example 14

2-(3,5-Diethyl-1H-pyrazol-1-yl)phenol a) 3,5-Diethyl-1-(2-methoxyphenyl)-1H-pyrazol 209.8 mg of the title compound was obtained from 174.6 mg of 2-methoxyphenyl hydrazine hydrochloride and 135.5 μl of 3,5-heptandione in an analogous manner to Example 1a).

$^1$H-NMR (CDCl$_3$); δ (ppm) 1.14-1.18 (3H, m), 1.25-1.31 (3H, m), 2.42 (2H, q, J=7.2 Hz), 2.67-2.73 (2H, m), 3.78 (3H, s), 6.03 (1H, s), 6.99-7.04 (2H, m), 7.31-7.40 (2H, m).

MS (FAB); m/z 231 (M+H)$^+$ b) 2-(3,5-Diethyl-1H-pyrazol-1-yl)phenol 159.2 mg of the title compound was obtained from 207 mg of 3,5-diethyl-1-(2-methoxyphenyl)-1H-pyrazol in an analogous manner to Example 1b).

$^1$H-NMR (CDCl$_3$); δ (ppm) 1.24-1.31 (6H, m), 2.69 (2H, q, J=7.6 Hz), 2.76 (2H, q, J=7.6 Hz), 6.11 (1H, s), 6.90 (1H, q, J=7.6 Hz), 7.09 (1H, d, J=7.6 Hz), 7.19-7.22 (2H, m), 9.69 (1H, s).

MS (FAB); m/z 217 (M+H)$^+$

Example 15

3-(3,5-Dimethyl-1H-pyrazol-1-yl)benzene-1,2-diol a) 1-(2,3-Dimethoxyphenyl)-3,5-dimethyl-1H-pyrazol 189 mg of the title compound was obtained from 306 mg of 2,3-dimethoxyaniline in an analogous manner to Example 2b).

$^1$H-NMR (CDCl$_3$); δ (ppm) 2.14 (3H, s), 2.29 (3H, s), 3.53 (3H, s), 3.91 (3H, s), 5.96 (1H, s), 6.96-6.70 (2H, m), 7.12 (1H, t, J=8.0 Hz).

MS (FAB); m/z 233 (M+H)$^+$ b) 3-(3,5-Dimethyl-1H-pyrazol-1-yl)benzene-1,2-diol 28.9 mg of the title compound was obtained from 186 mg of 1-(2,3-dimethoxyphenyl)-3,5-dimethyl-1H-pyrazol in an analogous manner to Example 1b).

$^1$H-NMR (CDCl$_3$); δ (ppm) 2.26 (3H, s), 2.38 (3H, s), 5.99 (1H, s), 6.75-6.85 (3H, m).

MS (FAB); m/z 205 (M+H)$^+$

Example 16

2-(3,5-Dimethyl-1H-pyrazol-1-yl)benzene-1,4-diol a) 1-(2,5-Dimethoxyphenyl)-3,5-dimethyl-1H-pyrazol 260.3 mg of the title compound was obtained from 306 mg of 2,5-dimethoxyaniline in an analogous manner to Example 2b).
$^1$H-NMR (CDCl$_3$); δ (ppm) 2.11 (3H, s), 2.30 (3H, s), 3.73 (3H, s), 3.78 (3H, s), 5.96 (1H, s), 6.91-6.93 (3H, m).

b) 2-(3,5-Dimethyl-1H-pyrazol-1-yl)benzene-1,4-diol 162.6 mg of the title compound was obtained from 260.3 mg of 1-(2,5-dimethoxyphenyl)-3,5-dimethyl-1H-pyrazol in an analogous manner to Example 1b).
$^1$H-NMR (DMSO-d6); δ (ppm) 2.07 (3H, s), 2.14 (3H, s), 5.93 (1H, s), 6.56 (1H, d, J=2.8 Hz), 6.66-6.69 (1H, m), 6.80 (1H, d, J=8.8 Hz), 9.02 (1H, s), 9.17 (1H, s).
MS (FAB); m/z 205 (M+H)$^+$

Example 17

2-(4-Ethyl-3,5-dimethyl-1H-pyrazol-1-yl)phenol a) 4-Ethyl-1-(2-methoxyphenyl)-3,5-dimethyl-1H-pyrazol 236.6 mg of the title compound was obtained from 200 mg of 2-methoxyphenyl hydrazine hydrochloride and 155 µl of 3-ethyl-2,4-pentanedione in an analogous manner to Example 1a).
$^1$H-NMR (CDCl$_3$); δ (ppm) 1.13 (3H, t, J=7.6 Hz), 2.03 (3H, s), 2.27 (3H, s), 2.42 (2H, q, J=7.6 Hz), 3.79 (3H, s), 6.99-7.04 (2H, m), 7.30-7.39 (2H, m).
MS (FAB); m/z 231 (M+H)$^+$ b) 2-(4-Ethyl-3,5-dimethyl-1H-pyrazol-1-yl)phenol 196.2 mg of the title compound was obtained from 232 mg of 4-ethyl-1-(2-methoxyphenyl)-3,5-dimethyl-1H-pyrazol in an analogous manner to Example 1b).
$^1$H-NMR (CDCl$_3$); δ (ppm) 1.12 (3H, t, J=7.6 Hz), 2.27 (3H, s), 2.33 (3H, s), 2.43 (2H, q, J=7.6 Hz), 6.88-6.92 (1H, m), 7.08-7.10 (1H, m), 7.06-7.19 (2H, m), 9.90 (1H, s).
MS (FAB); m/z 217 (M+H)$^+$

Example 18

5-Fluoro-2-(3,4,5-trimethyl-1H-pyrazol-1-yl)phenol 114.7 mg of the title compound was obtained from 201.2 mg of 2-amino-5-fluorophenol and 184 µl of 3-methyl-2,4-pentanedione in an analogous manner to Example 1b).
$^1$H-NMR (CDCl$_3$); δ (ppm) 1.99 (3H, s), 2.23 (3H, s), 2.28 (3H, s), 6.59-6.64 (1H, m), 6.78-6.81 (1H, m), 7.10-7.14 (1H, m).
MS (ESI); m/z 221 (M+H)$^+$

Example 19

2-(4-Chloro-3,5-dimethyl-1H-pyrazol-1-yl)benzene-1,4-diol a) 4-Chloro-1-(2,5-dimethoxyphenyl)-3,5-dimethyl-1H-pyrazol 333.7 mg of the title compound was obtained from 306 mg of 2,5-dimethoxyaniline and 228 µl of 3-chloropentane-2,4-dione in an analogous manner to Example 2b).
$^1$H-NMR (CDCl$_3$); δ (ppm) 2.10 (3H, s), 2.29 (3H, s), 3.74 (3H, s), 3.78 (3H, s), 6.94-6.97 (2H, m), 7.26 (1H, s).
MS (FAB); m/z 267 (M+H)$^+$ b) 2-(4-Chloro-3,5-dimethyl-1H-pyrazol-1-yl)benzene-1,4-diol 184.8 mg of the title compound was obtained from 329 mg of 4-chloro-1-(2,5-dimethoxyphenyl)-3,5-dimethyl-1H-pyrazol in an analogous manner to Example 1b).
$^1$H-NMR (DMSO-d6); δ (ppm) 2.05 (3H, s), 2.15 (3H, s), 6.58 (1H, d, J=2.8 Hz), 6.72 (1H, dd, J=2.8, 8.8 Hz), 6.82 (1H, d, J=8.8 Hz), 9.11 (1H, s), 9.33 (1H, s).
MS (FAB); m/z 239 (M+H)$^+$

Example 20

4-Fluoro-2-(3,4,5-trimethyl-1H-pyrazol-1-yl)phenol 84.8 mg of the title compound was obtained from 111 mg of 2-amino-4-fluorophenol and 102 µl of 3-methyl-2,4-pentanedione in an analogous manner to Example 2b).
$^1$H-NMR (CDCl$_3$); δ (ppm) 1.99 (3H, s), 2.23 (3H, s), 2.24 (3H, s), 2.34 (3H, s), 6.87-6.95 (2H, m), 7.00-7.03 (1H, m), 9.90 (1H, s).
MS (FAB); m/z 221 (M+H)$^+$

Example 21

2-(4-Chloro-3,5-dimethyl-1H-pyrazol-1-yl)-5-fluoro phenol 62 mg of the title compound was obtained from 100 mg of 2-amino-5-fluorophenol and 90 µl of 3-chloropentane-2,4-dione in an analogous manner to Example 2b).
$^1$H-NMR (CDCl$_3$); δ (ppm) 2.29 (3H, s), 2.35 (3H, s), 6.62-6.67 (1H, m), 6.78-6.81 (1H, m), 7.10-7.14 (1H, m), 9.44 (1H, s).
MS (FAB); m/z 241 (M+H)$^+$

Example 22

Ethyl 1-(2-hydroxyphenyl)-3,5-dimethyl-1H-pyrazol-4-carboxylate a) Ethyl 1-(2-methoxyphenyl)-3,5-dimethyl-1H-pyrazol-4-carboxylate 82.6 mg of the title compound was obtained from 175 mg of 2-methoxyphenyl hydrazine hydrochloride and 156 µl of ethyl 2-acetyl-3-oxobutanoate in an analogous manner to Example 1a).

¹H-NMR (CDCl₃); δ (ppm) 1.38 (3H, t, J=7.6 Hz), 2.33 (3H, s), 2.50 (3H, s), 0.80 (3H, s), 4.32 (2H, q, J=7.6 Hz), 7.02-7.08 (2H, m), 7.30-7.32 (1H, m), 7.41-7.45 (1H, m).
MS (ESI); m/z 275 (M+H)⁺ b) Ethyl 1-(2-hydroxyphenyl)-3,5-dimethyl-1H-pyrazol-4-carboxylate 21 mg of the title compound was obtained from 82 mg of ethyl 1-(2-methoxyphenyl)-3,5-dimethyl-1H-pyrazol-4-carboxylate in an analogous manner to Example 1b).
¹H-NMR (CDCl₃); δ (ppm) 1.39 (3H, t, J=7.2 Hz), 2.50 (3H, s), 2.61 (3H, s), 4.34 (2H, q, J=7.2 Hz), 6.96 (1H, t, J=8.4 Hz), 7.10 (1H, d, J=8.4 Hz), 7.17 (1H, d, J=8.4 Hz), 7.26-7.30 (1H, m), 8.76 (1H, s).
MS (FAB); m/z 261 (M+H)⁺

Example 23

Methyl 3-(1-(2-hydroxyphenyl)-3,5-dimethyl-1H-pyrazol-4-yl)propanoate a) Methyl 3-(1-(2-methoxyphenyl)-3,5-dimethyl-1H-pyrazol-4-yl)propanoate 96 mg of the title compound was obtained from 174.6 mg of 2-methoxyphenyl hydrazine hydrochloride and 175 μl of methyl 4-acetyl-5-oxo-hexanoate in an analogous manner to Example 1a).
¹H-NMR (CDCl₃); δ (ppm) 2.04 (3H, s), 2.27 (3H, s), 2.49-2.54 (2H, m), 2.74-2.78 (2H, m), 3.68 (3H, s), 3.79 (3H, s), 6.99-7.02 (2H, m), 7.28-7.31 (1H, m), 7.35-7.39 (1H, m).
MS (FAB); m/z 289 (M+H)⁺ b) Methyl 3-(1-(2-hydroxyphenyl)-3,5-dimethyl-1H-pyrazol-4-yl)propanoate 36.8 mg of the title compound was obtained from 96 mg of methyl 3-(1-(2-methoxyphenyl)-3,5-dimethyl-1H-pyrazol-4-yl) propanoate in an analogous manner to Example 1b).
¹H-NMR (CDCl₃); δ (ppm) 2.28 (3H, s), 2.34 (3H, s), 2.51 (2H, t, J=8.0 Hz), 2.77 (2H, t, J=8.0 Hz), 3.69 (3H, s), 6.91 (1H, t, J=6.8 Hz), 7.08-7.10 (1H, m), 7.17-7.26 (2H, m), 9.73 (1H, s).
MS (ESI); m/z 275 (M+H)⁺

Example 24

2-(4-Butyl-3,5-dimethyl-1H-pyrazol-1-yl)phenol a) 4-Butyl-1-(2-methoxyphenyl)-3,5-dimethyl-1H-pyrazol 273 mg of the title compound was obtained from 175 mg of 2-methoxyphenyl hydrazine hydrochloride and 168 μl of 3-n-butyl-2,4-pentanedione in an analogous manner to Example 1a).
¹H-NMR (CDCl₃); δ (ppm) 0.94 (3H, t, J=7.2 Hz), 1.32-1.39 (2H, m), 1.45-1.50 (2H, m), 2.01 (3H, m), 2.26 (3H, s), 2.39 (2H, q, J=7.2 Hz), 3.79 (3H, s), 6.99-7.04 (2H, m), 7.30-7.38 (2H, m).
MS (FAB); m/z 259 (M+H)⁺ b) 2-(4-Butyl-3,5-dimethyl-1H-pyrazol-1-yl)phenol 208.8 mg of the title compound was obtained from 273 mg of 4-butyl-1-(2-methoxyphenyl)-3,5-dimethyl-1H-pyrazol in an analogous manner to Example 1b).

¹H-NMR (CDCl₃); δ (ppm) 0.95 (3H, t, J=7.6 Hz), 1.33-1.39 (2H, m), 1.43-1.48 (2H, m), 2.26 (3H, s), 2.32 (3H, s), 2.40 (2H, t, J=7.6 Hz), 6.88-6.92 (1H, m), 7.08 (1H, d, J=8.4 Hz), 7.16-7.20 (2H, m), 9.93 (1H, s).
MS (FAB); m/z 245 (M+H)⁺

Example 25

2-(3,5-Dimethyl-1H-pyrazol-1-yl)-5-fluorophenol a) 2-Amino-5-fluorophenol 252.5 mg of the title compound was obtained from 314 mg of 5-fluoro-2-nitrophenol in an analogous manner to Example 2a).
¹H-NMR (DMSO-d6); δ (ppm) 6.33-6.38 (1H, m), 6.45-6.48 (1H, m), 6.51-6.55 (1H, m).
MS (FAB); m/z 128 (M+H)⁺ b) 2-(3,5-Dimethyl-1H-pyrazol-1-yl)-5-fluorophenol 89.6 mg of the title compound was obtained from 150 mg of 2-amino-5-fluorophenol in an analogous manner to Example 2b).
¹H-NMR (CDCl₃); δ (ppm) 2.29 (3H, s), 2.37 (3H, s), 6.03 (1H, s), 6.60-6.65 (1H, m), 6.78-6.81 (1H, m), 7.13-7.16 (1H, m).
MS (ESI); m/z 207 (M+H)⁺

Example 26

5-Chloro-2-(3,5-dimethyl-1H-pyrazol-1-yl)phenol 168.8 mg of the title compound was obtained from 287 mg of 2-amino-5-chlorophenol in an analogous manner to Example 2b).
¹H-NMR (CDCl₃); δ (ppm) 2.30 (3H, s), 2.40 (3H, s), 6.05 (1H, s), 6.87-6.90 (1H, m), 7.10-7.14 (2H, m), 10.23 (1H, s).
MS (FAB); m/z 223 (M+H)⁺

Example 27

2-(3,5-Dimethyl-1H-pyrazol-1-yl)-3-nitrophenol 75.4 mg of the title compound was obtained from 308 mg of 2-amino-3-nitrophenol in an analogous manner to Example 2b).
¹H-NMR (CD₃OD); δ (ppm) 2.14 (3H, s), 2.19 (3H, s), 6.04 (1H, s), 7.27 (1H, dd, J=1.6, 7.6 Hz), 7.44 (1H, dd, J=1.6, 7.6 Hz), 7.50 (1H, t, J=7.6 Hz).
MS (FAB); m/z 234 (M+H)⁺

Example 28

2-(3,5-Dimethyl-1H-pyrazol-1-yl)-5-nitrophenol 101 mg of the title compound was obtained from 308 mg of 2-amino-5-nitrophenol in an analogous manner to Example 2b).
¹H-NMR (CDCl₃); δ (ppm) 2.33 (3H, s), 2.50 (3H, s), 6.13 (1H, s), 7.38 (1H, d, J=7.6 Hz), 7.79-7.81 (1H, m), 7.95 (1H, s).
MS (ESI); m/z 234 (M+H)⁺

Example 29

3-(1-(2-Hydroxyphenyl)-3,5-dimethyl-1H-pyrazol-4-yl)propionic acid 29.9 mg of methyl 3-(1-(2-hydroxyphenyl)-3,5-dimethyl-1Hpyrazol-4-yl)propanoate was dissolved in 0.6 ml of methanol, and to the mixture was added 0.29 ml of 1N-sodium hydroxide and stirred at room temperature for 3.5 hours. To the reaction mixture was added 20 ml of water, neutralized with 1N-hydrochloric acid, and extracted with 20 ml of ethyl acetate. After the organic layer was dried over anhydrous magnesium sulfate, the solvent was distilled off under reduced pressure to yield 7.5 mg of the title compound.

$^1$H-NMR (CDCl$_3$); δ (ppm) 2.29 (3H, s), 2.34 (3H, s), 2.56 (2H, t, J=7.6 Hz), 2.78 (2H, t, J=7.6 Hz), 6.89-6.93 (1H, m), 7.08-7.10 (1H, m), 7.16-7.22 (2H, m).

MS (FAB); m/z 261 (M+H)$^+$

Example 30

5-Chloro-2-(3,4,5-trimethyl-1H-pyrazol-1-yl)phenol 152 mg of the title compound was obtained from 287 mg of 2-amino-5-chlorophenol and 233 µl of 3-methyl-2,4-pentanedione in an analogous manner to Example 2b).

$^1$H-NMR (CDCl$_3$); δ (ppm) 1.99 (3H, s), 2.24 (3H, s), 2.31 (3H, s), 6.86-6.89 (1H, m), 7.09-7.11 (2H, m).

MS (FAB); m/z 227 (M+H)$^+$

Example 31

5-Amino-2-(3,5-dimethyl-1H-pyrazol-1-yl)phenol 86 mg of 2-(3,5-dimethyl-1H-pyrazol-1-yl)-5-nitrophenol was dissolved in 1.7 ml of ethanol, and 43 mg of 10% palladium/carbon was added and stirred under hydrogen atmosphere at room temperature for 45 minutes. After the insoluble matter was filtered off, the solvent was distilled off under reduced pressure to yield 30.4 mg of the title compound.

$^1$H-NMR (CDCl$_3$); δ (ppm) 2.28 (3H, s), 2.33 (3H, s), 3.72 (2H, s), 5.99 (1H, s), 6.22 (1H, dd, J=2.4, 8.4 Hz), 6.40 (1H, d, J=2.4 Hz), 6.97 (1H, d, J=8.4 Hz), 9.27 (1H, s).

MS (FAB); m/z 204 (M+H)$^+$

Example 32

5-Nitro-2-(3,4,5-trimethyl-1H-pyrazol-1-yl)phenol 289.5 mg of the title compound was obtained from 308 mg of 2-amino-5-nitrophenol and 233 µl of 3-methyl-2,4-pentanedione in an analogous manner to Example 2b).

$^1$H-NMR (CDCl$_3$); δ (ppm) 2.02 (3H, s), 2.24 (3H, s), 2.40 (3H, s), 7.33 (1H, d, J=8.8 Hz), 7.79 (1H, dd, J=2.4, 8.8 Hz), 7.94 (1H, d, J=2.4 Hz).

MS (FAB); m/z 248 (M+H)$^+$

Example 33

4-(3,5-Dimethyl-1H-pyrazol-1-yl)benzene-1,3-diol a) 2,4-Dimethoxyphenylboronic acid

576 µl of 1-bromo-2,4-dimethoxybenzene was dissolved in 5.8 ml of tetrahydrofuran and 3 ml of 1.6 mol/l solution of n-butyl lithium in hexane was added dropwise at −78° C. under argon atmosphere. Then, 1.1 ml of triisopropylborate was added, and after stirred at −78° C. for 40 minutes, the mixture was stirred at room temperature for 2 hours. To the reaction mixture, 40 ml of water and 1 ml of 5N-hydrochloric acid was added, and extracted with 50 ml of ethyl acetate. After the organic layer was dried over anhydrous magnesium sulfate, the solvent was distilled off under reduced pressure, and purified by silica gel column chromatography (hexane:ethyl acetate=2:1) to yield 610.2 mg of the title compound.

$^1$H-NMR (CDCl$_3$); δ (ppm) 3.85 (3H, s), 3.89 (3H, s), 5.81 (2H, s), 6.46 (1H, s), 6.56 (1H, dd, J=2.0, 8.4 Hz), 7.77 (1H, d, J=8.4 Hz).

b) 1-(2,4-Dimethoxyphenyl)-3,5-dimethyl-1H-pyrazol 610.2 mg of 2,4-dimethoxyphenylboronic acid was dissolved in 6 ml of methylene chloride, to the mixture were added 387 mg of 3,5-dimethylpyrazol, 730 mg of copper(II) acetate and 948 µl of pyridine, and the mixture was stirred overnight at room temperature. To the reaction mixture was added 60 ml of water and extracted with 60 ml of ethyl acetate. After the organic layer was dried over anhydrous magnesium sulfate, the solvent was distilled off under reduced pressure, and purified by silica gel column chromatography (hexane:ethyl acetate=3:2) to yield 81.7 mg of the title compound.

$^1$H-NMR (CDCl$_3$); δ (ppm) 2.07 (3H, s), 2.29 (3H, s), 3.77 (3H, s), 3.85 (3H, s), 5.94 (1H, s), 6.52-6.54 (2H, m), 7.22-7.24 (1H, m).

MS (FAB); m/z 233 (M+H)$^+$ c) 4-(3,5-Dimethyl-1H-pyrazol-1-yl)benzene-1,3-diol 118.4 mg of 1-(2,4-dimethoxyphenyl)-3,5-dimethyl-1H-pyrazol was dissolved in 2.3 ml of methylene chloride, and 1.7 ml of 1M solution of boron tribromide in methylene chloride was added at room temperature and stirred for 1 hour. The reaction mixture was added to 30 ml of water, neutralized with 1N-sodium hydroxide, and extracted with 50 ml of ethyl acetate. After the organic layer was dried over anhydrous magnesium sulfate, the solvent was distilled off under reduced pressure, and purified using preparative thin-layer silica gel column chromatography (hexane:ethyl acetate=1:2) to yield 71.7 mg of the title compound.

$^1$H-NMR (CDCl$_3$); δ (ppm) 2.29 (3H, s), 2.33 (3H, s), 6.01 (1H, s), 6.37 (1H, dd, J=2.8, 8.8 Hz), 6.53 (1H, d, J=2.8 Hz), 7.03 (1H, d, J=8.8 Hz).

MS (ESI); m/z 205 (M+H)$^+$

Example 34

5-Amino-2-(3,4,5-trimethyl-1H-pyrazol-1-yl)phenol 118.4 mg of the title compound was obtained from 200 mg of 5-nitro-2-(3,4,5-trimethyl-1H-pyrazol-1-yl)phenol in an analogous manner to Example 31.

$^1$H-NMR (CDCl$_3$); δ (ppm) 1.97 (3H, s), 2.23 (3H, s), 2.24 (3H, s), 3.70 (2H, s), 6.22 (1H, dd, J=2.4, 8.4 Hz), 6.40 (1H, d, J=2.4 Hz), 6.95 (1H, d, J=8.4 Hz), 9.34 (1H, s).

MS (FAB); m/z 218 (M+H)$^+$

Example 35

Methyl 4-(3,5-dimethyl-1H-pyrazol-1-yl)-3-hydroxybenzene carboxylate 239.4 mg of the title compound was obtained from 334 mg of methyl 4-amino-3-hydroxybenzene carboxylate in an analogous manner to Example 2b).
$^1$H-NMR (CDCl$_3$); δ (ppm) 2.31 (3H, s), 2.45 (3H, s), 3.92 (3H, s), 6.08 (1H, s), 7.26-7.29 (1H, m), 7.60 (1H, dd, J=1.6, 8.0 Hz), 7.76 (1H, d, J=1.6 Hz).
MS (ESI); m/z 247 (M+H)$^+$

Example 36

3-Amino-2-(3,5-dimethyl-1H-pyrazol-1-yl)phenol 38.9 mg of the title compound was obtained from 56.6 mg of 2-(3,5-dimethyl-1H-pyrazol-1-yl)-3-nitrophenol in an analogous manner to Example 31.
$^1$H-NMR (CDCl$_3$); δ (ppm) 2.14 (3H, s), 2.25 (3H, s), 3.57 (2H, s), 6.02 (1H, s), 6.32-6.37 (2H, m), 7.02 (1H, t, J=8.0 Hz).
MS (FAB); m/z 204 (M+H)$^+$

Example 37

4-(3,5-Dimethyl-1H-pyrazol-1-yl)-3-hydroxybenzene carboxylic acid 100 mg of methyl 4-(3,5-dimethyl-1H-pyrazol-1-yl)-3-hydroxybenzene carboxylate was dissolved in 1 ml of methanol, and 1.6 ml of 1N-sodium hydroxide was added at room temperature and stirred for 3.5 hours. To the reaction mixture, 20 ml of water was added, neutralized with 1N-hydrochloric acid, and extracted with 20 ml of ethyl acetate. After the organic layer was dried over anhydrous magnesium sulfate, the solvent was distilled off under reduced pressure to yield 40.8 mg of the title compound.
$^1$H-NMR (CD$_3$OD); δ (ppm) 2.16 (3H, s), 2.24 (3H, s), 6.04 (1H, s), 7.30 (1H, d, J=8.4 Hz), 7.59 (1H, dd, J=2.0, 8.4 Hz), 7.64 (1H, d, J=2.0 Hz).
MS (ESI); m/z 233 (M+H)$^+$

Example 38

4-(3,5-Dimethyl-1H-pyrazol-1-yl)-3-hydroxy-N,N-dimethylbenzamide 36 mg of 4-(3,5-dimethyl-1H-pyrazol-1-yl)-3-hydroxybenzene carboxylic acid was dissolved in 0.4 ml of DMF, and 36 mg of 1-(3-dimethylamino propyl)-3-ethylcarbodiimide hydrochloride, 25 mg of 1-hydroxybenzotriazole, and 93 μl of dimethylamine (2.0M THF solution) were added and stirred at room temperature for 4 hours. To the reaction mixture was added 10 ml of water, and extracted with 15 ml of ethyl acetate. After the organic layer was dried over anhydrous magnesium sulfate, the solvent was distilled off under reduced pressure, and purified using a preparative thin-layer silica gel column chromatography (ethyl acetate) to yield 11.4 mg of the title compound.
$^1$H-NMR (CDCl$_3$); δ (ppm) 2.31 (3H, s), 2.41 (3H, s), 3.02 (3H, s), 3.11 (3H, s), 6.06 (1H, s), 6.97 (1H, d, J=8.0 Hz), 7.23 (1H, d, J=8.0 Hz), 7.26 (1H, s).
MS (ESI); m/z 259 (M+H)$^+$

Example 39

4-(3,5-Dimethyl-1H-pyrazol-1-yl)-3-hydroxy benzamide 34.3 mg of the title compound was obtained from 73.1 mg of 4-(3,5-dimethyl-1H-pyrazol-1-yl)-3-hydroxybenzene carboxylic acid and 38 μl of ammonia water, in an analogous manner to Example 38.
$^1$H-NMR (CD$_3$OD); δ (ppm) 2.16 (3H, s), 2.24 (3H, s), 6.04 (1H, s), 7.29 (1H, d, J=8.4 Hz), 7.41 (1H, dd, J=2.0, 8.4 Hz), 7.50 (1H, d, J=2.0 Hz).
MS (ESI); m/z 232 (M+H)$^+$

Example 40

3-Hydroxy-4-(3,4,5-trimethyl-1H-pyrazol-1-yl)benzene carboxylic acid a) Methyl 3-hydroxy-4-(3,4,5-trimethyl-1H-pyrazol-1-yl)-benzene carboxylate 110.4 mg of the title compound was obtained from 167 mg of methyl 4-amino-3-hydroxybenzene carboxylate and 116 μl of 3-methyl-2,4-pentanedione in an analogous manner to Example 2b).
$^1$H-NMR (CDCl$_3$); δ (ppm) 2.00 (3H, s), 2.26 (3H, s), 2.36 (3H, s), 3.92 (3H, s), 7.23-7.26 (1H, m), 7.58-7.60 (1H, m), 7.49 (1H, s), 10.53 (1H, s).
MS (ESI); m/z 261 (M+H)$^+$ b) 3-Hydroxy-4-(3,4,5-trimethyl-1H-pyrazol-1-yl) benzene carboxylic acid 68.7 mg of the title compound was obtained from 110 mg of methyl 3-hydroxy-4-(3,4,5-trimethyl-1H-pyrazol-1-yl)-benzene carboxylate in an analogous manner to Example 37.
$^1$H-NMR (CD$_3$OD); δ (ppm) 1.99 (3H, s), 2.09 (3H, s), 2.20 (3H, s), 7.28 (1H, d, J=8.0 Hz), 7.59 (1H, dd, J=2.0, 8.0 Hz), 7.63 (1H, d, J=2.0 Hz).
MS (ESI); m/z 247 (M+H)$^+$

Example 41

3-Hydroxy-4-(3,4,5-trimethyl-1H-pyrazol-1-yl)benzamide 33.3 mg of the title compound was obtained from 65 mg of 3-hydroxy-4-(3,4,5-trimethyl-1H-pyrazol-1-yl)benzene carboxylic acid and 32 μl of ammonia water in an analogous manner to Example 38.
$^1$H-NMR (CD$_3$OD); δ (ppm) 1.99 (3H, s), 2.09 (3H, s), 2.19 (3H, s), 7.27 (1H, d, J=8.0 Hz), 7.40 (1H, dd, J=2.0, 8.0 Hz), 7.57 (1H, d, J=2.0 Hz).
MS (ESI); m/z 246 (M+H)$^+$

Example 42

4-(4-Chloro-3,5-dimethyl-1H-pyrazol-1-yl)-3-hydroxybenzamide a) Methyl 4-(4-chloro 3,5-dimethyl-1H-pyrazol-1-yl)-3-hydroxybenzoate 69.1 mg of the title compound was obtained from 167 mg of methyl 4-amino-3-hydroxybenzoate and 114 μl of 3-chloropentane-2,4-dione in an analogous manner to Example 2b).

$^1$H-NMR (CDCl$_3$); δ (ppm) 2.32 (3H, s), 2.42 (3H, s), 3.93 (3H, s), 7.24-7.26 (1H, m), 7.60-7.66 (1H, m), 7.77 (1H, s).

b) 4-(4-Chloro-3,5-dimethyl-1H-pyrazol-1-yl)-3-hydroxybenzoic acid 39.2 mg of the title compound was obtained from 69.1 mg of methyl 4-(4-chloro-3,5-dimethyl-1H-pyrazol-1-yl)-3-hydroxybenzoate in an analogous manner to Example 37.
$^1$H-NMR (CD$_3$OD); δ (ppm) 2.15 (3H, s), 2.24 (3H, s), 7.32-7.35 (1H, m), 7.59-7.66 (2H, m).
MS (ESI); m/z 267 (M+H)$^+$ c) 4-(4-Chloro-3,5-dimethyl-1H-pyrazol-1-yl)-3-hydroxy benzamide 12.3 mg of the title compound was obtained from 37.9 mg of 4-(4-chloro-3,5-dimethyl-1H-pyrazol-1-yl)-3-hydroxybenzoic acid and 17 µl of ammonia water in an analogous manner to Example 38.
$^1$H-NMR (CD$_3$OD); δ (ppm) 2.14 (3H, s), 2.24 (3H, s), 7.29-7.32 (1H, m), 7.41-7.44 (1H, m), 7.50 (1H, s).
MS (ESI); m/z 266 (M+H)$^+$ Example 43

2-(3,5-Dimethyl-1H-pyrazol-1-yl)benzene-1,3-diol a) 2-Aminobenzene-1,3-diol 465 mg of 2-nitroresorcinol was dissolved in 9.3 ml of ethanol, and 230 mg of 10% palladium/carbon was added, and stirred under hydrogen atmosphere at room temperature for 1 hour. After the insoluble matter was filtered off, solvent was distilled off under reduced pressure to yield 338.5 mg of the title compound.
$^1$H-NMR (DMSO-d6); δ (ppm) 6.20-6.28 (3H, m).
MS (ESI); m/z 126 (M+H)$^+$ b) 2-Amino-1,3-phenylene bis(4-methylbenzene sulfonate)

100 mg of 2-aminobenzene-1,3-diol was dissolved in 2 ml of dichloromethane, and 234 µl of triethyl amine and 320 mg of p-toluene sulfonyl chloride were added and stirred at room temperature for 1.5 hours. To the reaction mixture, 20 ml of water was added, and extracted with 20 ml of ethyl acetate. After the organic layer was dried over anhydrous magnesium sulfate, the solvent was distilled off under reduced pressure, and purified by silica gel column chromatography (hexane: ethyl acetate=4:1) to yield 278.1 mg of the title compound.
$^1$H-NMR (CDCl$_3$); δ (ppm) 2.46 (6H, s), 3.83 (2H, s), 6.48 (1H, t, J=8.1 Hz), 6.79 (2H, d, J=8.3 Hz), 7.32 (4H, d, J=8.1 Hz), 7.72 (4H, d, J=8.3 Hz).
MS (ESI); m/z 434 (M+H)$^+$ c) 2-(3,5-Dimethyl-1H-pyrazol-1-yl)-3-hydroxyphenyl 4-methylbenzene sulfonate To 278 mg of 2-amino-1,3-phenylene bis(4-methylbenzene sulfonate) was added 0.64 ml of 5N-hydrochloric acid, and to the mixture a solution in which 58 mg of sodium nitrite was dissolved in 0.4 ml of water was added dropwise at 0° C., and stirred for 30 minutes. Then, a solution in which 289 mg of stannous chloride was dissolved in 0.32 ml of 5N-hydrochloric acid was added dropwise at 0° C. and stirred for 1 hour. The solvent was distilled off under reduced pressure, and 1.3 ml of ethanol and 66 µl of acetyl acetone were added and heated at reflux for 2 hours. To the reaction mixture was added 50 ml of water, and neutralized with a saturated sodium bicarbonate solution and extracted with 50 ml of ethyl acetate. After the organic layer was dried over anhydrous magnesium sulfate, the solvent was distilled off under reduced pressure, and purified using silica gel column chromatography (hexane:ethyl acetate=4:1 to 1:1) to yield 62.9 mg of the title compound.
$^1$H-NMR (CDCl$_3$); δ (ppm) 2.15 (3H, s), 2.17 (3H, s), 2.41 (3H, s), 5.91 (1H, s), 6.93-6.96 (2H, m), 7.14 (2H, d, J=8.0 Hz), 7.18-7.26 (1H, m), 7.35 (2H, d, J=8.0 Hz).
MS (ESI); m/z 359 (M+H)$^+$ d) 2-(3,5-Dimethyl-1H-pyrazol-1-yl)benzene-1,3-diol To 62 mg of 2-(3,5-dimethyl-1H-pyrazol-1-yl)-3-hydroxyphenyl 4-methylbenzene sulfonate was added a solution in which 97 mg of potassium hydroxide was dissolved in 1.5 ml of ethanol and 1.5 ml of water, and heated at reflux for 3.5 hours. To the reaction mixture, 20 ml of water was added, and extracted with 20 ml of ethyl acetate. After the organic layer was dried over anhydrous magnesium sulfate, the solvent was distilled off under reduced pressure, and purified using preparative thin-layer silica gel column chromatography (hexane:ethyl acetate=1:1) to yield 20.8 mg of the title compound.
$^1$H-NMR (CDCl$_3$); δ (ppm) 2.15 (3H, s), 2.16 (3H, s), 5.98 (1H, s), 6.45 (2H, d, J=8.4 Hz), 7.00 (1H, t, J=8.4 Hz).
MS (ESI); m/z 205 (M+H)$^+$ Example 44

2-(3,5-Dimethyl-1H-pyrazol-1-yl)-5-methylphenol a) 2-Amino-5-methylphenyl 4-methylbenzene sulfonate 400 mg of 2-amino-5-methylphenol was dissolved in 6.5 ml of dichloromethane, and 476 µl of triethylamine and 619 mg of p-toluene sulfonylchloride were added and stirred at room temperature for 1 hour. To the reaction mixture, 60 ml of water was added, and extracted with 60 ml of ethyl acetate. After the organic layer was dried over anhydrous magnesium sulfate, the solvent was distilled off under reduced pressure, and purified using silica gel column chromatography (hexane:ethyl acetate=3:1) to yield 730.1 mg of the title compound.
$^1$H-NMR (CDCl$_3$); δ (ppm) 2.15 (3H, s), 2.46 (3H, s), 3.63 (2H, brs), 6.61-6.63 (1H, m), 6.67 (1H, s), 6.82-6.85 (1H, m), 6.33 (2H, d, J=8.4 Hz), 7.78 (2H, d, J=8.4 Hz).
MS (ESI); m/z 278 (M+H)$^+$ b) 2-(3,5-Dimethyl-1H-pyrazol-1-yl)-5-methylphenyl 4-methylbenzene sulfonate To 453 mg of 2-amino-5-methylphenyl 4-methylbenzene sulfonate was added 1.6 ml of 5N-hydrochloric acid, and a solution in which 146 mg of sodium nitrite was dissolved in 1 ml of water was added dropwise at 0° C., and stirred for 30 minutes. Then, a solution in which 736 mg of stannous chloride was dissolved in 0.8 ml of 5N-hydrochloric acid was added dropwise at 0° C. and stirred for 1 hour. The solvent was distilled off under reduced pressure, 3.2 ml of ethanol and 167 µl of acetyl acetone were added and heated at reflux for 2 hours. To the reaction mixture was added 50 ml of water, neutralized with a saturated sodium bicarbonate solution, and extracted with 80 ml of ethyl acetate. After the organic layer was dried over anhydrous magnesium sulfate, the solvent was distilled off under reduced pressure, and purified using silica gel column chromatography (hexane:ethyl acetate=2:1) to yield 199.6 mg of the title compound.

$^1$H-NMR (CDCl$_3$); δ (ppm) 2.09 (3H, s), 2.11 (3H, s), 2.41 (3H, s), 2.43 (3H, s), 5.82 (1H, s), 7.15-7.21 (4H, m), 7.36-7.38 (3H, m).

MS (ESI); m/z 357 (M+H)$^+$ c) 2-(3,5-Dimethyl-1H-pyrazol-1-yl)-5-methylphenol

To 199.6 mg of 2-(3,5-dimethyl-1H-pyrazol-1-yl)-5-methylphenyl 4-methylbenzene sulfonate was added a solution in which 314 mg of potassium hydroxide was dissolved in 4 ml of ethanol and 4 ml of water, and the mixture was heated at reflux for 1 hour. To the reaction mixture was added 20 ml of water, and extracted with 20 ml of ethyl acetate. After the organic layer was dried over anhydrous magnesium sulfate, the solvent was distilled off under reduced pressure and purified using preparative thin-layer silica gel column chromatography (hexane:ethyl acetate=4:1), and after the desired fraction was dissolved in 1,4-dioxane, it was lyophilized to yield 66.2 mg of the title compound.

$^1$H-NMR (CDCl$_3$); δ (ppm) 2.29 (3H, s), 2.33 (3H, s), 2.37 (3H, s), 6.01 (1H, s), 6.70 (1H, d, J=8.0 Hz), 6.90 (1H, s), 7.07 (1H, d, J=8.0 Hz), 9.64 (1H, brs).

MS (ESI); m/z 203 (M+H)$^+$

Example 45

2-(3,5-Dimethyl-1H-pyrazol-1-yl)-5-methoxyphenol a) 2-Amino-5-methoxyphenyl 4-methylbenzene sulfonate 220.1 mg of the title compound was obtained from 176 mg of 2-hydroxy-4-methoxyaniline hydrochloride in an analogous manner to Example 44a).

$^1$H-NMR (CDCl$_3$); δ (ppm) 2.46 (3H, s), 3.62 (3H, s), 6.41 (1H, s), 6.65-6.66 (2H, m), 7.34 (2H, d, J=8.8 Hz), 7.79 (2H, d, J=8.8 Hz).

b) 2-(3,5-Dimethyl-1H-pyrazol-1-yl)-5-methoxyphenyl 4-methylbenzene sulfonate 93.7 mg of the title compound was obtained from 220 mg of 2-amino-5-methoxyphenyl 4-methylbenzene sulfonate in an analogous manner to Example 44b).

$^1$H-NMR (CDCl$_3$); δ (ppm) 2.08 (3H, s), 2.11 (3H, s), 2.41 (3H, s), 3.85 (3H, s), 5.82 (1H, s), 6.87 (1H, dd, J=2.4, 8.4 Hz), 7.06 (1H, d, J=2.4 Hz), 7.17 (2H, d, J=8.4 Hz), 7.20-7.24 (1H, m), 7.39 (2H, d, J=8.4 Hz).

MS (ESI); m/z 373 (M+H)$^+$ c) 2-(3,5-Dimethyl-1H-pyrazol-1-yl)-5-methoxyphenol 30.1 mg of the title compound was obtained from 93 mg of 2-(3,5-dimethyl-1H-pyrazol-1-yl)-5-methoxyphenyl 4-methylbenzene sulfonate in an analogous manner to Example 44c).

$^1$H-NMR (CDCl$_3$); δ (ppm) 2.27 (3H, s), 2.33 (3H, s), 3.80 (3H, s), 6.00 (1H, s), 6.45 (1H, dd, J=2.8, 8.4 Hz), 6.61 (1H, d, J=2.8 Hz), 7.08 (1H, d, J=8.4 Hz), 9.67 (1H, brs).

MS (ESI); m/z 219 (M+H)$^+$

Example 46

2-(3,5-Dimethyl-1H-pyrazol-1-yl)-3-methylphenol a) 2-Amino-3-methylphenyl 4-methylbenzene sulfonate 374.1 mg of the title compound was obtained from 200 mg of 2-amino-3-methylphenol in an analogous manner to Example 43b).

$^1$H-NMR (CDCl$_3$); δ (ppm) 2.14 (3H, s), 2.46 (3H, s), 3.79 (2H, s), 6.51 (1H, t, J=8.0 Hz), 6.63 (1H, d, J=8.0 Hz), 6.91 (1H, d, J=8.0 Hz), 7.32 (2H, d, J=8.4 Hz), 7.78 (2H, d, J=8.4 Hz).

MS (ESI); m/z 278 (M+H)$^+$ b) 2-(3,5-Dimethyl-1H-pyrazol-1-yl)-3-methylphenyl 4-methylbenzene sulfonate 269.9 mg of the title compound was obtained from 374 mg of 2-amino-3-methylphenyl 4-methylbenzene sulfonate in an analogous manner to Example 43c).

$^1$H-NMR (CDCl$_3$); δ (ppm) 2.01 (3H, s), 2.02 (3H, s), 2.16 (3H, s), 2.43 (3H, s), 5.88 (1H, s), 7.19-7.24 (3H, m), 7.32 (2H, d, J=5.2 Hz), 7.51 (2H, d, J=8.4 Hz).

MS (ESI); m/z 357 (M+H)$^+$ c) 2-(3,5-Dimethyl-1H-pyrazol-1-yl)-3-methylphenol 79.2 mg of the title compound was obtained from 269 mg of 2-(3,5-dimethyl-1H-pyrazol-1-yl)-3-methylphenyl 4-methylbenzene sulfonate in an analogous manner to Example 43d).

$^1$H-NMR (CD$_3$OD); δ (ppm) 1.92 (3H, s), 2.01 (3H, s), 2.24 (3H, s), 6.02 (1H, s), 6.79 (2H, d, J=7.6 Hz), 7.18 (1H, t, J=7.6 Hz).

MS (ESI); m/z 203 (M+H)$^+$

Example 47

2-(3,5-Dimethyl-1H-pyrazol-1-yl)-5-hydroxymethylphenol 132 mg of methyl 4-(3,5-dimethyl-1H-pyrazol-yl)-3-hydroxybenzene carboxylate was dissolved in 2.6 ml of tetrahydrofuran, and 58 mg of lithium borohydride was added and stirred at 50° C. for 3.5 hours. To the reaction mixture was added 20 ml of water, and extracted with 20 ml of ethyl acetate. After the organic layer was dried over anhydrous magnesium sulfate, the solvent was distilled off under reduced pressure, and purified using preparative thin-layer silica gel column chromatography (hexane:ethyl acetate=1:2) to yield 12.4 mg of the title compound.

$^1$H-NMR (CDCl$_3$); δ (ppm) 2.28 (3H, s), 2.44 (3H, s), 4.64 (2H, s), 6.02 (1H, s), 6.90 (1H, d, J=8.0 Hz), 7.02 (1H, s), 7.17 (1H, d, J=8.0z).

MS (ESI); m/z 219 (M+H)$^+$

Example 48

2-(3,5-Dimethyl-1H-pyrazol-1-yl)-5-methylaminophenol a) 1-(2-Methoxy-4-nitrophenyl)-3,5-dimethyl-1H-pyrazol 498 mg of the title compound was obtained from 700 mg of 2-methoxy-4-nitroaniline in an analogous manner to Example 43c).
$^1$H-NMR (CDCl$_3$); δ (ppm) 2.13 (3H, s), 2.30 (3H, s), 3.93 (3H, s), 6.02 (1H, s), 7.53 (1H, d, J=8.4 Hz), 7.89 (1H, d, J=2.0 Hz), 7.95 (1H, dd, J=2.0, 8.4 Hz).
MS (ESI); m/z 248 (M+H)$^+$ b) 4-(3,5-Dimethyl-1H-pyrazol-1-yl)-3-methoxyaniline 417.6 mg of the title compound was obtained from 495 mg of 1-(2-methoxy-4-nitrophenyl)-3,5-dimethyl-1H-pyrazol in an analogous manner to Example 31.
$^1$H-NMR (CDCl$_3$); δ (ppm) 2.06 (3H, s), 2.28 (3H, s), 3.72 (3H, s), 3.81 (2H, brs), 5.92 (1H, s), 6.28-6.31 (2H, m), 7.06 (1H, d, J=8.4 Hz).
MS (ESI); m/z 218 (M+H)$^+$ c) 4-(3,5-Dimethyl-1H-pyrazol-1-yl)-3-methoxy-N-methylaniline 200 mg of 4-(3,5-dimethyl-1H-pyrazol-1-yl)-3-methoxyaniline was dissolved in 6 ml of dimethylformamide, and 160 μl of methyl iodide and 636 mg of potassium carbonate were added and stirred at room temperature for 2.5 hours. To the reaction mixture, 50 ml of water was added and extracted with 50 ml of ethyl acetate. After the organic layer was dried over anhydrous magnesium sulfate, the solvent was distilled off under reduced pressure, and purified using preparative thin-layer silica gel column chromatography (hexane:ethyl acetate=1:3) to yield 48.7 mg of the title compound.
$^1$H-NMR (CDCl$_3$); δ (ppm) 2.07 (3H, s), 2.28 (3H, s), 2.86 (3H, s), 3.74 (3H, s), 3.95 (1H, brs), 5.92 (1H, s), 6.17 (1H, d, J=2.4 Hz), 6.21 (1H, dd, J=2.4, 8.4 Hz), 7.09 (1H, d, J=8.4 Hz).
MS (ESI); m/z 232 (M+H)$^+$ d) 2-(3,5-Dimethyl-1H-pyrazol-1-yl)-5-methylamino phenol 25 mg of the title compound was obtained from 58.7 mg of 4-(3,5-dimethyl-1H-pyrazol-1-yl)-3-methoxy-N-methylaniline in an analogous manner to Example 33c).
$^1$H-NMR (CDCl$_3$); δ (ppm) 2.28 (3H, s), 2.32 (3H, s), 2.83 (3H, d, J=1.2 Hz), 5.98 (1H, s), 6.13-6.16 (1H, m), 6.31-6.32 (1H, m), 6.99 (1H, dd, J=1.2, 8.4 Hz).
MS (ESI); m/z 218 (M+H)$^+$

Example 49

2-(3,5-Dimethyl-1H-pyrazol-1-yl)-4-methylphenol a) 2-Amino-4-methylphenyl 4-methylbenzene sulfonate 770.1 mg of the title compound was obtained from 479 mg of 2-amino-4-methylphenol hydrochloride in an analogous manner to Example 43b).
$^1$H-NMR (CDCl$_3$); δ (ppm) 2.21 (3H, s), 2.46 (3H, s), 3.74 (2H, brs), 6.39 (1H, d, J=8.0 Hz), 6.53 (1H, s), 6.62 (1H, d, J=8.0 Hz), 7.32 (2H, d, J=8.0 Hz), 7.77 (2H, d, J=8.0 Hz).
MS (ESI); m/z 278 (M+H)$^+$ b) 2-(3,5-Dimethyl-1H-pyrazol-1-yl)-4-methylphenyl 4-methylbenzene sulfonate 137.3 mg of the title compound was obtained from 400 mg of 2-amino-4-methylphenyl 4-methylbenzene sulfonate in an analogous manner to Example 43c).
$^1$H-NMR (CDCl$_3$); δ (ppm) 2.10 (3H, s), 2.12 (3H, s), 2.35 (3H, s), 2.41 (3H, s), 5.82 (1H, s), 7.13-7.15 (3H, m), 7.20-7.22 (1H, m), 7.33-7.36 (2H, m), 7.42 (2H, d, J=8.4 Hz).
MS (ESI); m/z 357 (M+H)$^+$ c) 2-(3,5-Dimethyl-1H-pyrazol-1-yl)-4-methylphenol 60.4 mg of the title compound was obtained from 167 mg of 2-(3,5-dimethyl-1H-pyrazol-1-yl)-4-methylphenyl 4-methylbenzene sulfonate in an analogous manner to Example 43d).
$^1$H-NMR (CDCl$_3$); δ (ppm) 2.29 (3H, s), 2.31 (3H, s), 2.39 (3H, s), 6.02 (1H, s), 6.97-7.02 (3H, m), 9.43 (1H, s).
MS (ESI); m/z 203 (M+H)$^+$

Example 50

2-(3,5-Dimethyl-1H-pyrazol-1-yl)-5-trifluoromethylphenol a) 1-(2-Methoxy-4-trifluoromethylphenyl)-3,5-dimethyl-1H-pyrazol 95.5 mg of the title compound was obtained from 191 mg of 2-methoxy-4-trifluoromethylaniline in an analogous manner to Example 43c).
$^1$H-NMR (CDCl$_3$); δ (ppm) 2.05 (3H, s), 2.30 (3H, s), 3.86 (3H, s), 5.99 (1H, s), 7.22 (1H, s), 7.31 (1H, d, J=8.0 Hz), 7.46 (1H, d, J=8.0 Hz).
MS (ESI); m/z 271 (M+H)$^+$ b) 2-(3,5-Dimethyl-1H-pyrazol-1-yl)-5-trifluoromethylphenol 25.7 mg of the title compound was obtained from 95.5 mg of 1-(2-methoxy-4-trifluoromethylphenyl)-3,5-dimethyl-1H-pyrazol in an analogous manner to Example 33c).
$^1$H-NMR (CDCl$_3$); δ (ppm) 2.31 (3H, s), 2.45 (3H, s), 6.08 (1H, s), 7.15-7.18 (1H, m), 7.30-7.35 (2H, m), 10.64 (1H, s).
MS (ESI); m/z 257 (M+H)$^+$

Example 51

2-(3,5-dimethyl-1H-pyrazol-1-yl)-6-methylphenol a) 2-Amino-6-methylphenyl 4-methylbenzene sulfonate 159.9 mg of the title compound was obtained from 200 mg of 6-amino-o-cresol hydrochloride in an analogous manner to Example 43b).
$^1$H-NMR (CDCl$_3$); δ (ppm) 2.06 (3H, s), 2.48 (3H, s), 3.96 (2H, s), 6.53-6.55 (1H, m), 6.59-6.61 (1H, m), 6.93 (1H, t, J=7.6 Hz), 7.37 (2H, d, J=8.0 Hz), 7.90 (2H, d, J=8.0 Hz).
MS (ESI); m/z 278 (M+H)$^+$ b) 2-(3,5-Dimethyl-1H-pyrazol-1-yl)-6-methylphenyl 4-methylbenzene sulfonate 48.8 mg of the title compound was obtained from 159.5 mg of 2-amino-6-methylphenyl 4-methylbenzene sulfonate in an analogous manner to Example 43c).
$^1$H-NMR (CDCl$_3$); δ (ppm) 2.09 (3H, s), 2.10 (3H, s), 2.43 (3H, s), 2.49 (3H, s), 5.67 (1H, s), 7.13-7.32 (5H, m), 7.48 (2H, d, J=8.0 Hz).
MS (ESI); m/z 357 (M+H)$^+$ c) 2-(3,5-Dimethyl-1H-pyrazol-1-yl)-6-methylphenol 12 mg of the title compound was obtained from 48.5 mg of 2-(3,5-dimethyl-1H-pyrazol-1-yl)-6-methylphenyl 4-methylbenzene sulfonate in an analogous manner to Example 43d).
$^1$H-NMR (CDCl$_3$); δ (ppm) 2.30 (3H, s), 2.31 (3H, s), 2.38 (3H, s), 6.03 (1H, s), 6.81 (1H, t, J=8.0 Hz), 7.03-7.09 (2H, m), 9.79 (1H, s).
MS (ESI); m/z 203 (M+H)$^+$

Example 52

2-(3,5-dimethyl-1H-pyrazol-1-yl)-5-ethylphenol a) 4-Chloro-5-ethyl-2-nitrophenyl methanesulfonate 150 mg of 4-chloro-5-ethyl-2-nitrophenol was dissolved in 1.5 ml of dichloromethane, and 156 µl of triethylamine and 69 µl of methanesulfonylchloride were added at room temperature and stirred for 30 minutes. To the reaction mixture was added 50 ml of water, and extracted with 60 ml of ethyl acetate. After the organic layer was dried over anhydrous magnesium sulfate, the solvent was distilled off under reduced pressure to yield 200.7 mg of the title compound.
$^1$H-NMR (CDCl$_3$); δ (ppm) 1.28 (3H, t, J=7.6 Hz), 2.83 (2H, q, J=7.6 Hz), 3.37 (3H, s), 7.42 (1H, s), 8.09 (1H, s).

b) 2-Amino-5-ethylphenyl methanesulfonate 200 mg of 4-chloro-5-ethyl-2-nitrophenyl methanesulfonate was dissolved in 4 ml of ethanol, and 200 mg of 10% palladium/carbon was added and stirred under hydrogen atmosphere at room temperature for 4 hours. After the insoluble matter was filtered off, the solvent was distilled off under reduced pressure to yield 74.9 mg of the title compound.
$^1$H-NMR (CD$_3$OD); δ (ppm) 1.26 (3H, t, J=7.6 Hz), 2.73 (2H, q, J=7.6 Hz), 3.47 (3H, s), 7.28-7.46 (3H, m).
MS (ESI); m/z 216 (M+H)$^+$ c) 2-(3,5-Dimethyl-1H-pyrazol-1-yl)-5-ethylphenyl methanesulfonate 28.1 mg of the title compound was obtained from 74.5 mg of 2-amino-5-ethylphenyl methanesulfonate in an analogous manner to Example 43c).
$^1$H-NMR (CDCl$_3$); δ (ppm) 1.28 (3H, t, J=7.6 Hz), 2.17 (3H, s), 2.26 (3H, s), 2.65 (3H, s), 2.73 (2H, q, J=7.6 Hz), 6.00 (1H, s), 7.24-7.26 (1H, m), 7.33-7.37 (2H, m).
MS (ESI); m/z 295 (M+H)$^+$ d) 2-(3,5-Dimethyl-1H-pyrazol-1-yl)-5-ethylphenol 28 mg of 2-(3,5-dimethyl-1H-pyrazol-1-yl)-5-ethylphenyl methanesulfonate was dissolved in 0.1 ml of methanol, and 0.07 ml of 5N-hydrochloric acid was added and heated at reflux for 30 minutes. To the reaction mixture added 15 ml of water, and extracted with 15 ml of ethyl acetate. After the organic layer was dried over anhydrous magnesium sulfate, the solvent was distilled off under reduced pressure, and purified using preparative thin-layer silica gel column chromatography (hexane:ethyl acetate=4:1) to yield 7.4 mg of the title compound.
$^1$H-NMR (CDCl$_3$); δ (ppm) 1.24 (3H, t, J=7.6 Hz), 2.29 (3H, s), 2.38 (3H, s), 2.63 (2H, q, J=7.6 Hz), 6.02 (1H, s), 6.73-6.75 (1H, m), 6.94 (1H, s), 7.10 (1H, d, J=8.0 Hz), 9.67 (1H, s).
MS (ESI); m/z 217 (M+H)$^+$

Example 53

2-(4-Fluoro-3,5-dimethyl-1H-pyrazol-1-yl)phenol a) 1-(2-Benzyloxyphenyl)-4-fluoro-3,5-dimethyl-1H-pyrazol 500 mg of 2-benzyloxyphenyl hydrazine hydrochloride and 251 mg of 3-fluoropentane-2,4-dione were added to 12 ml of ethanol, and heated at reflux for 1.5 hours. The reaction solution was concentrated under reduced pressure as it is and purified using silica gel column chromatography (hexane:ethyl acetate=6:1 to 5:1) to yield 417 mg of the title compound.
$^1$H-NMR (CDCl$_3$); δ (ppm) 2.07 (3H, s), 2.30 (3H, s), 5.04 (2H, s), 7.03-7.07 (2H, m), 7.24-7.37 (7H, m).
MS (ESI); m/z 297 (M+H)$^+$ b) 2-(4-Fluoro-3,5-dimethyl-1H-pyrazol-1-yl)phenol 416 mg of 1-(2-benzyloxyphenyl)-4-fluoro-3,5-dimethyl-1H-pyrazol was dissolved in 16 ml of methanol, and 42.6 mg of 10% palladium/carbon was added and stirred under hydrogen atmosphere at room temperature for a whole day and night. After the insoluble matter was filtered off, the filtrate was distilled off under reduced pressure and the resulting residue was purified using silica gel column chromatography (hexane:ethyl acetate=5:1) to yield 290 mg of the title compound.
$^1$H-NMR (CDCl$_3$); δ (ppm) 2.28 (3H, s), 2.33 (3H, s), 6.90 (1H, t, J=8.0 Hz), 7.06 (1H, d, J=8.0 Hz), 7.15 (1H, d, J=8.0 Hz), 7.19 (1H, t, J=8.0 Hz).
MS (ESI); m/z 207 (M+H)$^+$

Example 54

5-bromo-2-(3,5-dimethyl-1H-pyrazol-1-yl)phenol a) 5-bromo-2-hydrazinylphenol 4-methylbenzenesulfonate

To a suspension of 2-amino-5-bromophenol (1.0 g) in ethanol (7.0 mL) was added conc. hydrochloric acid (1.5 mL) dropwise at −10° C. To this solution, tert-butyl nitrite (636 mg) was added at the same temperature. The resulting mixture was stirred at the same temperature for 1 h to form diazonium salt solution. In a separate round-bottom flask stannous chloride dihydrate (2.49 g), p-toluene sulfonic acid monohydrate (1.08 g) and EtOH (15 mL) were added and stirred at −10° C. for 15 min. The above prepared diazonium salt solution was added dropwise at −10° C. to this solution. The reaction mixture was stirred at −10° C. for 1 h, and then tert-butyl methylether (30 mL) was added. The reaction mixture was stirred for 15 minutes. The resulting precipitate was filtered to give the title compound (0.9 g).

b) 5-bromo-2-(3,5-dimethyl-1H-pyrazol-1-yl)phenol 5-bromo-2-hydrazinylphenol 4-methylbenzenesulfonate (0.9 g) and acetylacetone (0.8 g) were added to ethanol (25 mL) refluxed for 1 h. Then the reaction mixture was cooled to room temperature and the solvent was evaporated under reduced pressure. The residue was dissolved in ethyl acetate (50 mL) and washed with saturated sodium bicarbonate solution (20 mL×2). The organic layer was dried over anhydrous $Na_2SO_4$, and concentrated under reduced pressure. The resulting residue was chromatographed over silica gel column eluted with hexane/ethyl acetate (4:1) to yield the title compound (650 mg).

$^1$H-NMR (CDCl$_3$); δ(ppm) 2.30 (3H, s), 2.40 (3H, s), 6.05 (1H, s), 7.01-7.08 (2H, m), 7.26 (1H, s).

MS (ESI); m/z 267 (M+H)$^+$

Example 55

5-bromo-2-(4-chloro-3,5-dimethyl-1H-pyrazol-1-yl)phenol 558 mg of the title compound was prepared in a manner similar to Example 54b) by using 5-bromo-2-hydrazinylphenol 4-methylbenzenesulfonate (0.9 g), which was prepared in a manner similar to Example 54a), and 3-chloropentane-2,4-dione (1.07 g).

$^1$H-NMR (CDCl$_3$); δ(ppm) 2.30 (3H, s), 2.38 (3H, s), 7.02-7.08 (2H, m), 7.27 (1H, d, J=2.0 Hz)), 9.62 (1H, s).

MS (ESI); m/z 303 (M+H)$^+$

Example 56

5-bromo-2-(3,4,5-trimethyl-1H-pyrazol-1-yl)phenol 320 mg of the title compound was prepared in a manner similar to Example 54b) by using 5-bromo-2-hydrazinylphenol 4-methylbenzenesulfonate (0.9 g), which was prepared in a manner similar to Example 54a), and 3-methylpentane-2,4-dione (0.9 g).

$^1$H-NMR (CDCl$_3$); δ(ppm) 1.98 (3H, s), 2.24 (3H, s), 2.31 (3H, s), 7.00-7.06 (2H, m), 7.25 (1H, d, J=1.6 Hz)), 10.34 (1H, s).

MS (ESI); m/z 281 (M+H)$^+$

Example 57

4-(3,5-dimethyl-1H-pyrazol-1-yl)-3-hydroxyphenyl acetate a) 4-nitro-1,3-phenylene diacetate To a solution of 4-nitrobenzene-1,3-diol (5.0 g) in methylene chloride (50 mL) was added pyridine (5.35 g), 4-dimethylaminopyridine (0.39 g) and acetic anhydride (8.12 g) successively with ice-cooling under nitrogen atmosphere. The resulting reaction mixture was warmed to room temperature and stirred for 1 h. Then the reaction mixture was washed with water (50 mL), 1N hydrochloric acid (100 mL), saturated aqueous sodium bicarbonate solution (100 mL) and saturated brine (100 mL) successively, and was dried over anhydrous sodium sulfate, and concentrated under reduced pressure to give the title compound (7.4 g).

$^1$H-NMR (CDCl$_3$); δ(ppm) 2.33 (3H, s), 2.37 (3H, s), 7.09 (1H, d, J=2.4 Hz), 7.18 (1H, dd, J=2.4, 9.2 Hz), 8.16 (1H, d, J=9.2 Hz).

b) 3-hydroxy-4-nitrophenyl acetate

To a solution of 4-nitro-1,3-phenylene diacetate (1.0 g) in chloroform (25 mL) was added aluminium chloride (2.23 g) with ice-cooling under nitrogen atmosphere. The reaction mixture was warmed to room temperature and stirred for 3 h. Then to the reaction mixture was added water (100 mL) and extracted with methylene chloride (30 mL×2). The combined organic layer was washed with 1N hydrochloric acid (25 mL) and saturated brine (25 mL) successively, dried over anhydrous sodium sulfate and was concentrated under reduced pressure. The residue was purified by column chromatography over silica gel using hexane/ethyl acetate (20:1) to give the title compound (610 mg).

$^1$H-NMR (CDCl$_3$): δ(ppm) 2.32 (3H, s), 6.77 (1H, dd, J=2.4 Hz, J=9.2 Hz), 6.95 (1H, d, J=2.4 Hz), 8.14 (1H, d, J=9.2 Hz), 10.70 (1H, s).

MS (ESI); m/z 196 (M−H)− c) 4-amino-3-hydroxyphenyl acetate

To a solution of 3-hydroxy-4-nitrophenyl acetate (3.0 g) in ethyl acetate (50 mL), 300 mg of palladium/carbon (10%) was added under nitrogen atmosphere. The resulting mixture was stirred under hydrogen atmosphere for 10 h at room temperature. The insoluble material was filtered off and the filtrate was concentrated under reduced pressure. The residue was purified by the column chromatography over silica gel using hexane/ethyl acetate(1:1) to give the title compound (2.48 g).

$^1$H-NMR (DMSO-d$_6$); δ(ppm) 2.17 (3H, s), 4.45 (2H, brs), 6.28 (1H, dd, J=2.4, 8.4 Hz), 6.40 (1H, d, J=2.4 Hz), 6.53 (1H, d, J=8.4 Hz), 9.26 (1H, brs).

MS (ESI); m/z 167 (M$^+$)

d) 4-(3,5-dimethyl-1H-pyrazol-1-yl)-3-hydroxyphenyl acetate 330 mg of the title compound was prepared in a manner similar to Example 54b) by using 4-hydrazinyl-3-hydroxyphenyl acetate 4-methylbenzenesulfonate (0.9 g), which was prepared from 4-amino-3-hydroxyphenyl acetate (1.0 g) in a manner similar to Example 54a), and acetylacetone (0.9 g).

$^1$H-NMR (CDCl$_3$); δ(ppm) 2.29 (3H, s), 2.30 (3H, s), 2.41 (3H, s), 6.04 (1H, s), 6.68 (1H, dd, J=2.4, 8.8 Hz), 6.85 (1H, d, J=2.4 Hz), 7.19 (1H, d, J=8.8 Hz), 10.14 (1H, s).

MS (ESI); m/z 247 (M+H)$^+$

Example 58

4-(4-chloro-3,5-dimethyl-1H-pyrazol-1-yl)-3-hydroxyphenyl acetate 30 mg of the title compound was prepared in a manner similar to Example 54b) by using 4-hydrazinyl-3-hydroxyphenyl acetate 4-methylbenzenesulfonate (0.9 g), which was prepared from 4-amino-3-hydroxyphenyl acetate (1.0 g) in a manner similar to Example 54a), and 3-chloropentane-2,4-dione (1.2 g).

$^1$H-NMR (CDCl$_3$); δ(ppm) 2.30 (3H, s), 2.31 (3H, s), 2.39 (3H, s), 6.70 (1H, dd, J=2.8, 8.8 Hz), 6.86 (1H, d, J=2.8 Hz), 7.17 (1H, d, J=8.8 Hz), 9.50 (1H, s).

MS (ESI); m/z 281 (M+H)$^+$

Example 59

3-hydroxy-4-(3,4,5-trimethyl-1H-pyrazol-1-yl)phenyl acetate 230 mg of the title compound was prepared in a manner similar to Example 54b) by using 4-hydrazinyl-3-hydroxyphenyl acetate 4-methylbenzenesulfonate (0.6 g), which was prepared from 4-amino-3-hydroxyphenyl acetate (1.0 g) in a manner similar to Example 54a), and 3-methylpentane-2,4-dione (1.0 g).

$^1$H-NMR (CDCl$_3$); δ(ppm) 1.99 (3H, s), 2.24 (3H, s), 2.30 (3H, s), 2.32 (3H, s), 6.66 (1H, dd, J=2.8, 8.4 Hz), 6.83 (1H, d, J=2.8 Hz), 7.17 (1H, d, J=8.4 Hz), 10.22 (1H, s).

MS (ESI); m/z 261 (M+H)$^+$

Example 60

2-(3,5-dimethyl-1H-pyrazol-1-yl)-4-methoxy-5-methylphenol a) 1,4-dimethoxy-2-methyl-5-nitrobenzene 2,5-dimethoxy toluene (6.0 g) was dissolved in acetic acid (20 mL). To the solution, a solution of fuming nitric acid (d=1.50, 4.32 g) in acetic acid (10 mL) was added dropwise at 40° C. over a period of 5 min. The mixture was stirred at 40° C. for 30 min. The reaction mixture was then allowed to cool to room temperature, which was stirred for another 30 min. Then the reaction mixture was diluted with cold water (300 mL). The resulting precipitate was filtered washed with cold water (100 mL) and dried under reduced pressure to afford the title compound (7.5 g).

$^1$H-NMR (CDCl$_3$); δ(ppm) 2.28 (3H, s), 3.84 (3H, s), 3.92 (3H, s), 6.90 (1H, s), 7.40 (1H, s).

MS (ESI); m/z 198 (M+H)$^+$ b) 4-methoxy-5-methyl-2-nitrophenol

A solution of 1,4-dimethoxy-2-methyl-5-nitrobenzene (6.0 g) in methylene chloride (30 mL) was cooled to −20° C., and a solution of boron trichloride (1.0 M in CH$_2$Cl$_2$) (30 mL) was added dropwise at −20° C. thereto. Then the reaction mixture was allowed to warm to room temperature and stirred for 16 h. To the reaction solution was then added saturated aqueous sodium bicarbonate solution (50 mL) and extracted with ethyl acetate (100 mL×3). The combined organic layer was washed with water (100 mL), saturated brine (50 mL), dried over anhydrous sodium sulfate, and evaporated under reduced pressure. The resulting residue was purified by column chromatography over silica gel using hexane/ethyl acetate (9:1) to give the title compound (4.25 g).

$^1$H-NMR (CDCl$_3$); δ(ppm) 2.26 (3H, s), 3.84 (3H, s), 6.94 (1H, s), 7.39 (1H, s), 10.46 (1H, s).

MS (ESI); m/z 182 (M−H)$^-$ c) 4-methoxy-5-methyl-2-nitrophenyl 4-methylbenzenesulfonate

To a solution of 4-methoxy-5-methyl-2-nitro phenol (8.0 g) in methylene chloride (80 mL) was added p-toluenesulfonyl chloride (9.15 g) at room temperature under nitrogen atmosphere. The mixture was cooled to 0° C. To this mixture triethylamine (4.86 g) was added and stirred for 2 h. Then the reaction mixture was poured into water (150 mL) and extracted with methylene chloride (150 mL). The organic layer was washed with water (100 mL) and saturated brine (50 mL), dried over anhydrous sodium sulfate and concentrated under reduced pressure. The residue was purified by column chromatography over silica gel using hexane/ethyl acetate (9:1) to give the title compound (12.0 g).

$^1$H-NMR (CDCl$_3$); δ(ppm) 2.26 (3H, s), 2.46 (3H, s), 3.87 (3H, s), 7.19 (1H, s), 7.33 (1H, s), 7.34 (2H, d, J=8.4 Hz), 7.77 (2H, d, J=8.4 Hz).

MS (ESI); m/z 336 (M−11)$^-$ d) 2-amino-4-methoxy-5-methylphenyl 4-methylbenzenesulfonate 3.2 g of the title compound was prepared in a manner similar to Example 57c) by using 4-methoxy-5-methyl-2-nitrophenyl 4-methylbenzenesulfonate (4.0 g).

$^1$H-NMR (DMSO-d6); δ(ppm) 1.91 (3H, s), 2.41 (3H, s), 3.64 (3H, s), 4.73 (2H, brs), 6.25 (1H, s), 6.64 (1H, s), 7.43 (2H, d, J=8.4 Hz), 7.79 (2H, d, J=8.4 Hz).

MS (ESI); m/z 308 (M+H)$^+$ e) 2-(3,5-dimethyl-1H-pyrazol-1-yl)-4-methoxy-5-methylphenyl-4-methylbenzenesulfonate 400 mg of the title compound was prepared in manners similar to Examples 54a) and 54b) by using 2-amino-4-methoxy-5-methylphenyl 4-methylbenzenesulfonate (1.0 g).

$^1$H-NMR (CDCl$_3$); δ(ppm) 2.10 (6H, s), 2.25 (3H, s), 2.41 (3H, s), 3.79 (3H, s), 5.80 (1H, s), 6.71 (1H, s), 7.15 (2H, d, J=8.4 Hz), 7.27 (1H, s), 7.35 (2H, d, J=8.4 Hz).

MS (ESI); m/z 387 (M+H)$^+$ f) 2-(3,5-dimethyl-1H-pyrazol-1-yl)-4-methoxy-5-methylphenol 70 mg of the title compound was prepared in a manner similar to Example 29 by using 2-(3,5-dimethyl-1H-pyrazol-1-yl)-4-methoxy-5-methylphenyl-4-methylbenzenesulfonate (200 mg).

$^1$H-NMR (CDCl$_3$); δ(ppm) 2.21 (3H, s), 2.29 (3H, s), 2.39 (3H, s), 3.78 (3H, s), 6.02 (1H, s), 6.67 (1H, s), 6.89 (1H, s), 8.87 (1H, s).

MS (ESI); m/z 233 (M+H)$^+$

Example 61

4-chloro-2-(3,5-dimethyl-1H-pyrazol-1-yl)-5-methylphenol a) 2-amino-4-chloro-5-methylphenol

To a solution of 4-chloro-5-methyl-2-nitrophenol (5.0 g) in methanol (100 mL) at 0° C. was added zinc powder (8.71 g), which was activated by hydrochloric acid in advance, and a solution of ammonium chloride (7.1 g) in water (20 mL). The suspension was stirred for 4 h at room temperature. Then the insoluble material was filtered off through celite, and the celite cake was washed with ethyl acetate (100 mL). The filtrate and washings were combined and concentrated under reduced pressure. The residue was purified by column chromatography over silica gel using hexane/ethyl acetate (3:2) to yield the title compound (1.4 g).

$^1$H-NMR (DMSO-d$_6$); δ(ppm) 2.10 (3H, s), 4.57 (2H, brs), 6.54 (1H, s), 6.58 (1H, s), 9.11 (1H, s).

MS (ESI); m/z 157 (M)$^+$ b) 4-chloro-2-(3,5-dimethyl-1H-pyrazol-1-yl)-5-methylphenol 120 mg of the title compound was prepared in manners similar to Examples 54a) and 54b) by using 2-amino-4-chloro-5-methylphenol (1.0 g).
$^1$H-NMR (CDCl$_3$); δ(ppm) 2.29 (3H, s), 2.34 (3H, s), 2.41 (3H, s), 6.03 (1H, s), 6.96 (1H, s), 7.19 (1H, s), 9.88 (1H, s).
MS (ESI); m/z 237 (M+H)$^+$ Example 62

2-(3,5-dimethyl-1H-pyrazol-1-yl)-4,5-dimethylphenol 630 mg of the title compound was prepared in manners similar to Examples 54a) and 54b) by using 2-amino-4,5-dimethylphenol (1.0 g).
$^1$H-NMR (CDCl$_3$); δ(ppm) 2.21 (3H, s), 2.24 (3H, s), 2.29 (3H, s), 2.38 (3H, s), 6.00 (1H, s), 6.88 (1H, s), 6.94 (1H, s), 9.28 (1H, s).
MS (ESI); m/z 217 (M+H)$^+$ Example 63

4-(4-chloro-3,5-dimethyl-1H-pyrazol-1-yl)benzene-1,3-diol 200 mg of the title compound was isolated during purification by silica gel column chromatography in Example 58 as a byproduct.
$^1$H-NMR (CD$_3$OD); δ(ppm) 2.07 (3H, s), 2.20 (3H, s), 6.36 (1H, dd, J=2.4, 8.4 Hz), 6.42 (1H, d, J=2.4 Hz), 6.98 (1H, d, J=8.4 Hz).
MS (ESI); m/z 239 (M+H)$^+$ Test Example 1

Measurement of Antifungal Activity

Measurement of antifungal activity was conducted by the following method. Compounds for evaluation were dissolved in dimethyl sulfoxide (DMSO) and used. As the test medium, RPMI1640 medium containing 0.165 M 3-morpholinopropane sulfonic acid (MOPS) was used. As the test strain, *T. mentagrophytes* ATCC18748 or *T. rubrum* ATCC10218 was used. 100 μL of the test strain was dispensed at a concentration of 1×10$^4$ conidia/mL, mixed with compounds for evaluation on 96 well half area plate so that the concentration of DMSO becomes 1%, and cultured at a culture temperature of 28° C. for 3 days (for *T. mentagrophytes*) or for 4 days (for *T. rubrum*). Then, 5 μL of Cell Counting Kit8 (WST8) was added and the absorbances at 450 nm and 595 nm was measured as background. Subsequently, they were incubated at 28° C. for 5 hours (for *T. mentagrophytes*) or overnight (for *T. rubrum*), and again measured the absorbances at 450 nm and 595 nm was measured, and then calculated the growth inhibition percentages using the differences from the background, and 80% growth inhibition concentration was regarded as MIC (μg/ml).

TABLE 1

| Example No. | MIC (*T. mentagrophytes*) | MIC (*T. rubrum*) |
| --- | --- | --- |
| 1 | B | B |
| 5 | C | D |
| 6 | C | E |
| 7 | C | E |
| 8 | C | E |
| 9 | A | A |
| 10 | D | E |
| 11 | C | D |
| 12 | C | E |
| 13 | A | B |
| 14 | B | B |
| 15 | C | C |
| 16 | C | E |
| 17 | A | A |
| 18 | B | B |
| 19 | C | C |
| 20 | C | D |
| 21 | A | B |
| 22 | C | D |
| 23 | C | D |
| 24 | A | C |
| 25 | B | B |
| 26 | A | A |
| 28 | B | C |
| 30 | A | A |
| 31 | B | B |
| 32 | B | B |
| 33 | B | A |
| 34 | B | B |
| 35 | C | C |
| 36 | E | D |
| 37 | B | B |
| 38 | C | B |
| 39 | C | C |
| 40 | E | D |
| 41 | D | D |
| 42 | C | D |
| 43 | E | D |
| 44 | A | A |
| 45 | A | A |
| 46 | E | D |
| 47 | B | B |
| 48 | B | B |
| 49 | E | D |
| 50 | B | B |
| 51 | E | D |
| 52 | A | A |
| 53 | B | B |
| 54 | A | A |
| 55 | A | A |
| 56 | A | A |
| 57 | B | B |
| 58 | B | A |
| 59 | B | B |
| 61 | C | C |
| 63 | A | A |
| Amorolfine hydrochloride | A | A |
| Terbinafine hydrochloride | A | A |

| MIC (*T. mentagrophytes*) | | MIC (*T. rubrum*) | |
| --- | --- | --- | --- |
| A | ≤1 μg/ml | A | ≤2 μg/ml |
| B | 2-8 μg/ml | B | 4-16 μg/ml |
| C | 16-32 μg/ml | C | 16-32 μg/ml |
| D | Inhibition of 50% or more to less than 80% at 32 μg/ml | D | >32-64 μg/ml |
| E | Inhibition of less than 50% at 32 μg/ml | E | >64 μg/ml |

Test Example 2

Nail Permeability Test

Example compounds and comparative compounds (amorolfine hydrochloride, terbinafine hydrochloride and ciclopirox) were each dissolved in a solution of ethyl acetate: propylene glycol (1:1) or dimethyl sulfoxide at a concentration of 10 mg/mL. 2 μL each of the solutions was added to a bovine hoof slice (about 100 μm thickness) placed on a low-melting-point agarose. After incubation at 28° C. for 5 days, the agaroses were collected, distilled water was added thereto, and the mixtures were heated and dissolved. The concentrations of the compounds in the solutions were determined using a high performance liquid chromatography/mass spectrometry apparatus to obtain the amounts of the agents permeated through the nail and calculate the permeabilities of the respective agents.

As a result, it was found that Example Compounds show much higher nail permeabilities compared with amorolfine hydrochloride, and terbinafine hydrochloride.

TABLE 2

| Example No. | Nail permeability |
|---|---|
| 1 | B |
| 2 | B |
| 3 | B |
| 4 | D |
| 5 | C |
| 6 | D |
| 7 | C |
| 8 | A |
| 9 | C |
| 10 | C |
| 11 | C |
| 12 | C |
| 13 | C |
| 14 | C |
| 15 | C |
| 16 | C |
| 17 | C |
| 18 | C |
| 19 | C |
| 20 | C |
| 21 | D |
| 22 | C |
| 23 | C |
| 24 | D |
| 25 | B |
| 26 | C |
| 27 | B |
| 28 | C |
| 29 | B |
| 30 | D |
| 31 | A |
| 32 | C |
| 33 | B |
| 34 | B |
| 35 | C |
| 36 | A |
| 37 | B |
| 38 | B |
| 39 | A |
| 40 | C |
| 41 | B |
| 42 | C |
| 43 | C |
| 44 | B |
| 45 | B |
| 46 | B |
| 47 | A |
| 48 | B |
| 49 | C |
| 50 | D |
| 51 | C |
| 52 | C |
| 53 | C |
| 54 | C |
| 55 | D |
| 56 | D |
| 60 | C |
| 61 | C |

TABLE 2-continued

| | |
|---|---|
| 62 | C |
| 63 | C |
| Amorolfine hydrochloride | E |
| Terbinafine hydrochloride | E |

Nail permeability

A 35-60%
B 10-less than 35%
C 1-less than 10%
D 0.1-less than 1%
E <0.1%

INDUSTRIAL APPLICABILITY

As stated above, there has been a strong demand for the development of a topical agent for tinea unguium which has not only an anti-Trichophyton activity but also a high nail permeability. The present inventors have successfully provided with an anti-fungal agent for tinea comprising a compound represented by formula (I) or a salt thereof as an active ingredient which has a strong anti-Trichophyton activity and a high nail permeability. In addition, the agent of the present invention can be used as a topical agent and by using the topical agent of the present invention, drug interactions, hepatic disorders and side effects from prolonged administration of the approved oral antifungal agent can be overcome. The present invention offers treatment options for the patients infected with *Trichophyton* who have to avoid oral administration.

The invention claimed is:

1. A compound represented by the following formula (I), wherein:

$R^1$ represents a hydrogen atom, a $C_{1-6}$alkyl or a trifluoromethyl group;

$R^2$ represents a hydrogen atom, a $C_{1-6}$alkyl, a halogen, a —COO($C_{1-6}$alkyl) or a —$(CH_2)_{1-3}$COOR group, wherein R represents a hydrogen atom or a $C_{1-6}$alkyl;

$R^3$ represents a hydrogen atom, a $C_{1-6}$alkyl, an amino, a trifluoromethyl group or an —OR group, R represents a hydrogen atom or a $C_{1-6}$alkyl;

$R^4$ represents a hydroxyl group;

$R^5$ represents a hydrogen atom, a $C_{1-6}$alkyl, a hydroxyl group or a halogen;

$R^6$ represents a $C_{1-6}$alkyl, a trifluoromethyl group, a halogen, an amino group, a —$NR^aR^b$ group, a nitro group, a hydroxy $C_{1-6}$alkyl, a —$CONR^aR^b$ group, a —COO($C_{1-6}$alkyl), a —COOH, a —$(CH_2)_{1-3}$COOR group, or an —$OR^a$ group, wherein R represents a hydrogen atom or a $C_{1-6}$alkyl, and $R^a$ and $R^b$ are the same or different from each other and represent a hydrogen atom, a $C_{1-6}$alkyl or a $C_{1-6}$acyl;

$R^7$ represents a hydrogen atom, a $C_{1-6}$alkyl, an —OR group, wherein R represents a hydrogen atom or a $C_{1-6}$alkyl; and $R^8$ represents a hydrogen atom, a $C_{1-6}$alkyl, a hydroxyl group, an amino group or a nitro group, with the proviso that when $R^1$ is a hydrogen atom, $R^3$ is not a hydrogen atom, and the compound wherein $R^1$ is tert-butyl group, $R^3$ is an amino group, $R^4$ is a hydroxyl group and $R^6$ is a methyl group is excluded, or a salt thereof

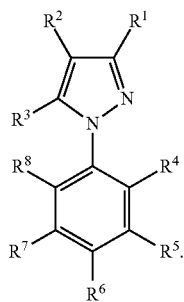

(I)

2. The compound according to claim 1,
wherein:
$R^1$ represents a $C_{1-6}$alkyl or a trifluoromethyl group;
$R^3$ represents $C_{1-6}$alkyl, trifluoromethyl, or an —OR group wherein R represents a hydrogen atom or a $C_{1-6}$alkyl,
or a salt thereof.

3. The compound according to claim 1,
wherein:
$R^1$ represents a $C_{1-6}$alkyl;
$R^3$ represents a $C_{1-6}$alkyl,
or a salt thereof.

4. The compound according to claim 1,
wherein:
$R^1$ represents a $C_{1-4}$alkyl;
$R^2$ represents a hydrogen atom, a $C_{1-4}$alkyl, or a halogen;
$R^3$ represents a $C_{1-4}$alkyl;
$R^4$ represents a hydroxyl group;
$R^5$ represents a hydrogen atom;
$R^6$ represents a $C_{1-4}$alkyl, a trifluoromethyl group, a halogen, an amino group, a —$NR^aR^b$ group, a nitro group, a hydroxy $C_{1-4}$alkyl, a —$CONR^aR^b$ group, a —COO($C_{1-4}$alkyl), a —COOH, a —$(CH_2)_{1-3}COOR$ group, or an —$OR^a$ group, wherein R represents a hydrogen atom or a $C_{1-4}$alkyl, and $R^a$ and $R^b$ are the same or different from each other and represent a hydrogen atom, a $C_{1-4}$alkyl or a $C_{1-4}$acyl;
$R^7$ represents a hydrogen atom; and
$R^8$ represents a hydrogen atom, a $C_{1-4}$alkyl, a hydroxyl group, an amino group, or a nitro group,
or a salt thereof.

5. The compound according to claim 1,
wherein:
$R^1$ represents a methyl group;
$R^2$ represents a hydrogen atom, a methyl group or a halogen;
$R^3$ represents a methyl group;
$R^4$ represents a hydroxyl group;
$R^5$ represents a hydrogen atom;
$R^6$ represents a $C_{1-3}$alkyl, a trifluoromethyl group, a halogen, an amino group, a —$NR^aR^b$ group, a nitro group, a hydroxy $C_{1-3}$alkyl, a —$CONRaRb$, a —COO($C_{1-3}$alkyl), a —COOH, a —$(CH_2)_{1-3}COOR$ group, or an —$OR^a$ group, wherein R represents a hydrogen atom or a $C_{1-3}$alkyl, and $R^a$ and $R^b$ may be are the same or different from each other and represent a hydrogen atom, a $C_{1-3}$alkyl or a $C_{1-3}$acyl;
$R^7$ represents a hydrogen atom; and
$R^8$ represents a hydrogen atom,
or a salt thereof.

6. A compound which is selected from the group consisting of
2-(3,5-dimethyl-1H-pyrazol-1-yl)-4-fluorophenol,
2-(5-hydroxy-3-methyl-1H-pyrazol-1-yl)phenol,
2-(5-methyl-3-(trifluoromethyl)-1H-pyrazol-1-yl)phenol,
2-(3,5-bistrifluoromethyl)-1H-pyrazol-1-yl)phenol,
2-(5-methyl-1H-pyrazol-1-yl)phenol,
2-(3,4,5-trimethyl-1H-pyrazol-1-yl)phenol,
2-(5-amino-3-tert-butyl-1H-pyrazol-1-yl)phenol,
4-chloro-2-(3,5-dimethyl-1H-pyrazol-1-yl)phenol,
2-chloro-6-(3,5-dimethyl-1H-pyrazol-1-yl)phenol,
2-(4-chloro-3,5-dimethyl-1H-pyrazol-1-yl)phenol,
2-(3,5-diethyl-1H-pyrazol-1-yl)phenol,
3-(3,5-dimethyl-1H-pyrazol-1-yl)benzene-1,2-diol,
2-(4-ethyl-3,5-dimethyl-1H-pyrazol-1-yl)phenol,
5-fluoro-2-(3,4,5-trimethyl-1H-pyrazol-1-yl)phenol,
4-fluoro-2-(3,4,5-trimethyl-1H-pyrazol-1-yl)phenol,
2-(4-chloro-3,5-dimethyl-1H-pyrazol-1-yl)-5-fluorophenol,
ethyl 1-(2-hydroxyphenyl)-3,5-dimethyl-1H-pyrazol-4-carboxylate,
methyl 3-(1-(2-hydroxyphenyl)-3,5-dimethyl-1H-pyrazol-4-yl)propanoate,
2-(4-butyl-3,5-dimethyl-1H-pyrazol-1-yl)phenol,
2-(3,5-dimethyl-1H-pyrazol-1-yl)-5-fluorophenol,
5-chloro-2-(3,5-dimethyl-1H-pyrazol-1-yl)phenol,
2-(3,5-dimethyl-1H-pyrazol-1-yl)-3-nitrophenol,
2-(3,5-dimethyl-1H-pyrazol-1-yl)-5-nitrophenol,
3-(1-(2-hydroxyphenyl)-3,5-dimethyl-1H-pyrazol-4-yl)propionic acid,
5-chloro-2-(3,4,5-trimethyl-1H-pyrazol-1-yl)phenol,
5-amino-2-(3,5-dimethyl-1H-pyrazol-1-yl)phenol,
5-nitro-2-(3,4,5-trimethyl-1H-pyrazol-1-yl)phenol,
4-(3,5-dimethyl-1H-pyrazol-1-yl)benzene-1,3-diol,
5-amino-2-(3,4,5-trimethyl-1H-pyrazol-1-yl)phenol
methyl 4-(3,5-dimethyl-1H-pyrazol-1-yl)-3-hydroxybenzene carboxylate,
3-amino-2-(3,5-dimethyl-1H-pyrazol-1-yl)phenol,
4-(3,5-dimethyl-1H-pyrazol-1-yl)-3-hydroxybenzene carboxylic acid,
4-(3,5-dimethyl-1H-pyrazol-1-yl)-3-hydroxy-N,N-dimethyl benzamide,
4-(3,5-dimethyl-1H-pyrazol-1-yl)-3-hydroxy benzamide,
3-hydroxy-4-(3,4,5-trimethyl-1H-pyrazol-1-yl)benzene carboxylic acid,
3-hydroxy-4-(3,4,5-trimethyl-1H-pyrazol-1-yl)benzamide,
4-(4-chloro-3,5-dimethyl-1H-pyrazol-1-yl)-3-hydroxy benzamide,
2-(3,5-dimethyl-1H-pyrazol-1-yl)benzene-1,3-diol,
2-(3,5-dimethyl-1H-pyrazol-1-yl)-5-methylphenol,
2-(3,5-dimethyl-1H-pyrazol-1-yl)-5-methoxyphenol,
2-(3,5-dimethyl-1H-pyrazol-1-yl)-3-methylphenol,
2-(3,5-dimethyl-1H-pyrazol-1-yl)-5-hydroxymethylphenol,
2-(3,5-dimethyl-1H-pyrazol-1-yl)-5-methylaminophenol,
2-(3,5-dimethyl-1H-pyrazol-1-yl)-4-methylphenol,
2-(3,5-dimethyl-1H-pyrazol-1-yl)-5-trifluoromethylphenol,
2-(3,5-dimethyl-1H-pyrazol-1-yl)-6-methylphenol,
2-(3,5-dimethyl-1H-pyrazol-1-yl)-5-ethylphenol,
2-(4-fluoro-3,5-dimethyl-1H-pyrazol-1-yl)phenol,
5-bromo-2-(3,5-dimethyl-1H-pyrazol-1-yl)phenol,
5-bromo-2-(4-chloro-3,5-dimethyl-1H-pyrazol-1-yl)phenol,
5-bromo-2-(3,4,5-trimethyl-1H-pyrazol-1-yl)phenol, 4-(3,5-dimethyl-1H-pyrazol-1-yl)-3-hydroxyphenyl acetate,
4-(4-chloro-3,5-dimethyl-1H-pyrazol-1-yl)-3-hydroxyphenyl acetate,
3-hydroxy-4-(3,4,5-trimethyl-1H-pyrazol-1-yl)phenyl acetate,
2-(3,5-dimethyl-1H-pyrazol-1-yl)-4-methoxy-5-methylphenol,
4-chloro-2-(3,5-dimethyl-1H-pyrazol-1-yl)-5-methylphenol,
2-(3,5-dimethyl-1H-pyrazol-1-yl)-4,5-dimethylphenol, and
4-(4-chloro-3,5-dimethyl-1H-pyrazol-1-yl)-benzene-1,3-diol
or a salt thereof.

7. An anti-fungal composition for tinea comprising a pharmaceutically effective amount of a compound represented by the following formula (II), wherein:
$R^9$ represents a hydrogen atom, a $C_{1-6}$alkyl or a trifluoromethyl group;
$R^{10}$ represents a hydrogen atom, a $C_{1-6}$alkyl, a halogen, a —COO($C_{1-6}$alkyl) or a —$(CH_2)_{1-3}$COOR group, wherein R represents a hydrogen atom or a $C_{1-6}$alkyl,
$R^{11}$ represents a hydrogen atom, a $C_{1-6}$alkyl, an amino group, a trifluoromethyl group or an —OR group, wherein R represents a hydrogen atom or a $C_{1-6}$alkyl;
$R^{12}$ represents a hydroxyl group;
$R^{13}$ represents a hydrogen atom, a $C_{1-6}$alkyl, a hydroxyl group or a halogen;
$R^{14}$ represents a hydrogen atom, a $C_{1-6}$alkyl, a trifluoromethyl group, a halogen, an amino group, a —$NR^aR^b$ group, a nitro group, a hydroxy $C_{1-6}$alkyl, a —$CONR^aR^b$ group, a —COO($C_{1-6}$alkyl), a —COOH, a —$(CH_2)_{1-3}$COOR group, or an —$OR^a$ group, wherein R represents a hydrogen atom or a $C_{1-6}$alkyl, and $R^a$ and $R^b$ are the same or different from each other and represent a hydrogen atom, a $C_{1-6}$alkyl or a $C_{1-6}$acyl;
$R^{15}$ represents a hydrogen atom, a $C_{1-6}$alkyl, an —OR group, wherein R represents a hydrogen atom or a $C_{1-6}$alkyl or a halogen; and
$R^{16}$ represents a hydrogen atom, a $C_{1-6}$alkyl, a hydroxyl group, an amino group or a nitro group,
or a salt thereof

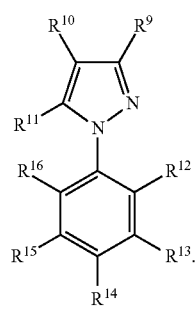

(II)

8. An anti-tinea unguium composition comprising a pharmaceutically effective amount of the compound of claim 1, or a salt thereof, and a pharmaceutically acceptable carrier.
9. The anti-fungal composition for tinea according to claim 7, which is a composition for topical administration.
10. The anti-tinea unguium composition according to claim 8, which is a composition for topical administration.

11. An anti-tinea unguium composition comprising a pharmaceutically effective amount of the compound of claim 6, or a salt thereof, and a pharmaceutically acceptable carrier.
12. An anti-tinea unguium composition comprising a pharmaceutically effective amount of a compound represented by the following formula (II), wherein:
$R^9$ represents a hydrogen atom, a $C_{1-6}$alkyl or a trifluoromethyl group;
$R^{10}$ represents a hydrogen atom, a $C_{1-6}$alkyl, a halogen, a —COO($C_{1-6}$alkyl) or a —$(CH_2)_{1-3}$COOR group, wherein R represents a hydrogen atom or a $C_{1-6}$alkyl,
$R^{11}$ represents a hydrogen atom, a $C_{1-6}$alkyl, an amino group, a trifluoromethyl group or an —OR group, wherein R represents a hydrogen atom or a $C_{1-6}$alkyl;
$R^{12}$ represents a hydroxyl group;
$R^{13}$ represents a hydrogen atom, a $C_{1-6}$alkyl, a hydroxyl group or a halogen;
$R^{14}$ represents a hydrogen atom, a $C_{1-6}$alkyl, a trifluoromethyl group, a halogen, an amino group, a —$NR^aR^b$ group, a nitro group, a hydroxy $C_{1-6}$alkyl, a —$CONR^aR^b$ group, a —COO($C_{1-6}$alkyl), a —COOH, a —$(CH_2)_{1-3}$COOR group, or an —$OR^a$ group, wherein R represents a hydrogen atom or a $C_{1-6}$alkyl, and $R^a$ and $R^b$ are the same or different from each other and represent a hydrogen atom, a $C_{1-6}$alkyl or a $C_{1-6}$acyl;
$R^{15}$ represents a hydrogen atom, a $C_{1-6}$alkyl, an —OR group, wherein R represents a hydrogen atom or a $C_{1-6}$alkyl or a halogen; and
$R^{16}$ represents a hydrogen atom, a $C_{1-6}$alkyl, a hydroxyl group, an amino group or a nitro group,
or a salt thereof

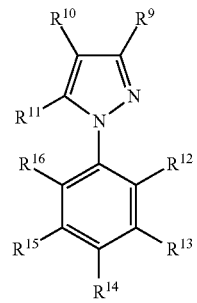

(II)

and a pharmaceutically acceptable carrier.
13. The anti-tinea unguium composition according to claim 11, which is a composition for topical administration.
14. The anti-tinea unguium composition according to claim 12, which is a composition for topical administration.
15. The compound according to claim 6, wherein the compound is 2-(3,5-dimethyl-1H-pyrazol-1-yl)-5-methylphenol or salt thereof.
16. An anti-fungal composition for tinea comprising a pharmaceutically effective amount of the compound of claim 15 or a salt thereof, and a pharmaceutically acceptable carrier.
17. An anti-tinea unguium composition comprising a pharmaceutically effective amount of the compound of claim 15 or a salt thereof, and a pharmaceutically acceptable carrier.
18. The anti-fungal composition for tinea according to claim 16, which is a composition for topical administration.
19. The anti-tinea unguium composition according to claim 17, which is a composition for topical administration.
20. A method for treating tinea comprising administering a pharmaceutically effective amount of the compound of claim 1 or a salt thereof to a subject in need thereof.

21. A method for treating tinea ungium comprising administering a pharmaceutically effective amount of the compound of claim 1 or a salt thereof to a subject in need thereof.

22. A method for treating tinea comprising administering a pharmaceutically effective amount of the compound of claim 15 or a salt thereof to a subject in need thereof.

23. A method for treating tinea ungium comprising administering a pharmaceutically effective amount of the compound of claim 15 or a salt thereof to a subject in need thereof.

* * * * *